United States Patent
Rock et al.

(10) Patent No.: US 8,721,568 B2
(45) Date of Patent: May 13, 2014

(54) METHOD FOR PERFORMING AN ORTHOPAEDIC SURGICAL PROCEDURE

(75) Inventors: Mick Rock, Leeds (GB); Jason T. Sherman, Warsaw, IN (US); Mario Bertazzoni, Vigevano (IT)

(73) Assignee: DePuy (Ireland) (IE)

( * ) Notice: Subject to any disclaimer, the term of this patent is extended or adjusted under 35 U.S.C. 154(b) by 1216 days.

(21) Appl. No.: 12/415,290

(22) Filed: Mar. 31, 2009

(65) Prior Publication Data

US 2010/0249789 A1    Sep. 30, 2010

(51) Int. Cl.
 *A61B 5/00*    (2006.01)
(52) U.S. Cl.
 USPC .......................................... 600/595; 600/587
(58) Field of Classification Search
 USPC ................ 600/300, 424, 438, 587, 594–595; 606/71, 85, 87–88, 90, 102, 280; 623/20.14, 20.36, 23.41, 914; 707/758
 See application file for complete search history.

(56) References Cited

U.S. PATENT DOCUMENTS

| | | | |
|---|---|---|---|
| 4,501,266 A * | 2/1985 | McDaniel | 606/90 |
| 4,566,448 A | 1/1986 | Rohr | |
| 4,795,473 A | 1/1989 | Grimes | |
| 4,796,610 A | 1/1989 | Cromartie | |
| 4,804,000 A | 2/1989 | Lamb | |
| 4,808,186 A | 2/1989 | Smith | |
| 4,822,362 A | 4/1989 | Walker | |
| 4,825,857 A | 5/1989 | Kenna | |
| 4,828,562 A | 5/1989 | Kenna | |
| 4,834,057 A | 5/1989 | McLeod | |
| 4,856,993 A | 8/1989 | Maness et al. | |
| 4,888,021 A | 12/1989 | Forte | |
| 4,892,093 A | 1/1990 | Zarnowski | |
| 4,892,546 A | 1/1990 | Kotz | |
| 4,899,761 A | 2/1990 | Brown et al. | |
| 4,907,578 A | 3/1990 | Petersen | |
| 4,926,847 A | 5/1990 | Luckman | |
| 4,932,974 A | 6/1990 | Pappas | |
| 4,935,023 A | 6/1990 | Whiteside | |

(Continued)

FOREIGN PATENT DOCUMENTS

| | | |
|---|---|---|
| DE | 10335410 A1 | 2/2005 |
| EP | 0720834 B1 | 6/1999 |

(Continued)

OTHER PUBLICATIONS

European Search Report for European Patent Application No. 10156105.8-2319, Jun. 15, 2010, 8 pgs.

(Continued)

*Primary Examiner* — Max Hindenburg
*Assistant Examiner* — Jonathan M Foreman
(74) *Attorney, Agent, or Firm* — Barnes & Thornburg LLP

(57) ABSTRACT

A method for performing an orthopaedic surgical procedure on a knee joint of a patient includes resecting a proximal end of a patient's tibia to create a resected surface of the patient's tibia and positioning a tibial paddle of a sensor module on the proximal end of the patient's tibia. The tibial paddle includes a sensor array generating sensor signals indicative of the joint force of the patient's knee joint. The method also includes performing a number of orthopaedic surgical steps while monitoring a display of the sensor module that provides a visual indication of the medial-lateral balance of the joint force of the patient's knee joint.

18 Claims, 36 Drawing Sheets

(56) References Cited

U.S. PATENT DOCUMENTS

| | | |
|---|---|---|
| 4,936,853 A | 6/1990 | Fabian et al. |
| 4,938,762 A | 7/1990 | Wehrli |
| 4,944,756 A | 7/1990 | Kenna |
| 4,959,071 A | 9/1990 | Brown |
| 4,963,153 A | 10/1990 | Noesberger |
| 4,973,331 A | 11/1990 | Pursley et al. |
| 4,979,949 A | 12/1990 | Matsen et al. |
| 4,986,281 A | 1/1991 | Preves et al. |
| 5,002,547 A | 3/1991 | Poggie et al. |
| 5,018,514 A | 5/1991 | Grood et al. |
| 5,020,797 A | 6/1991 | Burns |
| 5,032,132 A | 7/1991 | Matsen |
| 5,033,291 A | 7/1991 | Podoloff et al. |
| 5,037,423 A | 8/1991 | Kenna |
| 5,056,530 A | 10/1991 | Butler et al. |
| 5,080,675 A | 1/1992 | Lawes et al. |
| 5,082,003 A | 1/1992 | Lamb et al. |
| 5,098,436 A | 3/1992 | Ferrante et al. |
| 5,122,144 A | 6/1992 | Bert |
| 5,125,408 A | 6/1992 | Basser |
| 5,129,909 A | 7/1992 | Sutherland |
| 5,197,488 A | 3/1993 | Kovacevic |
| 5,207,711 A | 5/1993 | Caspari et al. |
| 5,213,112 A | 5/1993 | Niwa |
| 5,228,459 A | 7/1993 | Caspari et al. |
| 5,234,433 A | 8/1993 | Bert |
| 5,234,434 A | 8/1993 | Goble |
| 5,234,435 A | 8/1993 | Seagrave |
| 5,236,432 A | 8/1993 | Matsen et al. |
| 5,250,050 A | 10/1993 | Poggie et al. |
| 5,257,996 A | 11/1993 | McGuire |
| 5,312,411 A | 5/1994 | Steele et al. |
| 5,326,363 A | 7/1994 | Aikins |
| 5,329,933 A | 7/1994 | Graf |
| 5,342,367 A | 8/1994 | Ferrante et al. |
| 5,358,527 A | 10/1994 | Forte |
| 5,360,016 A | 11/1994 | Kovacevic et al. |
| 5,364,401 A | 11/1994 | Ferrante |
| 5,364,402 A | 11/1994 | Mumme |
| 5,395,401 A | 3/1995 | Bahler |
| 5,403,319 A | 4/1995 | Matsen et al. |
| 5,417,694 A | 5/1995 | Marik et al. |
| 5,425,775 A | 6/1995 | Kovacevic |
| 5,431,652 A | 7/1995 | Adachi et al. |
| 5,431,653 A | 7/1995 | Callaway |
| 5,443,518 A | 8/1995 | Insall |
| 5,456,724 A | 10/1995 | Yen et al. |
| 5,470,354 A | 11/1995 | Hershberger et al. |
| 5,489,311 A | 2/1996 | Cipolletti |
| 5,496,352 A | 3/1996 | Renger |
| 5,514,144 A | 5/1996 | Bolton |
| 5,514,183 A | 5/1996 | Epstein |
| 5,520,695 A | 5/1996 | Luckman |
| 5,540,696 A | 7/1996 | Booth et al. |
| 5,562,674 A | 10/1996 | Stalcup et al. |
| 5,569,261 A | 10/1996 | Marik et al. |
| 5,571,110 A | 11/1996 | Matsen et al. |
| 5,571,197 A | 11/1996 | Insall |
| 5,597,379 A | 1/1997 | Haines |
| 5,611,774 A | 3/1997 | Postelmans |
| 5,613,971 A | 3/1997 | Lower |
| 5,630,820 A | 5/1997 | Todd |
| 5,643,272 A | 7/1997 | Haines |
| 5,649,929 A | 7/1997 | Callaway |
| 5,656,785 A | 8/1997 | Trainor et al. |
| 5,658,293 A | 8/1997 | Vanlaningham |
| 5,669,914 A | 9/1997 | Eckhoff |
| 5,671,695 A | 9/1997 | Schroeder |
| 5,682,886 A | 11/1997 | Delp et al. |
| 5,683,397 A | 11/1997 | Vendrely et al. |
| 5,688,280 A | 11/1997 | Booth, Jr. et al. |
| 5,688,282 A | 11/1997 | Baron et al. |
| 5,690,635 A | 11/1997 | Matsen et al. |
| 5,702,422 A | 12/1997 | Stone |
| 5,702,463 A | 12/1997 | Pothier et al. |
| 5,733,292 A | 3/1998 | Gustilo et al. |
| 5,735,904 A | 4/1998 | Pappas |
| 5,743,909 A | 4/1998 | Collette |
| 5,769,894 A | 6/1998 | Ferragamo |
| 5,782,925 A | 7/1998 | Collazo et al. |
| 5,800,438 A | 9/1998 | Tuke |
| 5,800,552 A | 9/1998 | Forte |
| 5,810,827 A | 9/1998 | Haines |
| 5,824,104 A | 10/1998 | Tuke |
| 5,840,047 A | 11/1998 | Stedham |
| 5,860,980 A | 1/1999 | Axelson et al. |
| 5,871,018 A | 2/1999 | Delp et al. |
| 5,879,389 A | 3/1999 | Koshino |
| 5,880,976 A | 3/1999 | DiGioia, III et al. |
| 5,891,150 A | 4/1999 | Chan |
| 5,911,723 A | 6/1999 | Ashby |
| 5,931,777 A | 8/1999 | Sava |
| 5,935,086 A | 8/1999 | Beacon et al. |
| 6,013,103 A | 1/2000 | Kaufman et al. |
| 6,019,767 A | 2/2000 | Howell |
| 6,022,377 A | 2/2000 | Nuelle et al. |
| 6,034,296 A | 3/2000 | Elvin et al. |
| 6,056,752 A | 5/2000 | Roger |
| 6,056,754 A | 5/2000 | Haines |
| 6,056,756 A | 5/2000 | Eng et al. |
| 6,080,154 A | 6/2000 | Reay-Young et al. |
| 6,086,592 A | 7/2000 | Rosenberg |
| 6,096,043 A | 8/2000 | Techiera et al. |
| 6,102,952 A | 8/2000 | Koshino |
| 6,113,604 A | 9/2000 | Whittaker et al. |
| 6,126,692 A | 10/2000 | Robie et al. |
| 6,165,142 A | 12/2000 | Bar |
| 6,174,294 B1 | 1/2001 | Crabb et al. |
| 6,447,448 B1 | 9/2002 | Ishikawa et al. |
| 6,488,711 B1 | 12/2002 | Grafinger |
| 6,540,787 B2 | 4/2003 | Biegun et al. |
| 6,553,681 B2 | 4/2003 | Ekholm, Jr. et al. |
| 6,575,980 B1 | 6/2003 | Robie et al. |
| 6,589,283 B1 | 7/2003 | Metzger |
| 6,610,096 B2 | 8/2003 | MacDonald |
| 6,632,225 B2 | 10/2003 | Sanford et al. |
| 6,648,896 B2 | 11/2003 | Overes |
| 6,702,821 B2 | 3/2004 | Bonutti |
| 6,706,005 B2 | 3/2004 | Roy et al. |
| 6,758,850 B2 | 7/2004 | Smith et al. |
| 6,770,078 B2 | 8/2004 | Bonutti |
| 6,821,299 B2 | 11/2004 | Kirking et al. |
| 6,827,723 B2 | 12/2004 | Carson |
| 6,856,834 B2 | 2/2005 | Treppo et al. |
| 6,905,513 B1 | 6/2005 | Metzger |
| 6,923,817 B2 | 8/2005 | Carson |
| 6,972,039 B2 | 12/2005 | Metzger et al. |
| 6,984,249 B2 | 1/2006 | Keller |
| 7,104,996 B2 | 9/2006 | Bonutti |
| 7,153,281 B2 | 12/2006 | Holmes |
| 7,232,416 B2 | 6/2007 | Czernicki |
| 7,275,218 B2 | 9/2007 | Petrella et al. |
| 7,412,897 B2 | 8/2008 | Crottet et al. |
| 7,559,931 B2 | 7/2009 | Stone |
| 7,575,602 B2 | 8/2009 | Amirouche et al. |
| 7,615,055 B2 | 11/2009 | DiSilvestro |
| 7,632,283 B2 | 12/2009 | Heldreth |
| 7,794,499 B2 | 9/2010 | Navarro et al. |
| 7,849,751 B2 | 12/2010 | Clark et al. |
| 7,892,236 B1 | 2/2011 | Bonutti |
| 8,118,815 B2 | 2/2012 | van der Walt |
| 8,211,041 B2 | 7/2012 | Fisher et al. |
| 2001/0021877 A1 | 9/2001 | Biegun et al. |
| 2002/0029045 A1 | 3/2002 | Bonutti |
| 2002/0052606 A1 | 5/2002 | Bonutti |
| 2002/0133175 A1 | 9/2002 | Carson |
| 2002/0147455 A1 | 10/2002 | Carson |
| 2002/0156480 A1 | 10/2002 | Overes et al. |
| 2003/0028196 A1 | 2/2003 | Bonutti |
| 2003/0069591 A1 | 4/2003 | Carson et al. |
| 2003/0069644 A1 | 4/2003 | Kovacevic et al. |
| 2003/0130665 A1 | 7/2003 | Pinczewski et al. |
| 2003/0139645 A1 | 7/2003 | Adelman |
| 2003/0144669 A1 | 7/2003 | Robinson |

(56) References Cited

U.S. PATENT DOCUMENTS

| | | |
|---|---|---|
| 2003/0153978 A1 | 8/2003 | Whiteside |
| 2003/0187452 A1 | 10/2003 | Smith et al. |
| 2003/0236472 A1 | 12/2003 | Van Hoeck et al. |
| 2004/0019382 A1 | 1/2004 | Amirouche et al. |
| 2004/0064073 A1 | 4/2004 | Heldreth |
| 2004/0064191 A1 | 4/2004 | Wasielewski |
| 2004/0097951 A1 | 5/2004 | Steffensmeier |
| 2004/0122441 A1 | 6/2004 | Muratsu |
| 2004/0243148 A1 | 12/2004 | Wasielewski |
| 2005/0010302 A1 | 1/2005 | Dietz et al. |
| 2005/0021044 A1 | 1/2005 | Stone et al. |
| 2005/0038442 A1 | 2/2005 | Freeman |
| 2005/0085920 A1 | 4/2005 | Williamson |
| 2005/0113846 A1 | 5/2005 | Carson |
| 2005/0149041 A1 | 7/2005 | McGinley et al. |
| 2005/0177169 A1 | 8/2005 | Fisher et al. |
| 2005/0177170 A1 | 8/2005 | Fisher et al. |
| 2005/0177173 A1 | 8/2005 | Aebi et al. |
| 2005/0234332 A1 | 10/2005 | Murphy |
| 2005/0234448 A1 | 10/2005 | McCarthy |
| 2005/0234465 A1 | 10/2005 | McCombs et al. |
| 2005/0234466 A1 | 10/2005 | Stallings |
| 2005/0234468 A1 | 10/2005 | Carson |
| 2005/0251026 A1 | 11/2005 | Stone |
| 2005/0261071 A1 | 11/2005 | Cameron |
| 2005/0267485 A1 * | 12/2005 | Cordes et al. ............. 606/88 |
| 2006/0012736 A1 | 1/2006 | Nishino et al. |
| 2006/0081063 A1 | 4/2006 | Neubauer et al. |
| 2006/0149277 A1 | 7/2006 | Cinquin et al. |
| 2006/0161051 A1 | 7/2006 | Terrill-Grisoni et al. |
| 2006/0224088 A1 | 10/2006 | Roche |
| 2006/0241569 A1 | 10/2006 | DiSilvestro |
| 2006/0271056 A1 | 11/2006 | Terrill-Grisoni et al. |
| 2007/0162142 A1 | 7/2007 | Stone |
| 2007/0219561 A1 | 9/2007 | Lavallee et al. |
| 2007/0233144 A1 | 10/2007 | Lavallee et al. |
| 2007/0239165 A1 | 10/2007 | Amirouche |
| 2007/0244488 A1 | 10/2007 | Lakin et al. |
| 2008/0051892 A1 | 2/2008 | Malandain |
| 2008/0133022 A1 | 6/2008 | Caylor |
| 2008/0306413 A1 | 12/2008 | Crottet et al. |
| 2009/0005708 A1 | 1/2009 | Johanson et al. |
| 2009/0018544 A1 | 1/2009 | Heavener |
| 2009/0099570 A1 | 4/2009 | Amiot et al. |
| 2009/0138019 A1 | 5/2009 | Wasielewski |
| 2009/0138021 A1 | 5/2009 | Colquhoun et al. |
| 2009/0270869 A1 | 10/2009 | Colquhoun et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0326544 A1 | 12/2009 | Chessar et al. |
| 2010/0016705 A1 | 1/2010 | Stone |
| 2010/0063508 A1 | 3/2010 | Borja et al. |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0137869 A1 | 6/2010 | Borja et al. |
| 2010/0137871 A1 | 6/2010 | Borja |
| 2010/0198275 A1 | 8/2010 | Chana et al. |
| 2010/0217156 A1 | 8/2010 | Fisher et al. |
| 2010/0250571 A1 * | 9/2010 | Pierce et al. ............. 707/758 |
| 2011/0251694 A1 | 10/2011 | Wasielewski |

FOREIGN PATENT DOCUMENTS

| | | |
|---|---|---|
| EP | 0979636 A2 | 2/2000 |
| EP | 1129676 | 9/2001 |
| EP | 1245193 | 10/2002 |
| EP | 1348382 A2 | 10/2003 |
| EP | 1402857 | 3/2004 |
| EP | 1645229 | 4/2006 |
| EP | 1707159 | 10/2006 |
| EP | 1800616 A1 | 6/2007 |
| EP | 1915951 A2 | 4/2008 |
| EP | 1707159 B1 | 11/2008 |
| EP | 1402857 B1 | 8/2010 |
| EP | 1915951 B1 | 6/2011 |
| WO | 7900739 | 10/1979 |
| WO | 96/17552 A1 | 6/1996 |
| WO | 9617552 A1 | 6/1996 |
| WO | 9935972 | 7/1999 |
| WO | 0078225 A1 | 12/2000 |
| WO | 02071924 A2 | 9/2002 |
| WO | 03065949 A2 | 8/2003 |
| WO | 03084412 A1 | 10/2003 |
| WO | 2004008988 A2 | 1/2004 |
| WO | 2005023120 A1 | 3/2005 |
| WO | 2005089681 A | 9/2005 |
| WO | 2007/036694 A1 | 4/2007 |
| WO | 2007/036699 A1 | 4/2007 |
| WO | 2007036694 A1 | 4/2007 |
| WO | 2007036699 | 4/2007 |
| WO | 2007036699 A1 | 4/2007 |
| WO | 2010/011978 A1 | 1/2010 |
| WO | 2010022272 | 2/2010 |
| WO | 2010022272 A1 | 2/2010 |
| WO | 2010/030809 A1 | 3/2010 |

OTHER PUBLICATIONS

European Search Report, dated Jul. 14, 2006.
Jian Wu et al., "A Method for Widening the Range of Force Management and Gap Adjustment in the Total Knee Replacement," International Conference on BioMedical Engineering and Informatics, 2008, 4 pages.
European Search Report, European Patent Application No. 10156120.7-2201, Jul. 7, 2010, 6 pages.
European Communication pursuance to Article 94(3) EPC, European Patent Application No. 10156105.8-2319, Aug. 1, 2012, 5 pages.
European Search Report, European Patent Application No. 10156132-2201, Jul. 12, 2010, 6 pages.
European Search Report, European Patent Application No. 10156128.0-1526/2237014, Dec. 13, 2012, 6 pages.
European Search Report, European Patent Application No. 10156128.0-1506, Mar. 1, 2013, 11 pages.
European Office Action, European Application No. 10156132.2-2201, Jan. 16, 2013, 4 pages.
European Search Report, European Patent Application No. 10156120.7-2201, dated Jan. 17, 2013, 4 pages.

* cited by examiner

| BALANCE | | LED | | | | |
|---|---|---|---|---|---|---|
| MEDIAL | LATERAL | 80 | 82 | 84 | 86 | 88 |
| <30 | >70 | OFF | OFF | OFF | OFF | ON |
| 35 | 65 | OFF | OFF | OFF | ON | ON |
| 40 | 60 | OFF | OFF | OFF | ON | OFF |
| 45 | 55 | OFF | OFF | ON | ON | OFF |
| 50 | 50 | OFF | OFF | ON | OFF | OFF |
| 55 | 45 | OFF | ON | ON | OFF | OFF |
| 60 | 40 | OFF | ON | OFF | OFF | OFF |
| 65 | 35 | ON | ON | OFF | OFF | OFF |
| >70 | <30 | ON | OFF | OFF | OFF | OFF |

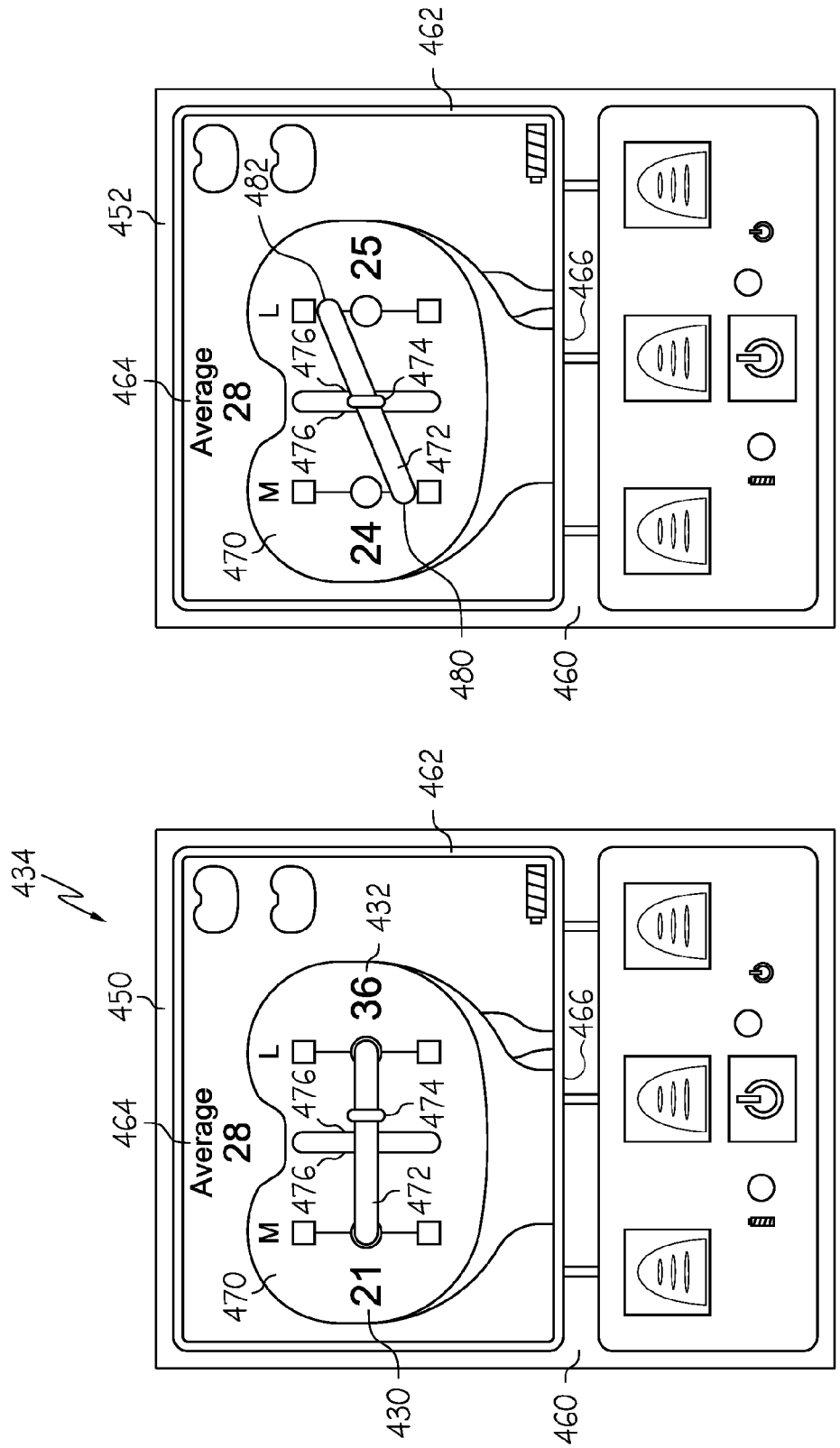

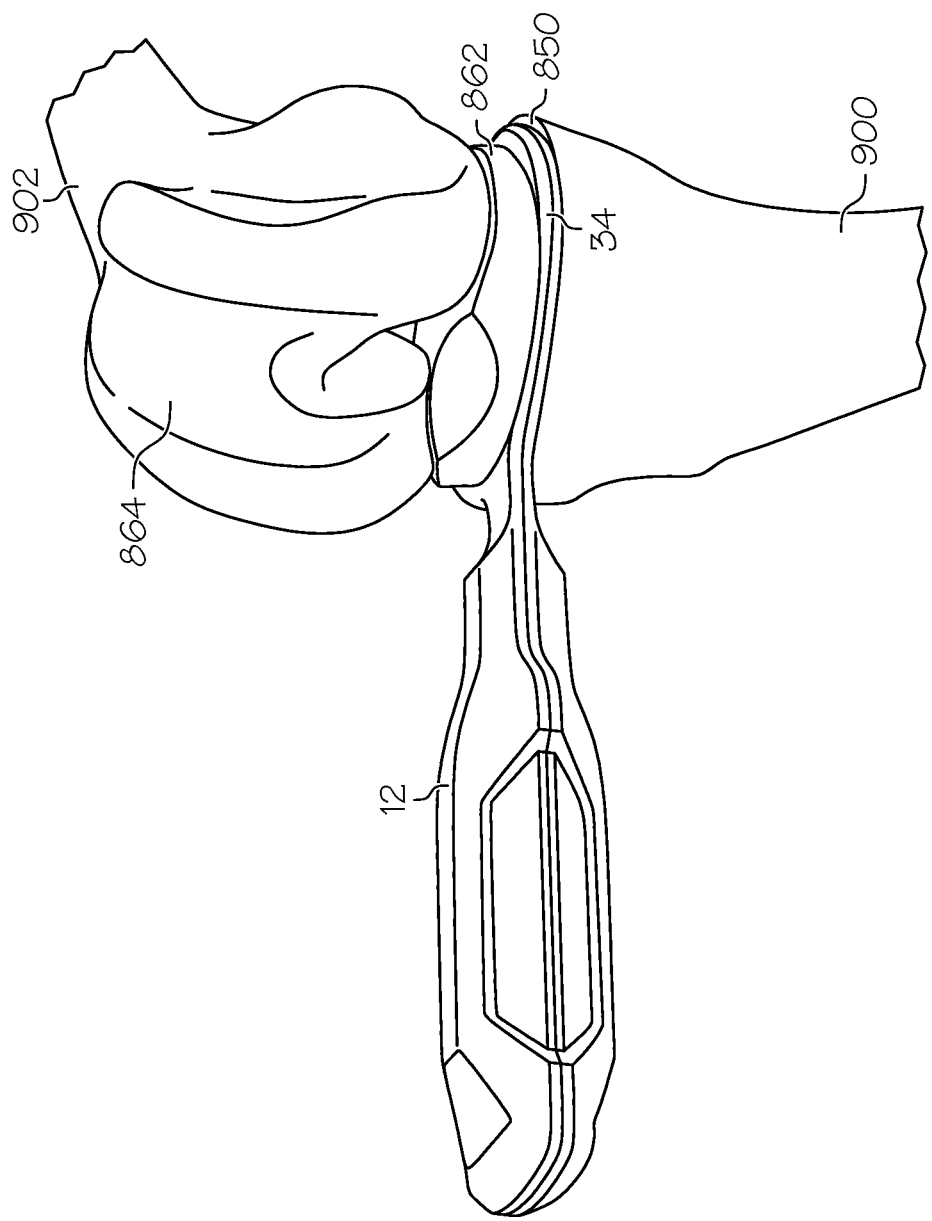

METHOD FOR PERFORMING AN ORTHOPAEDIC SURGICAL PROCEDURE

CROSS-REFERENCE TO RELATED U.S. PATENT APPLICATION

Cross-reference is made to U.S. Utility patent application Ser. No. 12/415,225 entitled "DEVICE AND METHOD FOR DISPLAYING JOINT FORCE DATA" by Jason Sherman, which was filed on Mar. 31, 2009 and issued as U.S. Pat. No. 8,556,830 on Oct. 15, 2013; to U.S. Utility patent application Ser. No. 12/415,172 entitled "DEVICE AND METHOD FOR DETERMINING FORCE OF A KNEE JOINT" by Jason Sherman, which was filed on Mar. 31, 2009 and issued as U.S. Pat. No. 8,551,023 on Oct. 8, 2013; to U.S. Utility patent application Ser. No. 12/415,350 entitled "DEVICE AND METHOD FOR DETERMINING FORCES OF A PATIENT'S JOINT" by Jason Sherman, which was filed on Mar. 31, 2009; and to U.S. Utility patent application Ser. No. 12/415,365 entitled "SYSTEM AND METHOD FOR DISPLAYING JOINT FORCE DATA" by Jason Sherman, which was filed on Mar. 31, 2009 and issued as U.S. Pat. No. 8,597,210 on Dec. 3, 2013; the entirety of each of which is incorporated herein by reference.

TECHNICAL FIELD

The present disclosure relates generally to orthopaedic surgical instruments and, more particularly, to systems, devices, and methods for determining and displaying joint force data.

BACKGROUND

Orthopaedic prostheses are implanted in patients by orthopaedic surgeons to, for example, correct or otherwise alleviate bone and/or soft tissue loss, trauma damage, and/or deformation of the bone(s) of the patients. Orthopaedic prostheses may replace a portion or the complete joint of a patient. For example, the orthopaedic prosthesis may replace the patient's knee, hip, shoulder, ankle, or other joint. In the case of a knee replacement, the orthopaedic knee prosthesis may include a tibial tray, a femoral component, and a polymer insert or bearing positioned between the tibial tray and the femoral component. In some cases, the knee prosthesis may also include a prosthetic patella component, which is secured to a posterior side of the patient's surgically-prepared patella.

During the orthopaedic surgical procedure, a surgeon initially prepares the patient's bone(s) to receive the orthopaedic prosthesis. For example, in the case of a knee replacement orthopaedic surgical procedure, the surgeon may resect a portion of the patient's proximal tibia to which the tibia tray will be attached, a portion of patient's distal femur to which the femoral component will be attached, and/or a portion of the patient's patella to which the patella component will be attached. During such procedures, the surgeon may attempt to balance or otherwise distribute the joint forces of the patient's joint in order to produce joint motion that is similar to the motion of a natural joint. To do so, the surgeon may use surgical experience and manually "feel" for the appropriate joint force balance. Additionally or alternatively, the orthopaedic surgeon may use surgical instruments, such as a ligament balancer in the case of a knee replacement procedure, to assist in the balancing or distributing of joint forces.

In addition, in some surgical procedures such as minimally invasive orthopaedic procedures, surgeons may rely on computer assisted orthopaedic surgery (CAOS) systems to improve the surgeon's ability to see the operative area such as in minimally invasive orthopaedic procedures, to improve alignment of bone cut planes, and to improve the reproducibility of such cut planes. Computer assisted orthopaedic surgery systems assist surgeons in the performance of orthopaedic surgical procedures by, for example, displaying images illustrating surgical steps of the surgical procedure being performed and rendered images of the relevant bones of the patient. Additionally, computer assisted orthopaedic surgery (CAOS) systems provide surgical navigation for the surgeon by tracking and displaying the position of the patient's bones, implants, and/or surgical tools.

SUMMARY

According to one aspect, a method for performing an orthopaedic surgical procedure on a knee joint of a patient may include resecting a proximal end of a patient's tibia to create a resected surface of the patient's tibia and positioning a tibial paddle of a sensor module on the resected surface of the patient's tibia. The tibial paddle may include a sensor array positioned therein. The sensor array may generate sensor signals indicative of a joint force of the patient's knee joint. The method may also include distracting the patient's knee joint while the knee joint is in extension. Additionally, the method may include monitoring a display of the sensor module, which provides a visual indication of the medial-lateral joint force balance of the patient's knee joint. The method may also include performing a balancing procedure to adjust the medial-lateral balance as indicated by the display of the sensor module.

In some embodiments, the method may include distracting the patient's knee joint by positioning a joint distractor in the patient's knee joint such that a medial tibial paddle of the joint distractor and a lateral tibial paddle of the joint distractor each contact the tibial paddle of the sensor module. Additionally, the method may include coupling the sensor module to the joint distractor. The method may also include moving a medial femoral paddle of the joint distractor away from a corresponding medial tibial paddle of the joint distractor medial femoral paddle and moving a lateral femoral paddle of the joint distractor away from a corresponding lateral medial paddle of the joint distractor. For example, the method may include establishing a substantially rectangular gap between the patient's proximal tibia and a distal femur.

In some embodiments, the method may include positioning a spacer block on the tibial paddle of the sensor module. Additionally, the method may include performing a balancing procedure comprises performing a ligament release on the patient's soft tissue. Further, in some embodiments, the method may include positioning the knee joint in flexion and distracting the knee joint in flexion to a predetermined medial-lateral balance value by monitoring the display of the sensor module. Additionally, the method may include performing a number of resectioning cuts on the distal end of the patient's femur while the knee joint is distracted in flexion. In such embodiments, the method may include positioning a joint distractor in the patient's knee joint such that a medial tibial paddle of the joint distractor and a lateral tibial paddle of the joint distractor each contact the tibial paddle of the sensor module. Such method may also include coupling the sensor module to the joint distractor.

According to another aspect, a method for performing an orthopaedic surgical procedure on a knee joint of a patient may include resecting a proximal end of a patient's tibia to create a resected surface of the patient's tibia and positioning a tibial paddle of a sensor module on the resected surface of the patient's tibia. The tibial paddle may include a sensor array positioned therein. The sensor array may generate sensor signals indicative of a joint force of the patient's knee joint. The method may also include distracting the patient's knee joint to establish a substantially rectangular gap between the patient's proximal tibia and distal femur. Additionally, the method may include monitoring a visual indication of the relative balance of a medial joint force and a lateral joint force of the patient's knee joint displayed on the display of the sensor module and performing a balancing procedure on the patient's knee joint until the medial joint force and the lateral joint force are within a first predetermined percentage of each other as indicated on the visual indication displayed on the display module.

In some embodiments, the method may include positioning a joint distractor in the patient's knee joint such that a medial tibial paddle of the joint distractor and a lateral tibial paddle of the joint distractor each contact the tibial paddle of the sensor module. Additionally, the method may include coupling the sensor module to the joint distractor. The method may further include moving a medial femoral paddle of the joint distractor away from a corresponding medial tibial paddle of the joint distractor medial femoral paddle and moving a lateral femoral paddle of the joint distractor away from a corresponding lateral medial paddle of the joint distractor.

Additionally, in some embodiments, the method may include positioning a spacer block on the tibial paddle of the sensor module. The method may also include performing a ligament release on the patient's soft tissue. The method may further include positioning the knee joint in flexion and distracting the knee joint in flexion until the medial joint force and the lateral joint force are within a second predetermined percentage of each other as indicated on the visual indication displayed on the display module. Additionally, the method may performing a number of resectioning cuts on the distal end of the patient's femur while the knee joint is distracted in flexion.

According to further aspect, a method for performing an orthopaedic surgical procedure on a knee joint of a patient may include positioning a tibial paddle of a sensor module on a resected proximal end of a patient's tibia. The tibial paddle may include a sensor array positioned therein. The sensor array may generate sensor signals indicative of a joint force of the patient's knee joint. The method may also include distracting the patient's knee joint to establish a substantially rectangular gap between the patient's proximal tibia and distal femur. Additionally, the method may include monitoring a plurality of light emitting diodes located on the sensor module. The plurality of light emitting diodes may be illuminated in a pattern to provide a visual indication of the relative balance of a medial joint force and a lateral joint force of the patient's knee joint displayed on the display of the sensor module. The method may further include performing a ligament release procedure on the patient's knee joint until the medial joint force and the lateral joint force are within a first predetermined percentage of each other as indicated by the plurality of light emitting diodes.

BRIEF DESCRIPTION OF THE DRAWINGS

The detailed description particularly refers to the following figures, in which:

FIGS. 24-26 are illustrative screenshots that may be displayed to a user on the display module of FIG. 20;

FIG. 41 is another perspective view of a patient's joint in flexion during an orthopaedic surgical procedure using the sensor module of FIG. 2.

DETAILED DESCRIPTION OF THE DRAWINGS

Figure 1:
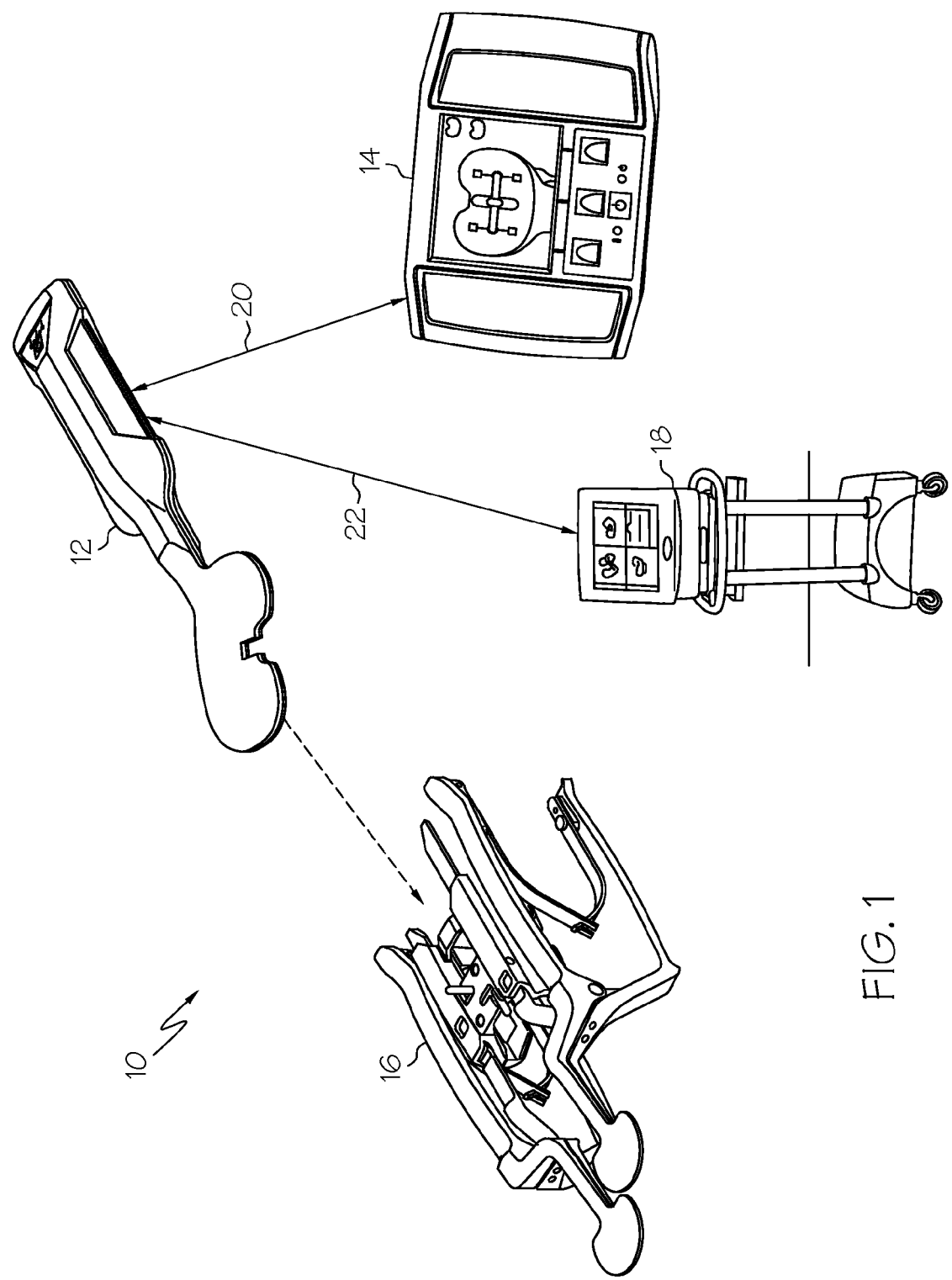
FIG. 1 is a simplified diagram of one embodiment of a system for measuring and displaying joint force data of a patient's joint.
Figure 2:
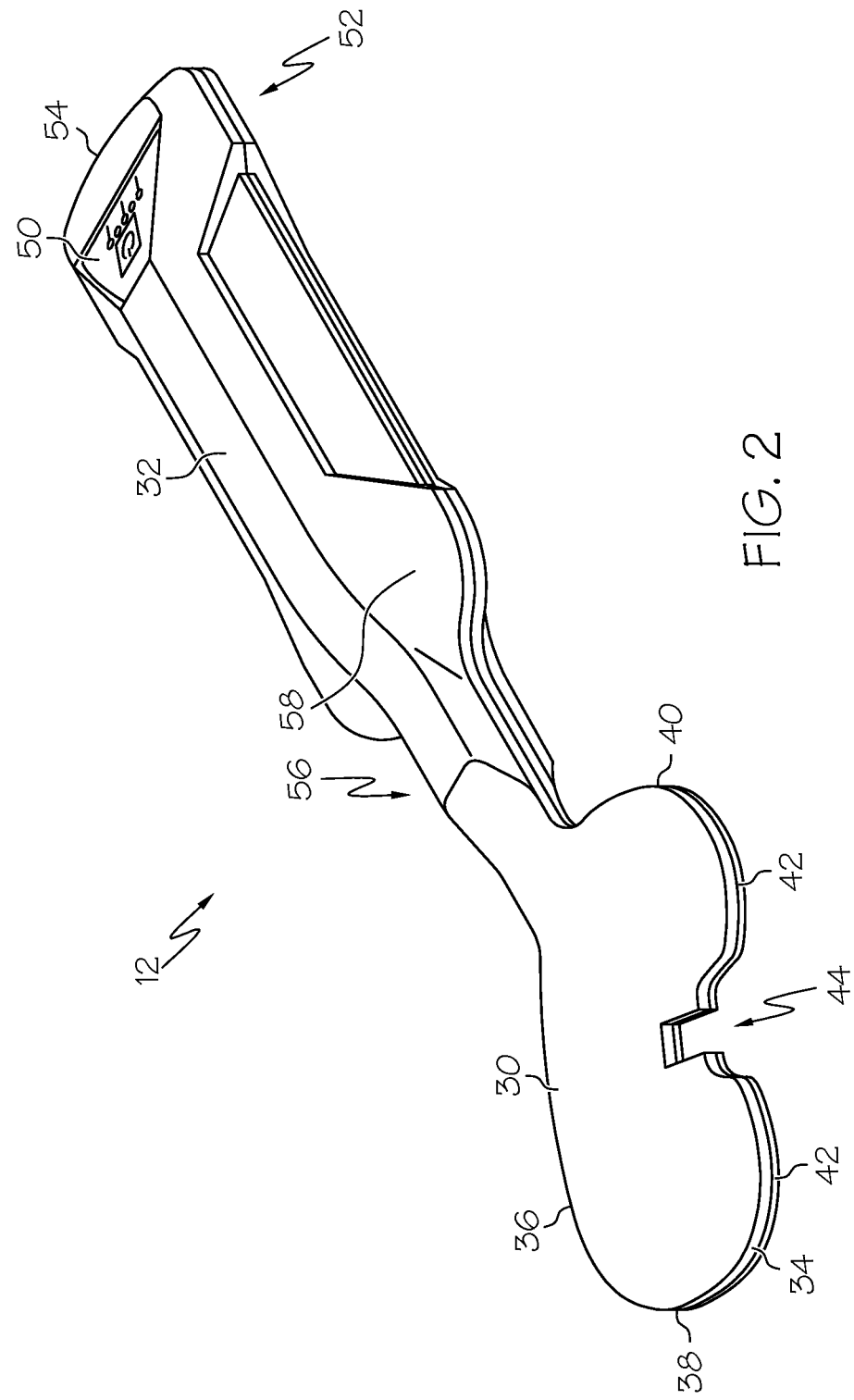
FIG. 2 is a perspective view of one embodiment of a sensor module of the system of FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, in one embodiment, a system 10 for determining and displaying joint forces of a patient's joint during an orthopaedic surgical procedure includes a sensor module 12, a hand-held display module 14, and a joint distractor 16. The system 10 may also includes a computer assisted surgery system (CAOS) system 18 in some embodiments. As discussed in more detail below, the sensor module 12 is configured to be inserted into a patient's joint and provide a visual indication of the joint forces to an orthopaedic surgeon. For example, in one illustrative embodiment, the sensor module 12 provides a visual indication of the relative or balance of the medial-lateral joint forces of a patient's knee joint. The sensor module 12 may also be configured to transmit joint force data to the hand-held display module 14 via a wireless communication link 20 and/or the computer assisted surgery system 18 via a wireless communication link 22. In response, the display module 14 and/or computer assisted surgery system 18 are configured to display the joint force data, or data derived therefrom, to an orthopaedic surgeon. Additionally, during the performance of an orthopaedic surgical procedure, such as a total or partial knee arthroplasty procedure, the sensor module 12 may be coupled to the joint distractor 16 to provide visual indication of the joint forces of the patient's joint during distraction thereof as discussed below.

Referring now to FIGS. 2-10, the sensor module 12 includes a sensor housing 30 and a handle 32 coupled to the sensor housing 30. The sensor housing 30 is sized and shaped to be positioned in a joint of the patient. In the illustrative embodiment, the sensor housing 30 is embodied as a tibial paddle 34, which is shaped to be positioned in a knee joint of the patient. However, the sensor housing 30 may be configured to be used with other joints of the patient in other embodiments as discussed in more detail below in regard to FIGS. 11 and 12.

In use, the tibial paddle 34 is configured to be positioned on a proximal plateau of a patient's resected tibia (see, e.g., FIG. 29-33). As discussed in more detail below, the tibial paddle 34 may be placed in contact with the patient's tibia or may be placed on an intervening platform or other member. Additionally, the sensor module 12 may be used on the patient's left or right knee. For example, the sensor module 12 may be used on a patient's left knee via a medial surgical approach wherein the tibial paddle 34 is inserted into the patient's left knee joint via a medial capsular incision. In such position, as discussed below, the handle 32 extends out of the medial capsular incision. Alternatively, by simply flipping or turning over the sensor module 12, the module 12 may be used on the patient's left knee via a lateral surgical approach wherein the tibial paddle 34 is inserted into the patient's left knee joint via a lateral capsular incision. Again, in such position, the handle 32 extends out of the lateral capsular incision.

As such, it should be appreciated that sensor module 12 may be used on the patient's left or right knee using a medial or lateral surgical approach. For clarity of description, the sensor module 12 and the system 10 are described below with reference to an orthopaedic surgical procedure using a medial surgical approach (i.e., using a medial capsular incision to access the patient's joint). However, it should be appreciated that such description is equally applicable to lateral surgical approach procedures. As such, some structures are described using particular anatomical references (e.g., lateral and medial) with the understanding that such references would be flipped or switched when the module 12 is used in a lateral surgical approach procedure. For example, a "medial side" of the tibial paddle 34 becomes a "lateral side" of the tibial paddle 34 when used in a lateral surgical approach procedure.

The tibial paddle 34 is substantially planar and has a shape generally corresponding to the shape of the orthopaedic prosthesis to be implanted in the patient. For example, in the illustrative embodiment, the tibial paddle 34 has a shape generally corresponding to a knee prosthesis of a particular size. However, in other embodiments as discussed in more detail below, the paddle 34 (or sensor housing 30) may have a shape generally corresponding to other types of orthopedic prostheses such as a hip prosthesis, a shoulder prosthesis, an ankle prosthesis, a spine prosthesis, or a patella prosthesis.

The illustrative tibial paddle 34 includes a curved anterior side 36, a curved lateral side 38, a curved medial side 40, and a curved posterior side 42, each shaped to approximate the shape a tibial bearing of an orthopaedic knee prosthesis. Again, as discussed above, the lateral side 38 and the medial side 40 are lateral and medial sides, respectively, in those embodiments wherein the sensor module 12 is used in a lateral surgical approach procedure. The posterior side 42 includes a posterior notch 44 to allow the tibial paddle 34 to be positioned around the soft tissue of the patient's joint such as the posterior cruciate ligament. Additionally, in some embodiments, the posterior notch 44 may also provide a mount for other surgical devices such as a trail post for rotating mobile bearing trails. Further, in some embodiments, the posterior notch 44 may be extended or otherwise have other configurations so as to provide a mount for other orthopaedic surgical devices such as fixed and/or mobile tibial trials or the like.

The overall size of the tibial paddle 34 may be selected based on the particular anatomical structure of the patient. For example, in some embodiments, the tibial paddle 34 may be provided in various sizes to accommodate patients of varying sizes. It should be appreciated that the general shape and size of the paddle 34 (and sensor housing 30) is designed and selected such that the paddle 34 or housing 30 does not significantly overhang with respect to the associated bony anatomy of the patient such that the paddle 34 or housing 30 nor adversely impinge the surrounding soft tissue.

The handle 32 includes a pair of displays 50, 52 coupled to a first end 54 of the handle 32. A second end 56 of the handle 32 opposite the first end 54 is coupled to the tibial paddle 34. In the illustrative embodiment of FIG. 2, the handle 32 and tibial paddle 34 are substantially monolithic in structure. However, in other embodiments, the tibial paddle 34 may be removably coupled to the handle 32 via a suitable connector or the like.

Figure 3:
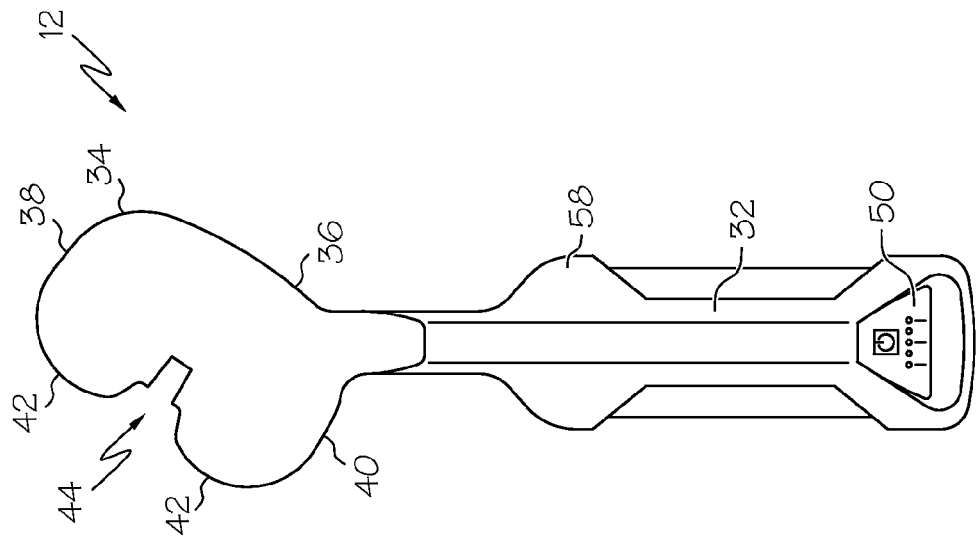
FIG. 3 is a plan view of a top side of the sensor module of FIG. 2.
Figure 4:
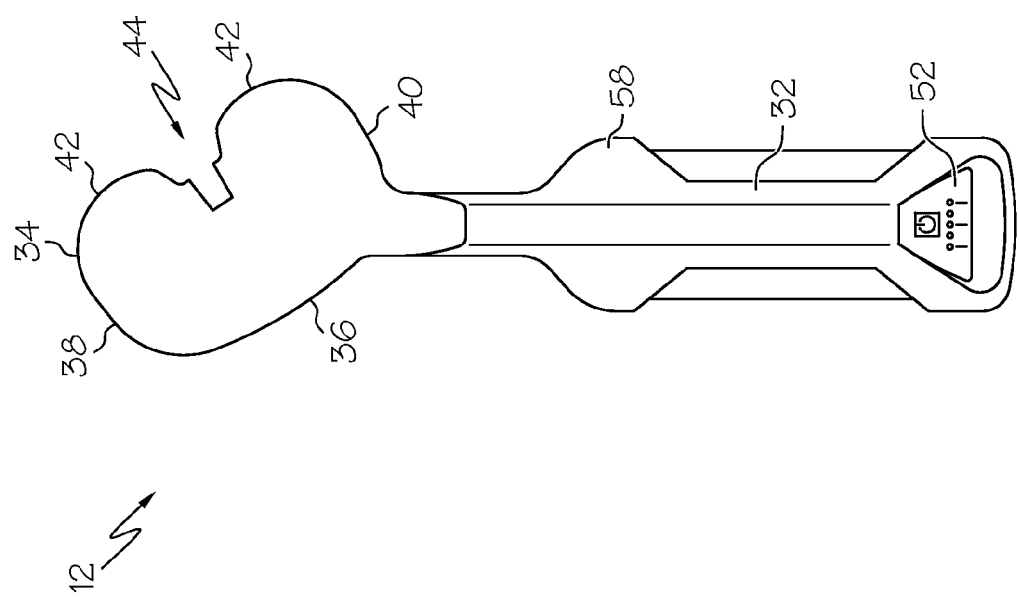
FIG. 4 is a plan view of a bottom side of the sensor module of FIG. 2.

As illustrated in FIGS. 3 and 4, the handle 32 extends from a side of the tibial paddle 34. In the illustrative embodiment, the handle 32 extends from the medial side 40 (which is a lateral side when the sensor module 12 is used in a lateral surgical approach procedure). It should be appreciated that because the handle 32 extends from a side of the paddle 34, the tibial paddle 34 may be positioned in a knee joint of a patient without the need to sublux or evert the patient's patella. That is, the tibial paddle 34 may be properly positioned between the patient's proximal tibia and distal femur with the patient's patella in the natural position.

Depending on the particular surgical approach to be used by the orthopedic surgeon, the surgeon may flip the sensor module 12 to the proper orientation such that the tibial paddle 34 is inserted into the patient's knee joint through the associated capsular incision. In either orientation, the handle 32 extends out of the capsular incision and at least one of the displays 50, 52 is visible to the orthopaedic surgeon. For example, if the orthopaedic surgeon is using a medial surgical approach on a patient's left knee, the orthopaedic surgeon may position the sensor module 12 in the orientation illustrated in FIG. 3 such that the handle 32 extends from the medial side of the patient's knee (through the medial capsular incision) when the tibial paddle 34 is inserted into the knee joint and the display 50 is visible to the surgeon. Alternatively, if the orthopaedic surgeon is using a lateral surgical approach on a patient's left knee, the orthopaedic surgeon may position the sensor module 12 in the orientation illustrated in FIG. 4 such that the handle 32 extends from the lateral side of the patient's knee (through the lateral capsular incision) when the tibial paddle 34 is inserted into the knee joint and the display 52 is visible to the surgeon.

As discussed above, the sensor module 12 is configured to assist a surgeon during the performance of an orthopaedic surgical procedure. As such, the sensor module 12 includes an outer housing 58 formed from a bio-compatible material. For example, the outer housing 58 may be formed from a bio-compatible plastic or polymer. In one particular embodiment, the sensor module 12 is configured for single-usage and, as such, is provided in a sterile form. For example, the sensor module 12 may be provided in a sterile packaging. However, in those embodiments wherein the tibial paddle 34 is removably coupled to the handle 32, the tibial paddle 34 may be designed for single-usage and the handle 32 may be configured to be reusable via an autoclaving procedure or the like.

Figure 5:
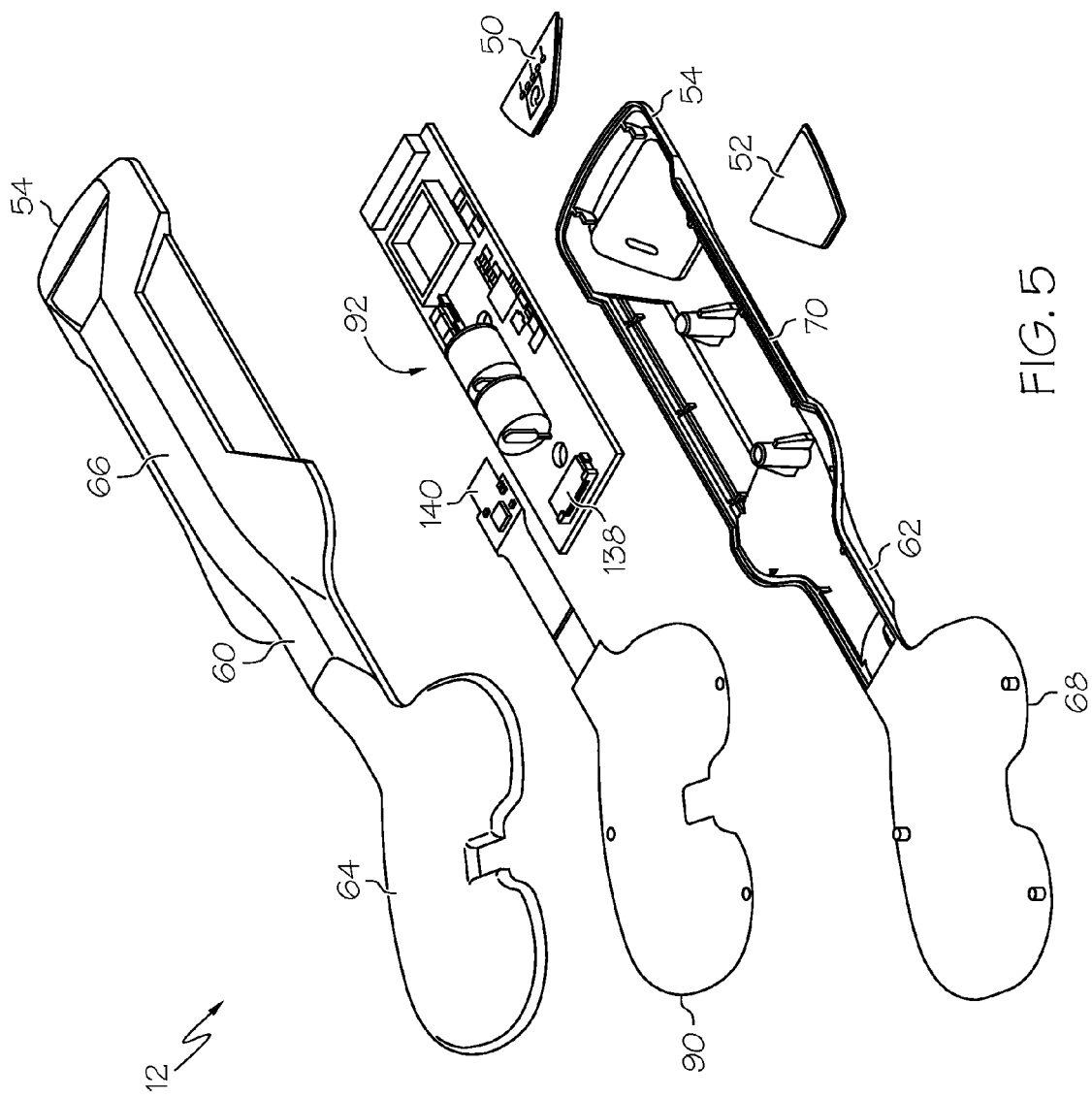
FIG. 5 is an exploded, perspective view of the sensor module of FIG. 2.

As illustrated in FIG. 5, the outer housing 58 of the sensor module 12 includes an upper housing 60 and a lower housing 62, which are coupled to each other. In some embodiments, the upper housing 60 and the lower housing 62 are mirror images of each other. The upper housing 60 includes an upper tibial paddle housing 64 and an upper handle housing 66. Similarly, the lower housing 62 includes a lower tibial paddle housing 68 and a lower handle housing 70.

Figures 6, 7:
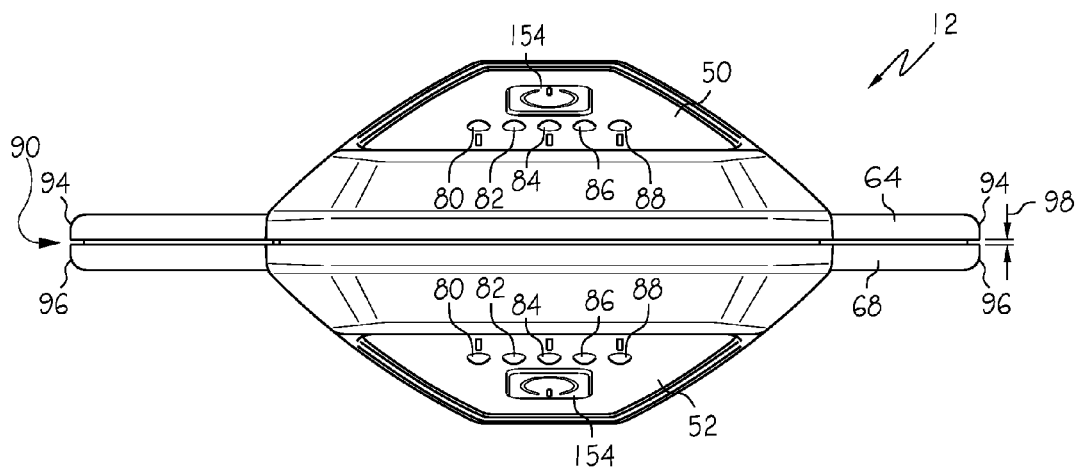
FIG. 6 is an elevation view of an end of the sensor module of FIG. 2.
FIG. 7 is a graph of one embodiment of a display protocol for the displays of the sensor module of FIG. 2.

The display 50 is coupled to the end 54 of the upper housing 60 and the display 52 is coupled to the 54 of the lower housing 62. As illustrated in FIG. 6, the displays 50, 52 are illustratively embodied as arrays of light emitting diodes. However, in other embodiments, the displays 50, 52 may be embodied as other types of displays such as liquid crystal displays, segmented displays, and/or the like. In the illustrative embodiment of FIG. 6, each of the displays 50, 52 includes five separate light emitting diodes 80, 82, 84, 86, 88. As discussed in more detail below, the central light emitting diodes 84 are illuminated when the medial-lateral joint forces of the patient's knee joint are approximately equal. Additionally, the light emitting diodes 80 and/or 82 are illuminated when the medial joint force is greater than the lateral joint force of the patient's knee joint by a predetermined threshold amount and the light emitting diodes 86 and 88 are illuminated when the lateral joint force is greater than the medial joint force of the patient's knee by the predetermine threshold amount (again, assuming a medial surgical approach). As shown in FIG. 6, the light emitting diodes 80, 82, 84, 86, 88 of the displays 50, 52 are arranged such that the light emitting diodes 80, 82 correspond with the medial side 40 of the tibial paddle 34 and the light emitting diodes 86, 88 correspond with the lateral side 38 of the tibial paddle 34 regardless of the orientation (i.e., regardless of whether the upper housing 60 or the lower housing 62 is facing upwardly).

As discussed in more detail below, the light emitting diodes 80, 82, 84, 86, 88 may be illuminated according to a predetermined display protocol to provide a visual indication to the surgeon of the relative medial-lateral joint force balance. By activating or illuminating one or more of the light emitting diodes 80, 82, 84, 86, 88, an orthopaedic surgeon may visual determine which side of the patient's joint is exerting a greater amount of force and the general magnitude of such force relative to the opposite side of the patient's joint. For example, one illustrative display protocol is presented in graph 170 in FIG. 7. According to the illustrative display protocol 170, only the light emitting diode 88 is illuminated if the medial-lateral joint force balance is 30% medial-70% lateral, respectively, or laterally greater. However, both light emitting diodes 86 and 88 are illuminated if the medial-lateral joint force balance is about 35% medial-65% lateral, respectively. If the medial-lateral joint force balance is about 40% medial-60% lateral, respectively, only the light emitting diode 86 is illumined. If the medial-lateral joint force balance is about 45% medial-55% lateral, respectively, both light emitting diodes 84 and 86 are illuminated. If the medial-lateral joint force balance is about 50% medial-50% lateral, only the light emitting diode 84 is illumined. If the medial-lateral joint force balance is about 55% medial-45% lateral, respectively, both light emitting diodes 82 and 84 are illuminated. If the medial-lateral joint force balance is about 60% medial-40% lateral, respectively, only the light emitting diode 82 is illumined. If the medial-lateral joint force balance is about 65% medial-35% lateral, respectively, both light emitting diodes 80 and 82 are illuminated. Additionally, if the medial-lateral joint force balance is 70% medial-30% lateral, respectively, or medially greater, only the light emitting diode 80 is illuminated. In this way, a visual indication of the relative joint force balance of the patient's knee is provided to the orthopaedic surgeon. Of course, in other embodiments, other display protocols may be used to control and illuminate the displays 50, 52.

The sensor module 12 includes a sensor array 90 positioned in the tibial paddle 34 and communicatively coupled to a control circuit 92 positioned in the handle 32. The sensor array 90 is "sandwiched" between the upper housing piece 60 and the lower housing piece 62. However, the upper housing piece 60 and the lower housing piece 62 are spaced apart to allow the sensor array 90 to be compressed by the joint force applied to the tibial paddle 34. For example, as illustrated in FIG. 6, the upper housing 64 includes an outer rim 94 and the lower housing 68 includes an outer rim 96, which is spaced apart from the outer rim 94 of the upper housing 64 by a distance 98. When a joint force is applied to the tibial paddle 34, the outer rims 94, 96 are moved toward each as the sensor array 90 is compressed.

Figure 8:
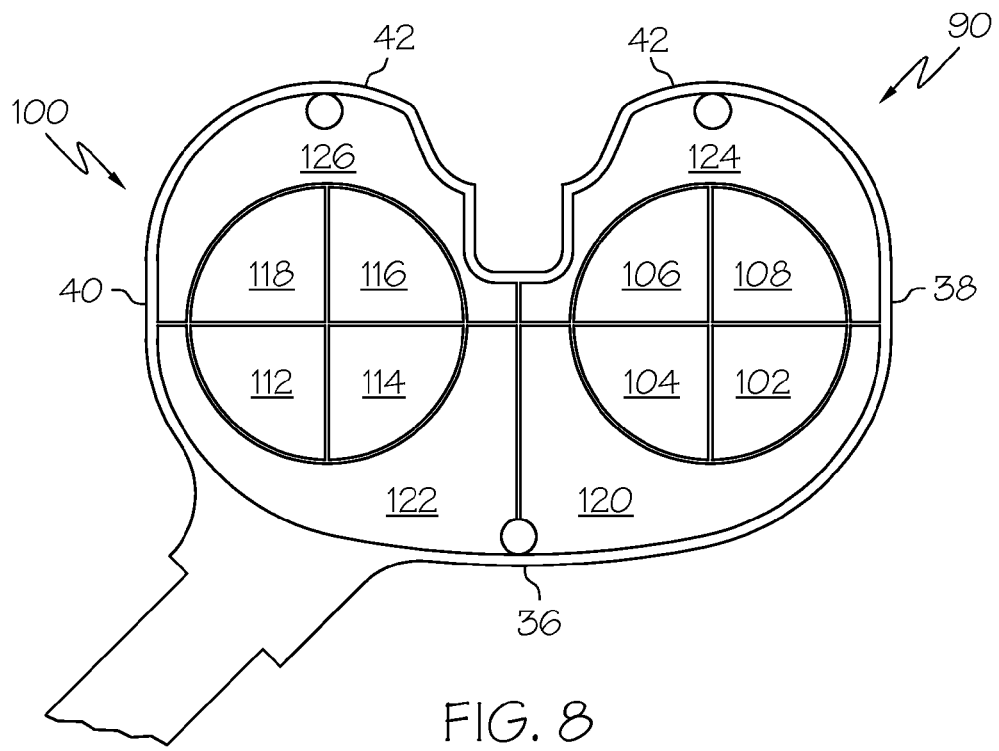
FIG. 8 is a simplified diagram of one embodiment of a sensor array of the sensor module of FIG. 2.
Figure 27:
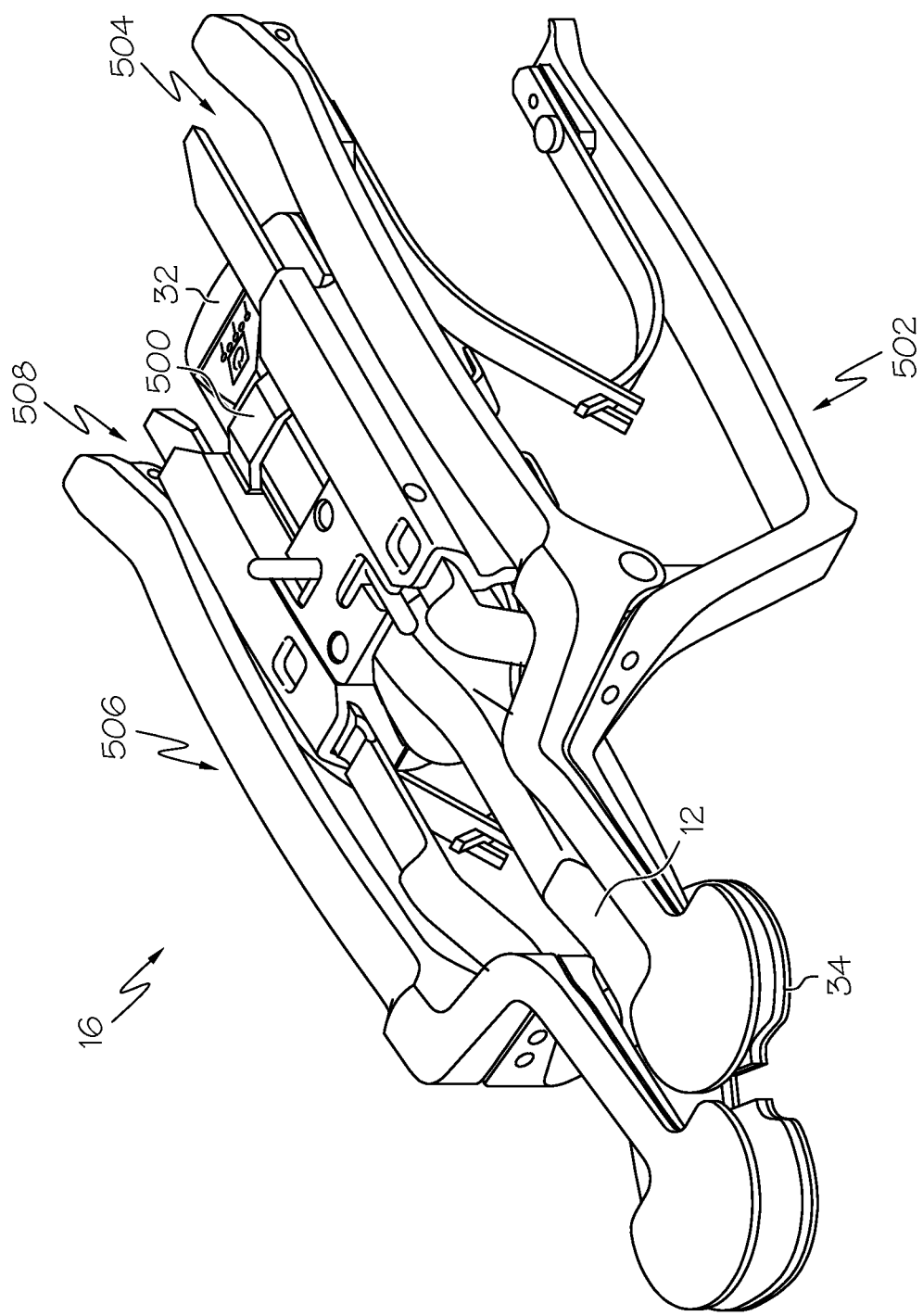
FIG. 27 is a perspective view of one embodiment of a joint distactor of the system of FIG. 1 having the sensor module of FIG. 2 coupled therewith.

The sensor array 90 includes a plurality of pressure sensors or sensor elements 100 (see FIGS. 8 and 9) configured to generate sensor signals indicative of the joint force applied to the sensor array 90. In the illustrative embodiment, the pressure sensors 100 are embodied as capacitive pressure sensors, but may be embodied as other types of sensors in other embodiments. In the illustrative embodiment, the pressure sensors 100 of the sensor array 90 are arranged in a particular configuration. For example, in one embodiment as illustrated in FIG. 8, the sensor array 90 includes a set of pressure sensors 102, 104, 106, 108 arranged in a substantially circular pattern and positioned toward the medial side 38 of the tibial paddle 34. Additionally, the sensor array 90 includes a set of pressure sensors 112, 114, 116, 118 arranged in a substantially circular pattern and positioned toward the lateral side 40 of the tibial paddle 34. The sensor array 90 also includes a pressure sensor 120 positioned toward the anterior side 36 and medial side 38 of the tibial paddle 34 and a pressure sensor 122 positioned toward the anterior side 36 and lateral side 40 of the tibial paddle 34. Additionally, the sensor array 90 includes a pressure sensor 124 positioned toward the posterior side 42 and medial side 38 of the tibial paddle 34 and a pressure sensor 126 positioned toward the posterior side 42 and lateral side 40 of the tibial paddle 34. Of course, in other embodiments, sensor arrays having pressure sensors arranged in other configurations may be used. In the illustrative embodiment, the pressure sensors 102, 104, 106, 108 and 112, 114, 116, 118 are arranged in a pattern corresponding to the shape and size of a tibial paddle of the distractor 16 to improve sensitivity thereto as illustrated in and described below in regard to FIG. 27.

The pressure sensors 102, 104, 108, 106, 120, 124 form a medial set of pressure sensors that generate sensor signals indicative of a medial joint force component of the joint force of a patient's knee (again, assuming a medial surgical approach). Similarly, the pressure sensors 112, 114, 118, 116, 122, 124 form a lateral set of pressure sensors that generate sensor signals indicative of a lateral joint force component of the joint force of a patient's knee. Additionally, pressure sensors 102, 104, 120 form an anterior-medial set of pressure sensors that generate sensor signals indicative of an anterior-medial joint force component of the joint force of a patient's knee. Similarly, the pressure sensors 112, 114, 122 form an anterior-lateral set of pressure sensors that generate sensor signals indicative of an anterior-lateral joint force component of the joint force of a patient's knee. The pressure sensors 106, 108, 124 form a posterior-medial set of pressure sensors that generate sensor signals indicative of a posterior-medial joint force component of the joint force of a patient's knee.

Similarly, the pressure sensors 116, 118, 126 form a posterior-lateral set of pressure sensors that generate sensor signals indicative of a posterior-lateral joint force component of the joint force of a patient's knee.

Figure 9:
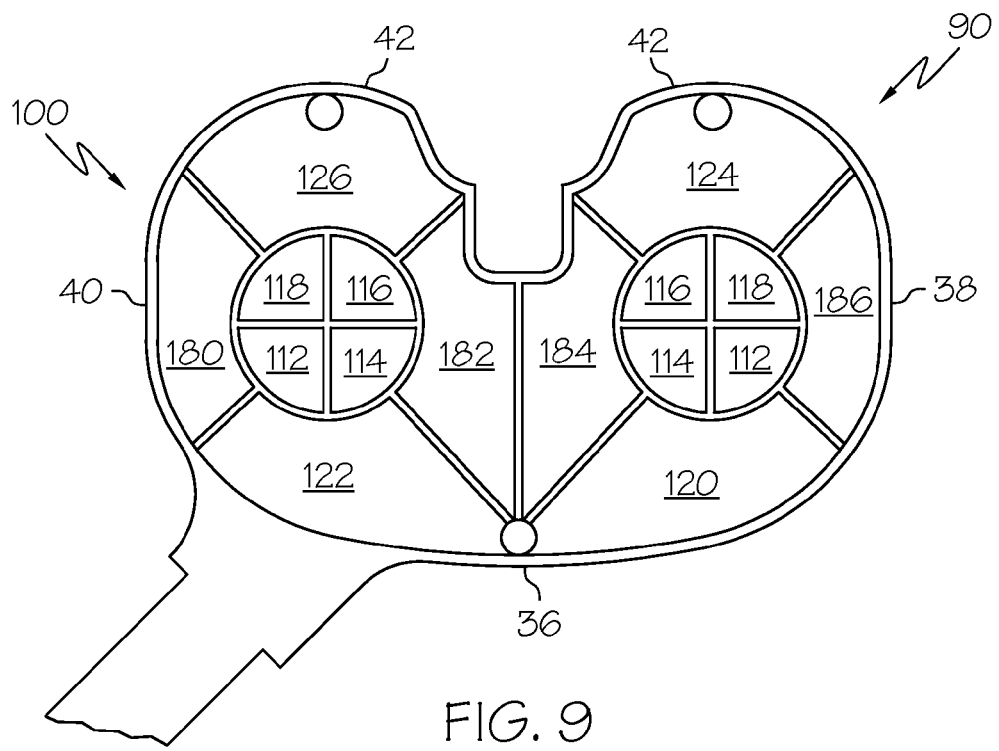
FIG. 9 is a simplified diagram of another embodiment of the sensor array of the sensor module of FIG. 2.

In other embodiments, the sensor array 90 may include more or fewer pressure sensors. In one particular embodiment, the sensor array 90 may include additional medial and lateral pressure sensors for each condyle of the patient's femur. For example, as illustrated in FIG. 9, the sensor array 90 may include a medial-medial pressure sensor 180, a medial-lateral pressure sensor 182, a lateral-medial pressure sensor 184, and lateral-lateral pressure sensor 186. That is, the pressure sensor 180 is configured to sense or measure the medial component of the medial joint force exerted by the patient's medial femoral condyle. Similarly, the pressure sensor 182 is configured to sense or measure the lateral component of the medial joint exerted by the patient's medial femoral condyle. The pressure sensor 184 is configured to sense or measure the medial component of the lateral joint force exerted by the patient's lateral femoral condyle. Similarly, the pressure sensor 186 is configured to sense or measure the lateral component of the lateral joint exerted by the patient's lateral femoral condyle. The particular shape and size of the pressure sensors 180, 182, 184, 186 may be selected based on size, shape, and positioning of the other pressure sensors of the sensor array 90.

Figure 10:
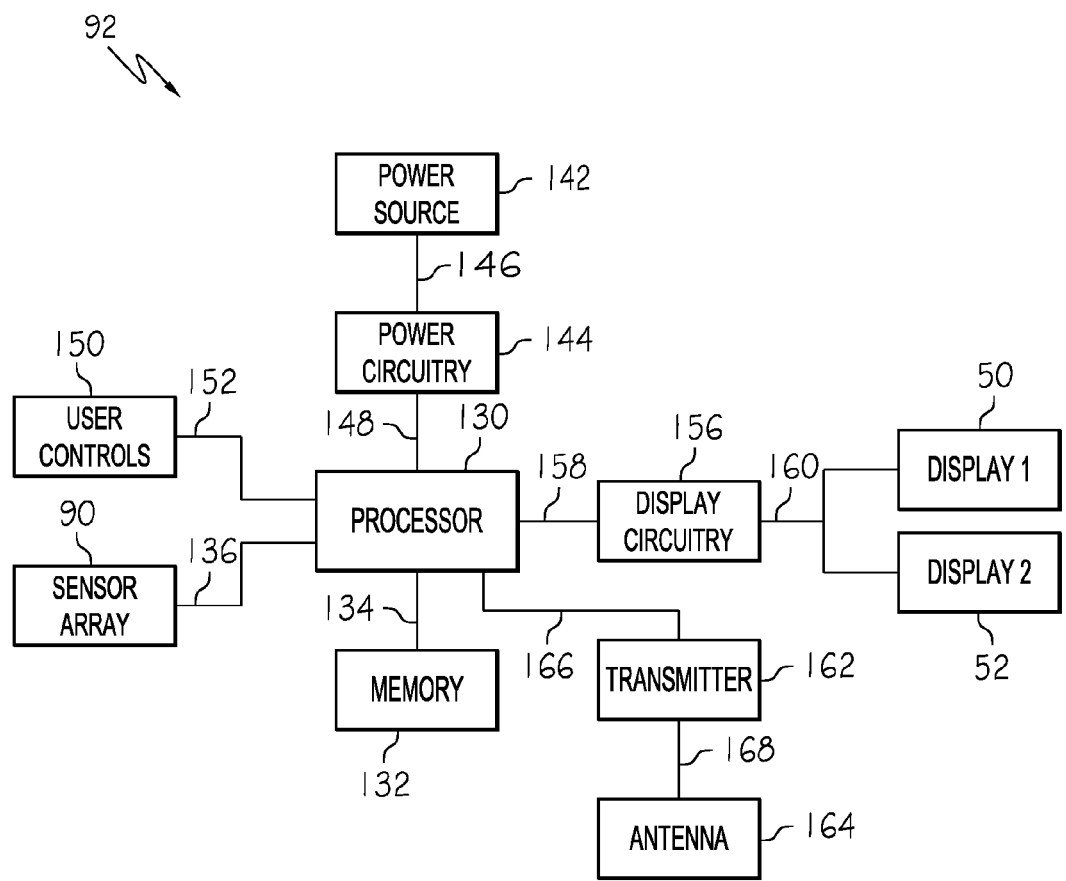
FIG. 10 is a simplified block diagram of one embodiment of an electrical circuit of the sensor module of FIG. 2.

Referring now to FIG. 10, the control circuit 92 includes a processor 130 and a memory device 132. The processor 130 may be embodied as any type of processor configured to perform the functions described herein. For example, the processor 130 may be embodied as a separate integrated circuit or as a collection of electronic devices. Additionally, the processor may be a single or multi-core processor. Although only a single processor 130 is illustrated in FIG. 10, it should be appreciated that in other embodiments, the control circuit 92 may include any number of additional processors. The memory device 132 may be embodied read-only memory devices and/or random access memory devices. For example, the memory device 132 may be embodied as or otherwise include electrically erasable programmable read-only memory devices (EEPROM), dynamic random access memory devices (DRAM), synchronous dynamic random access memory devices (SDRAM), double-data rate dynamic random access memory devices (DDR SDRAM), and/or other volatile or non-volatile memory devices. Additionally, although only a single memory device is illustrated in FIG. 10, in other embodiments, the control circuit 92 may include additional memory devices.

The processor 130 is communicatively coupled to the memory device 132 via signal paths 134. The signal paths 134 may be embodied as any type of signal paths capable of facilitating communication between the processor 130 and the memory device 132. For example, the signal paths 134 may be embodied as any number of wires, printed circuit board traces, via, bus, intervening devices, and/or the like. The processor 130 is also communicatively coupled to the sensor array 90 via signal paths 136. Similar to signal paths 134, the signal paths 136 may be embodied as any type of signal paths capable of facilitating communication between the processor 130 and the sensor array 90 including, for example any number of wires, printed circuit board traces, via, bus, intervening devices, and/or the like. Additionally, the signal path 136 may include a connector 138 (see FIG. 5) configured to receive a plug-end 140 of the sensor array 90.

The control circuit 92 also includes a power source 142 and associated power control circuitry 144. The power source 142 may be embodied as a number of batteries sized to fit in the sensor module 12. The power source 142 is electrically coupled to the power control circuitry 144 via signal paths 146 and the power control circuitry 144 is electrically coupled to the processor 130 and other devices of the control circuit 92 via signal paths 148. The signal paths 146, 148 may be embodied as any type of signal paths including, for example any number of wires, printed circuit board traces, via, bus, intervening devices, and/or the like. The power circuitry 144 may include power control, distribution, and filtering circuitry and is configured to provide or distribute power from the power source 142 to the processor 130 and other devices or components of the control circuit 92.

The control circuit 92 also includes user controls 150 communicatively coupled to the processor 130 via signal paths 152. The user controls 150 are embodied as power buttons 154 (see FIG. 6) located on the displays 50, 52 and selectable by a user to turn the sensor module 12 on. However, in the illustrative embodiment, the control circuit 92 is configured to prevent or otherwise limit the ability of the user from turning off the sensor module 12 via the power buttons 154 or other controls after the sensor module 12 has been turned on. That is, once turned on, the control circuit 92 is configured to remain on until the power source 142 is depleted. Such a configuration ensures that the sensor module 12 is used during a single orthopaedic surgical procedure and is not otherwise reusable in multiple procedures.

The signal paths 152 are similar to the signal paths 134 and may be embodied as any type of signal paths capable of facilitating communication between the user controls 150 and the processor 130 including, for example any number of wires, printed circuit board traces, via, bus, intervening devices, and/or the like.

The control circuit 92 also includes display circuitry 156 for driving and/or controlling the displays 50, 52. The display circuitry 156 is communicatively coupled to the processor 130 via signal paths 158 and to the displays 50, 52 via signal paths 160. Similar to the signal paths 134 discussed above, the signal paths 158, 160 may be embodied as any type of signal paths capable of facilitating communication between the processor 130 and display circuitry 156 and the display circuit 156 and displays 50, 52, respectively. For example, the signal paths 158, 160 may be embodied as any number of wires, printed circuit board traces, via, bus, intervening devices, and/or the like. As discussed above, in the illustrative embodiment, the displays 50, 52 are embodied as an arrangement of light emitting diodes 80, 82, 84, 86, 88.

In some embodiments, the sensor module 12 is configured to transmit force data to the display module 14 and/or computer assisted orthopaedic surgery (CAOS) system 18. In such embodiments, the control circuit includes transmitter circuitry 162 and an antenna 164. The transmitter circuitry 162 is communicatively coupled to the processor 130 via signal paths 166 and to the antenna 164 via signal paths 168. The signal paths 166, 168 may be embodied as any type of signal paths capable of facilitating communication between the transmitter circuitry 162 and the processor 130 and antenna 164, respectively. For example, similar to the signal paths 134, the signal paths 166, 168 may be embodied as any number of wires, printed circuit board traces, via, bus, intervening devices, and/or the like. The transmitter circuitry 162 may be configured to use any type of wireless communication protocol, standard, or technologies to transmit the joint force data to the display module 14 and/or computer assisted orthopaedic surgery (CAOS) system 18. For example, the transmitter circuitry 162 may be configured to use a wireless networking protocol, a cellular communication protocol such as a code division multiple access (CDMA) protocol, a Bluetoothϕ protocol, or other wireless communication protocol, standard, or technology.

Figure 11:
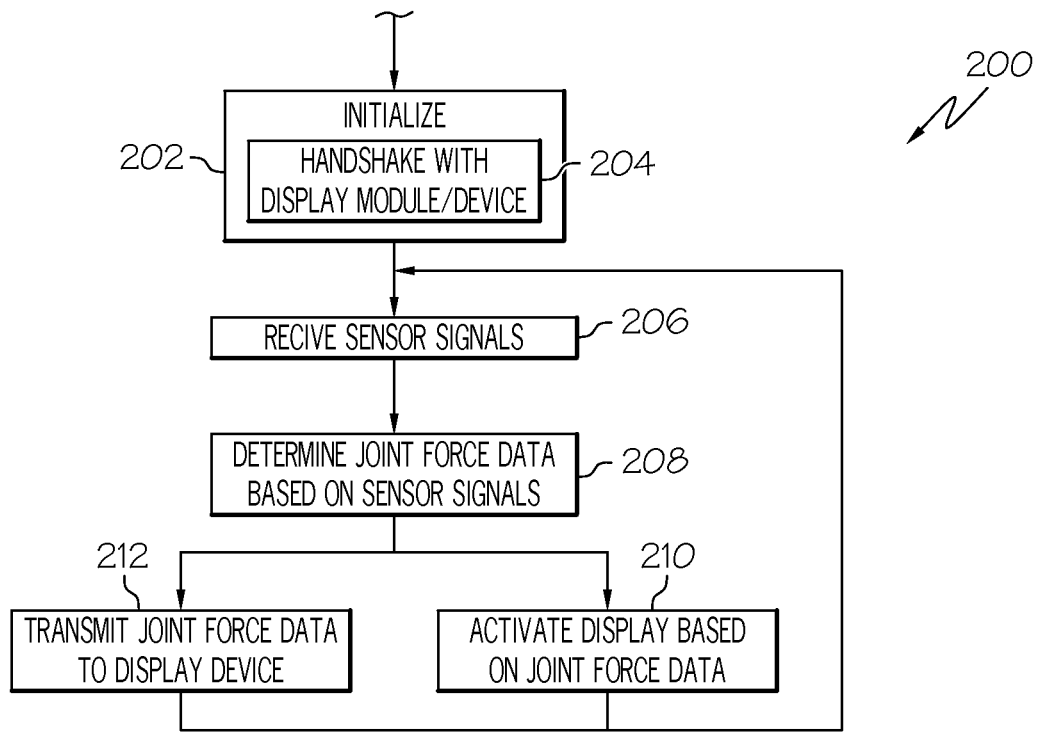
FIG. 11 is a simplified flow diagram of one embodiment of a method for determining and displaying joint force data that may be executed by the sensor module of FIG. 2.
Figure 12:
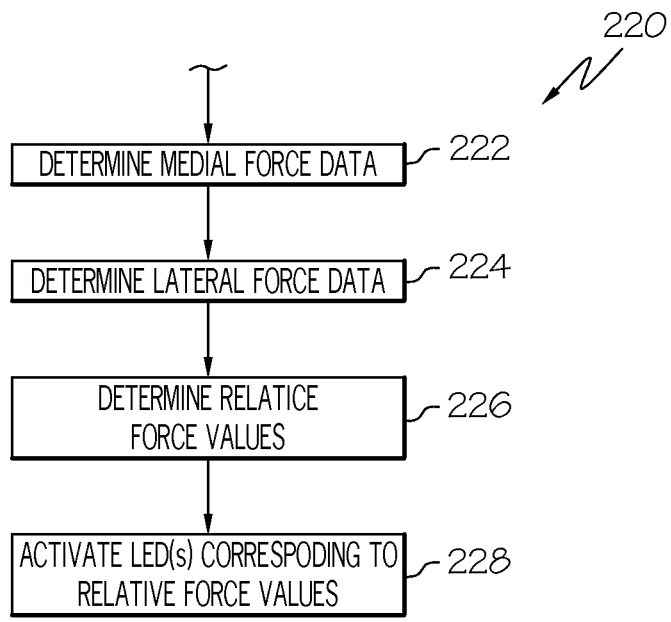
FIG. 12 is a simplified flow diagram of one embodiment of a method for displaying relative joint force data that may be executed by the sensor module of FIG. 2.

Referring now to FIGS. 11 and 12, in use, the control circuit 92 (see FIG. 10) is configured to execute a method 200 for determining joint force data of a patient's joint and providing a visual indication of the medial-lateral balance of the patient's joint force. The method 200 begins with block 202 in which the control circuit 92 is initialized. For example, in block 202, the control circuit 92 may perform any number of system checks, clear any registers of the processor 130, and/or perform other initialization and/or integrity checks. Additionally, in some embodiments, the control circuit 92 is configured to perform a handshaking routine in block 204 with the hand-held display device 14 and/or the computer assisted orthopaedic surgery (CAOS) system 18. During this handshaking routine, the control circuit 92 and the hand-held display device 14 and/or the computer assisted orthopaedic surgery (CAOS) system 18 may be configured to determine communication protocols and/or otherwise establish any type of communication procedures for transmitting the joint force data from the sensor module 12 to the device 14 or system 18.

In block 206, the control circuit 92 receives the sensor signals or data from the sensor array 90. As discussed above, the sensor array 90 generates sensor signals indicative of a joint force applied to the tibial paddle 34 when the paddle 34 is positioned in the knee joint of a patient. In block 208, the processor 130 of the control circuit 92 determines joint force data based on the sensor signals received from the sensor array 90. The joint force data is indicative of the joint force of the patient's knee. In some embodiments, the joint force data may be embodied as specific joint force values such as a medial joint force value, a lateral joint force value, an anterior joint force value, and/or a posterior joint force value, each force being determined in Newtons or similar force measurement unit. In such embodiments, the medial joint force may be determined based on the sensor signals from the pressure sensors 102, 104, 106, 108, 120, 124. The lateral joint force may be determined based on the sensor signals from the pressure sensors 112, 114, 116, 118, 122, 126. The anterior joint force may be based on the pressure sensor anterior-medial pressure sensors 102, 104, 120 and/or the anterior-lateral pressure sensors 112, 114, 122. Additionally, the posterior joint force may be based on the sensor signals from the posterior-medial pressure sensors 106, 108, 124 and/or the posterior-lateral sensors 116, 118, 126. Subsequently, in block 210 the control circuit 92 controls or otherwise activates the displays 50, 52 to display the joint force data determined in block 208. For example, in embodiments wherein one or more specific joint forces are determined, the processor 130 may display the determine joint forces or indicia thereof on the displays 50, 52.

Additionally or alternatively, the control circuit 92 may be configured to determine the relative medial-lateral joint force balance and display indicia of such medial-lateral balance on the displays 50, 52 in blocks 208, 210. For example, as illustrated in FIG. 12, the control circuit 92 may execute a method 220 for determining the relative medial-lateral joint forces of the patient's joint. In block 222, the control circuit 92 determines medial joint force data based on the sensor signals received from the pressure sensors 102, 104, 106, 108, 120, 124. Similarly, in block 224, the control circuit 92 determines lateral joint force data based on the sensor signals received from the pressure sensors 102, 104, 106, 108, 120, 124. The medial and lateral joint force data may be embodied as the specific joint force determined in Newtons or may be embodied as some representation thereof. For example, in some embodiments, the medial and lateral joint force data is measured in capacitance. It should be appreciated that the blocks 222 and 224 may be executed in either order.

In block 226, the control circuit 92 determines the relative medial-lateral balance of the joint force of the patient's joint. To do so, the control circuit 92 compares the medial force data and the lateral force data. For example, in one embodiment, the control circuit 92 is configured to determine a total force value by summing the medial force data and the lateral force data. The control circuit 92 subsequently determines a medial percentage value by dividing the medial force data by the total force value and a lateral percentage value by dividing the lateral force data by the total force value. As such, if the medial and lateral forces of a patient's joint are balanced, the medial percentage value would be determined to be about 50% and the lateral percentage value would be determined to be about 50%. Of course, in some embodiments, the control circuit 92 may be configured to determine only one of the medial and lateral percentage values, the remaining one being known or determined by simple subtraction from 100%.

In block 228, the control circuit 92 activates or controls the displays 50, 52 to provide a visual indication of the relative medial-lateral balance of the joint forces of the patient's joint. For example, in embodiments wherein the displays 50, 52 are embodied as light emitting diodes, the control circuit 92 is configured to activate or illuminate one or more of the light emitting diodes to provide a visual indication of the medial-lateral balance of joint forces. The control circuit 92 may use any display protocol or pattern of illumination of the light emitting diodes that provides an appropriate indication to the orthopaedic surgeon of such joint forces.

For example, in one particular embodiment, the control circuit 92 is configured to control the displays 50, 52 according to the display protocol 170 illustrated in and discussed above in regard to FIG. 7. In such embodiments, the control circuit 92 is configured to illuminate the centrally located light emitting diode 84 of the displays 50, 52 if the medial and lateral joint forces are about equal (i.e., about 50% medial-50% lateral). The control circuit 92 is configured to illuminate the centrally located light emitting diode 84 and the lateral light emitting diode 86 if the medial-lateral balance of the joint forces is about 45% medial-55% lateral, respectively. The control circuit 92 is configured to illuminate the lateral light emitting diodes 86, 88 if the medial-lateral balance of the joint forces is about 35% medial-65% lateral, respectively. Additionally, the control circuit 92 is configured to illuminate the lateral-most light emitting diode 88 if the medial-lateral balance of the joint forces is about 30% medial-70% lateral (or more lateral), respectively. Similarly, the control circuit 92 is configured to illuminate the centrally located light emitting diode 84 and the medial light emitting diode 82 if the medial-lateral balance of the joint forces is about 55% medial-45% lateral, respectively. The control circuit 92 is configured to illuminate the lateral light emitting diodes 80, 82 if the medial-lateral balance of the joint forces is about 65% medial-35% lateral, respectively. Additionally, the control circuit 92 is configured to illuminate the medial-most light emitting diode 80 if the medial-lateral balance of the joint forces is about 70% medial-30% lateral (or more medial), respectively.

In this way, sensor module 12 provides a visual indication to the orthopaedic surgeon of the relative medial and lateral forces of the patient's joint. As discussed in more detail below, the orthopaedic surgeon can perform balancing procedures on the patient's knee joint while monitoring the current balance of the medial and lateral forces via the displays 50, 52 to achieve the desired balance for the particular patient. Additionally, because the sensor module 12 includes a display 50, 52 on either side, the orthopaedic surgeon is provide the visual indication of the joint forces whether the surgeon is operating on the patient's left or right knee.

Referring back to FIG. 12, in addition to activating the displays 50, 52 to provide the visual notification of the joint forces in block 210, the sensor module 12 may be configured to transmit the joint force data in block 212. As discussed above, the sensor module 12 may transmit the joint force data to the hand-held display 14 and/or computer assisted orthopaedic surgery (CAOS) system 18 in block 212. The transmitted joint force data may be embodied as the specific joint forces measured in Newtons, for example, or may be representations thereof. For example, the sensor signals received from the sensor array 90 or electrical representations of the levels of such signals may be transmitted in block 212. Regardless, the sensor module 12 is configured to transmit joint force data that is indicative of the joint forces of the patient's knee joint to the display 14 and/or the system 18 in block 212.

Figure 13:
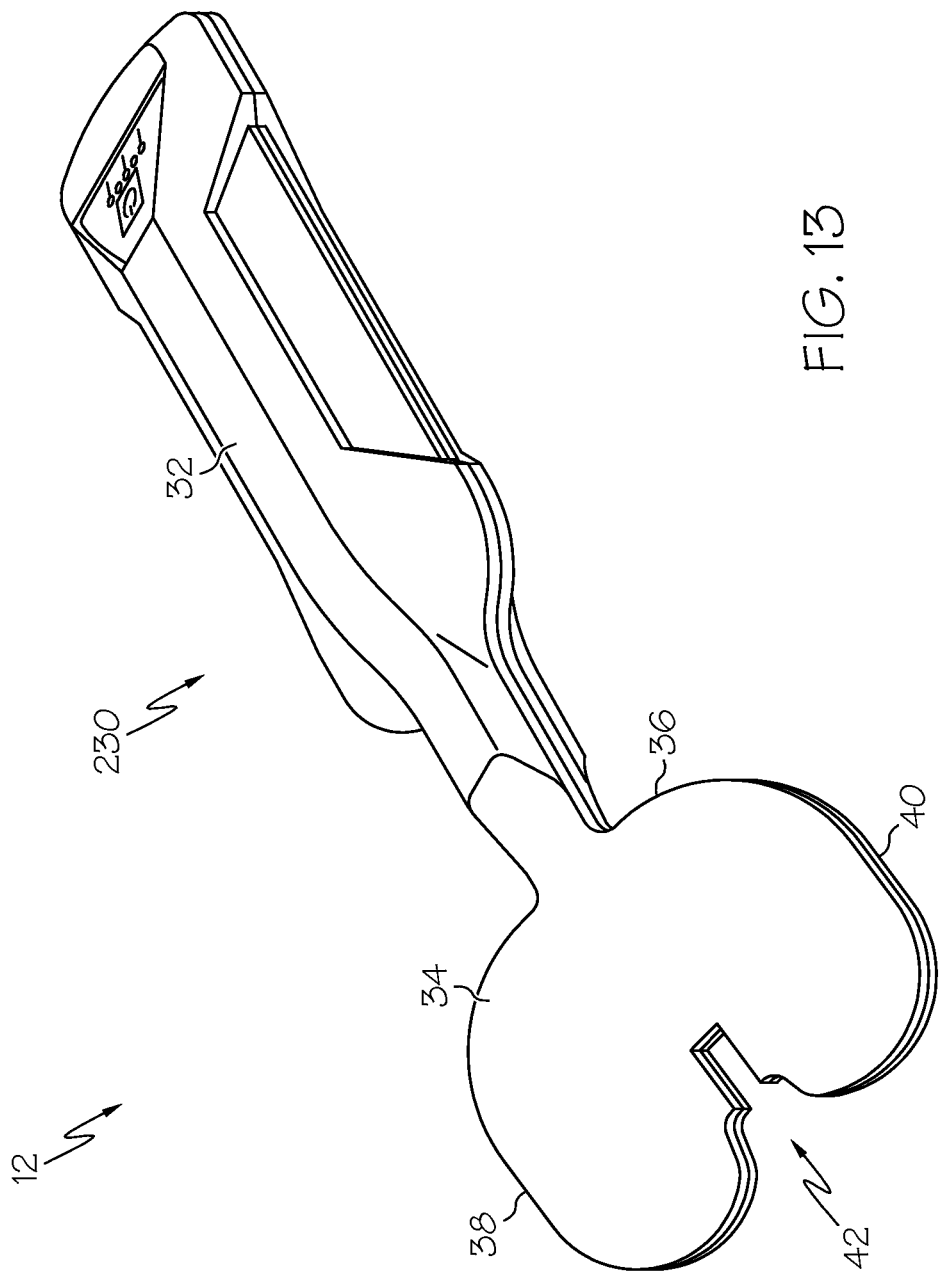
FIG. 13 is a perspective view of another embodiment of a sensor module of the system of FIG. 1.
Figure 14:
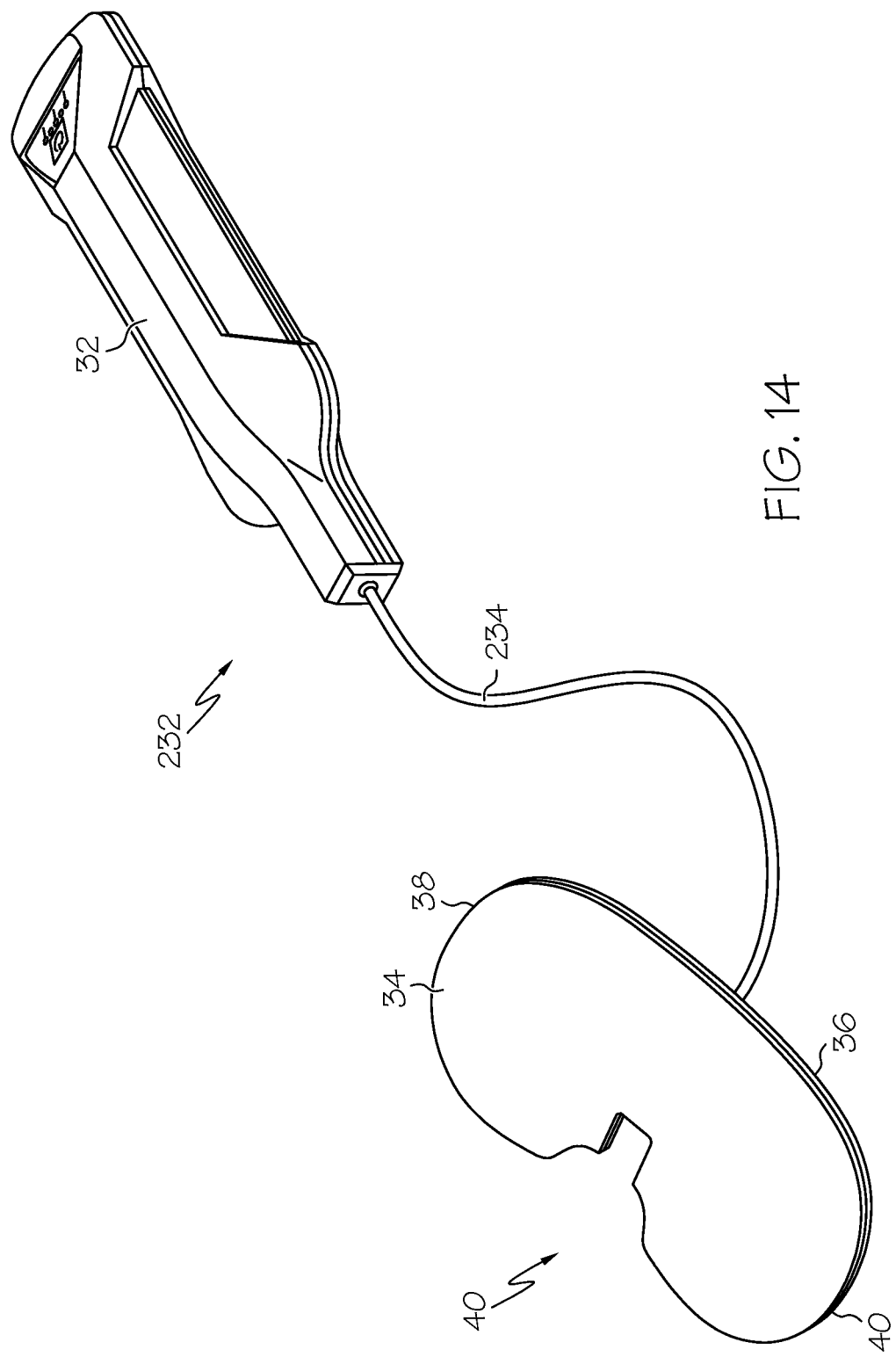
FIG. 14 is a perspective view of another embodiment of a sensor module of the system of FIG. 1.
Figure 15:
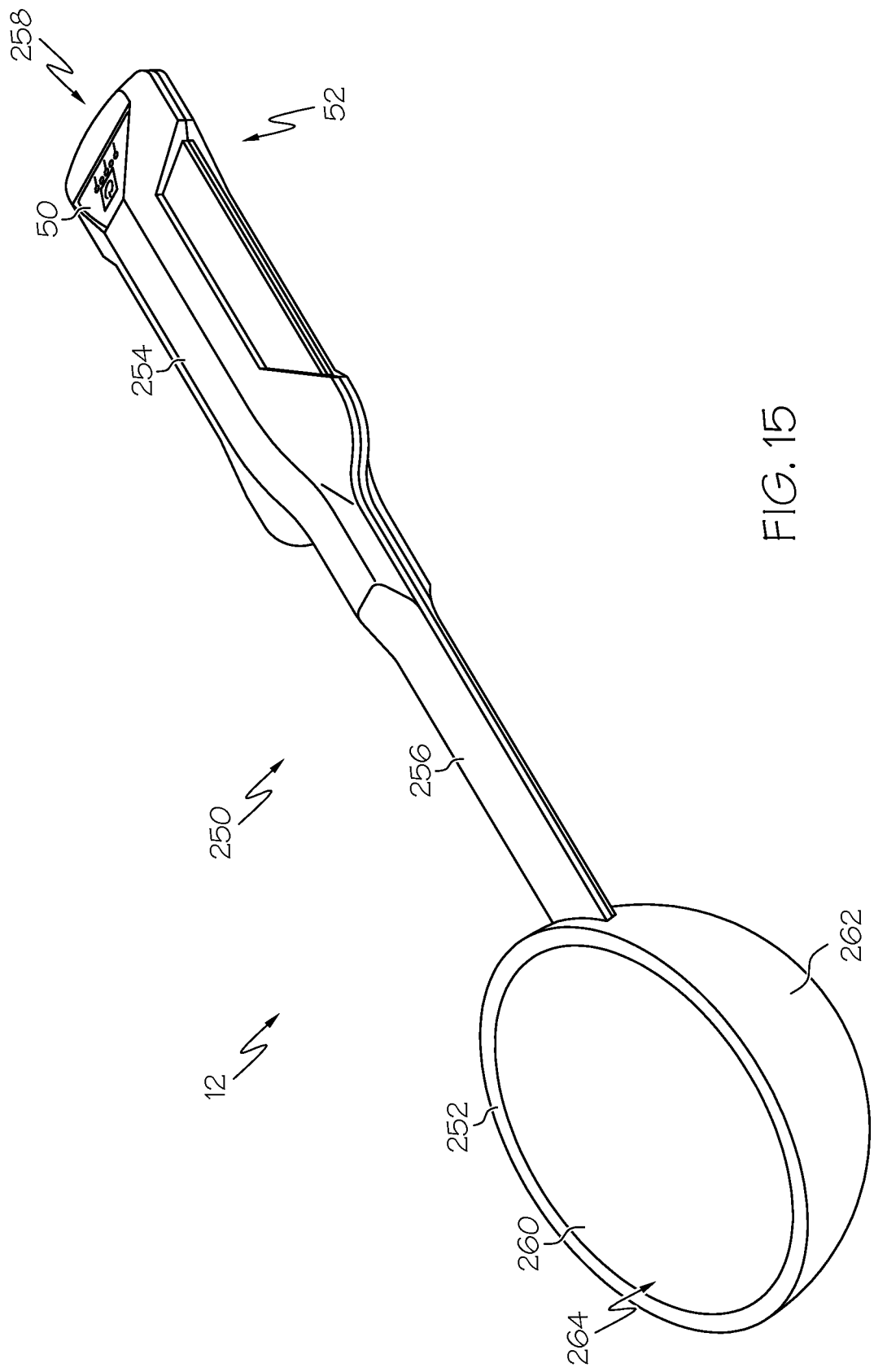
FIG. 15 is a perspective view of another embodiment of a sensor module of the system of FIG. 1.
Figure 16:
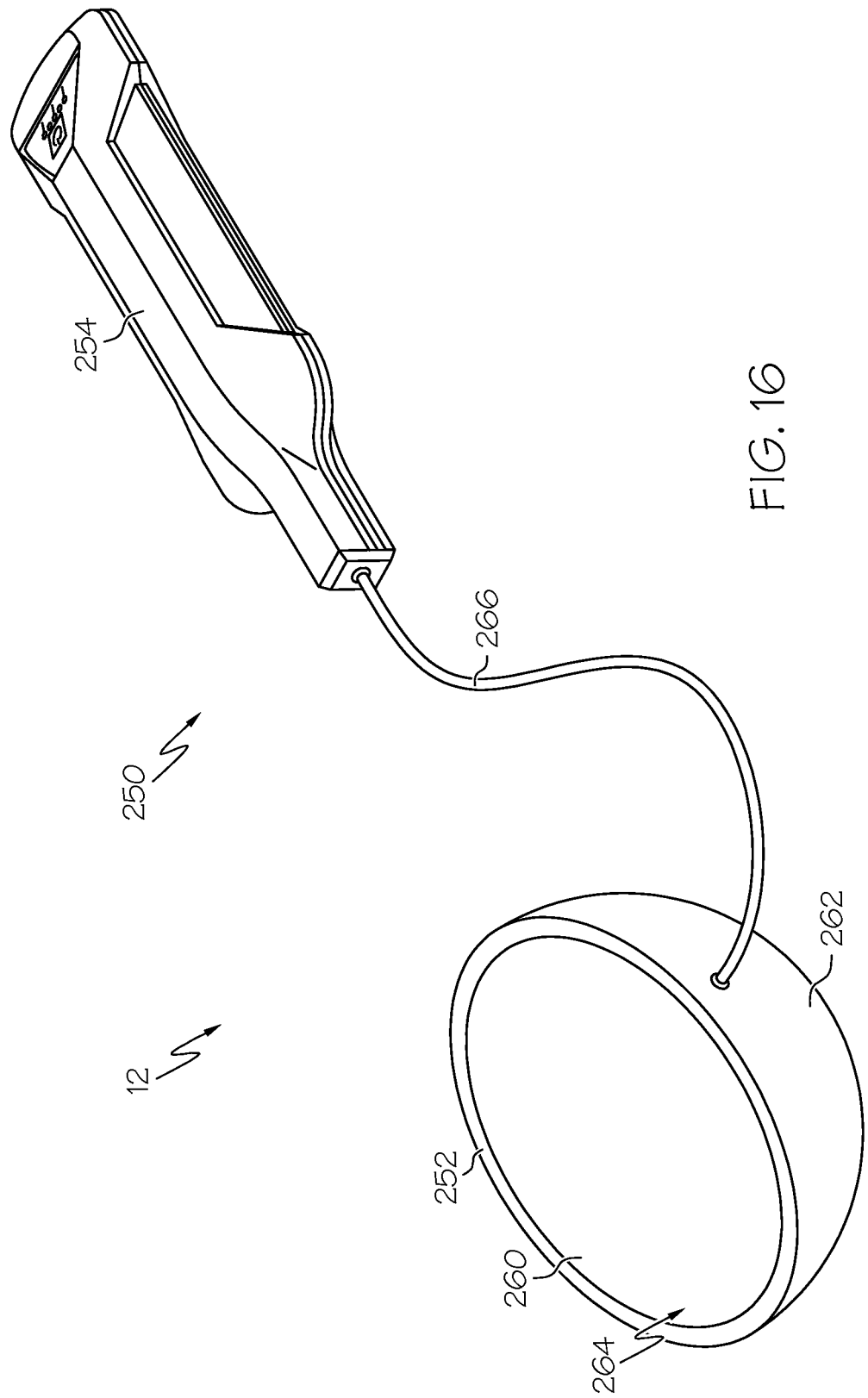
FIG. 16 is a perspective view of another embodiment of a sensor module of the system of FIG. 1.

Referring now to FIGS. 13 and 14, in other embodiments, the handle 32 and tibial paddle 34 may be coupled to each other at other orientations and/or via other intervening structures. For example, as shown in FIG. 13, the sensor module 12 may be embodied as a module 230 in which the handle 32 is coupled to the anterior side 36 of the tibial paddle 34 is some embodiments. In such embodiments, the handle 32 extends anteriorly from the patient's knee joint (e.g., through an anterior capsular incision) when the tibial paddle 34 is inserted therein. Alternatively, as illustrated in FIG. 14, the sensor module 12 may be embodied as a module 232 in which the handle 32 and the tibial paddle 34 are coupled to each other via a wire 234. The wire 234 may be embodied as a plurality of wires, cables, or other interconnects that communicatively couple the sensor array 90 positioned in the tibial paddle 34 to the control circuit 92 located in the handle 32. Although the wire 234 is illustratively coupled to the posterior side 36 of the tibial paddle 34 in the embodiment of FIG. 14, it should be appreciated that the wire 234 may be coupled to the tibial paddle 34 on the lateral side 38, the medial side 40, or the posterior side 42 in other embodiments.

Referring now to FIGS. 15-19, in some embodiments, the sensor module 12 may be configured for use with joint's other than the patient's knee joint. For example, in one embodiment, the sensor module 12 is embodied as a sensor module 250, which includes a sensor housing 252 and a handle 254 connected to the sensor housing 252 via an elongated neck 256. The handle 254 is similar to the housing 32 of the sensor module 12 and includes the control circuit 92 positioned therein and displays 50, 52 coupled to an end 258 of the handle 254. The sensor housing 252, however, is configured to be positioned in a ball-and-socket joint of the patient such as the patient's hip joint or shoulder joint. As such, the sensor housing 252 is substantially "cup"-shaped and includes a concave upper housing piece 260 and a corresponding convex lower housing piece 262. The concave upper housing piece 260 defines an inner recess 260, which may receive a portion of an orthopaedic prosthetic or prosthetic trial or an end of a patient's natural or prosthetic bone during the performance of the orthopaedic surgical procedure. Similar to the sensor housing 30, the sensor array 90 is positioned in the sensor housing 252 and is configured to generate sensor signals indicative of the joint forces of the patient's relative joint.

In some embodiments, the sensor housing 252 may be detached from the handle 254, but communicatively coupled therewith, to improve the ease of use of the sensor module 250 with particular joints. For example, as illustrated in FIG. 12, the sensor housing 252 and the handle 254 may be detached from each other but communicatively coupled via a wire or plurality of wires 266. That is, the sensor array 90 positioned in the sensor housing 252 is communicatively coupled with the control circuit 90 positioned in the handle 254.

Figure 17:
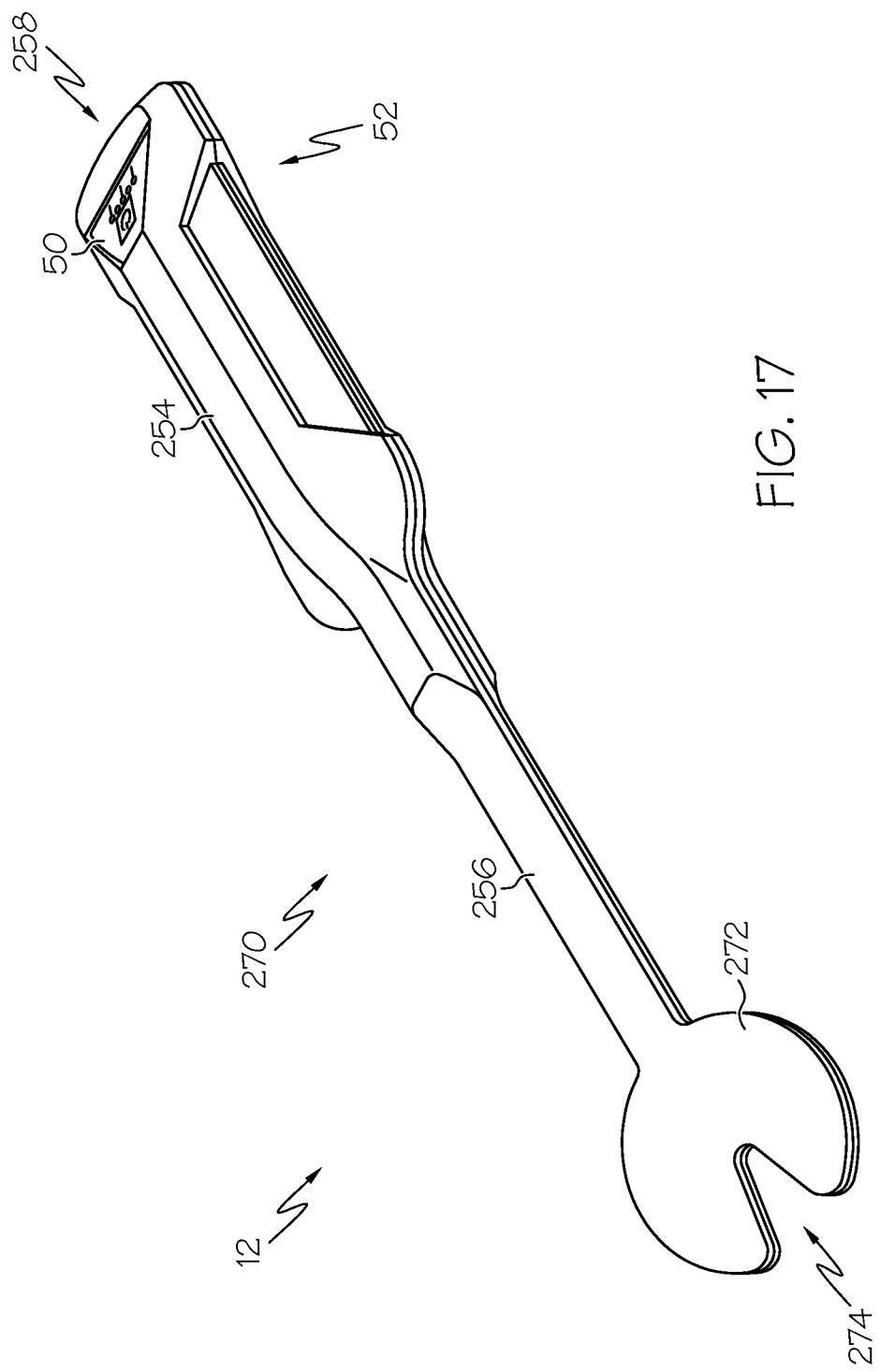
FIG. 17 is a perspective view of another embodiment of a sensor module of the system of FIG. 1.

In another embodiment as illustrated in FIG. 17, the sensor module 12 may be embodied as a sensor module 270 configured to be used with a spinal joint of the patient. The sensor module 270 includes a spinal paddle 272 coupled to the handle 254 via the elongated neck 256. The spinal paddle 272 is configured to be inserted between the vertebra of the patient's spine. In the illustrative embodiment, the paddle 272 has a substantial curricular shape, but may have other shapes in other embodiments. The spinal paddle 272 includes a notch 274 configured to receive a portion of the patient's spinal cord such that the spinal paddle 272 may be fully inserted into the patient's spine. A sensor array is included in the spinal paddle 272 to measure or sense the joint force of the patient's spine. The spinal senor array may have any number of pressure sensors arranged in a configuration similar to the sensor array 90 discussed above or in another configuration.

Figure 18:
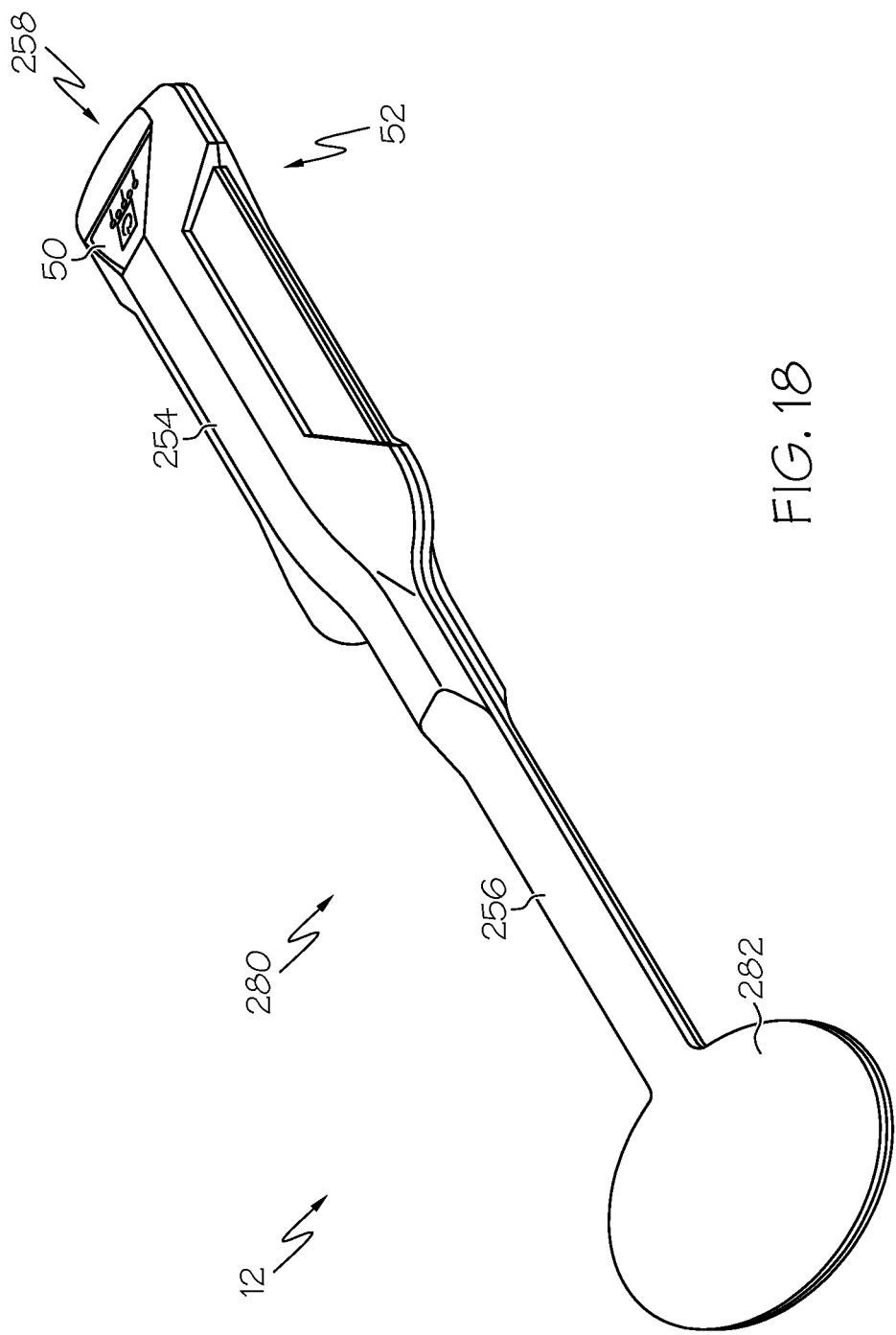
FIG. 18 is a perspective view of another embodiment of a sensor module of the system of FIG. 1.

Additionally, in some embodiments as illustrated in FIG. 18, the sensor module 12 may be embodied as a sensor module 280 configured to be used with the patella of the patient's knee joint to measure patellofemoral forces. Similarly to the sensor module 270 discussed above in regard to FIG. 17, the sensor module 280 includes a patella paddle 282 coupled to the handle 254 via the elongated neck 256. The patella paddle 282 is configured to be inserted between the patient's patella and femur. In the illustrative embodiment, the paddle 282 has a substantial oval shape, but may have other shapes in other embodiments. A sensor array is included in the patella paddle 282 to measure or sense the force exerted by the patient's patella on the patient's femur. The patella senor array may have any number of pressure sensors arranged in a configuration similar to the sensor array 90 discussed above or in another configuration.

Figure 19:
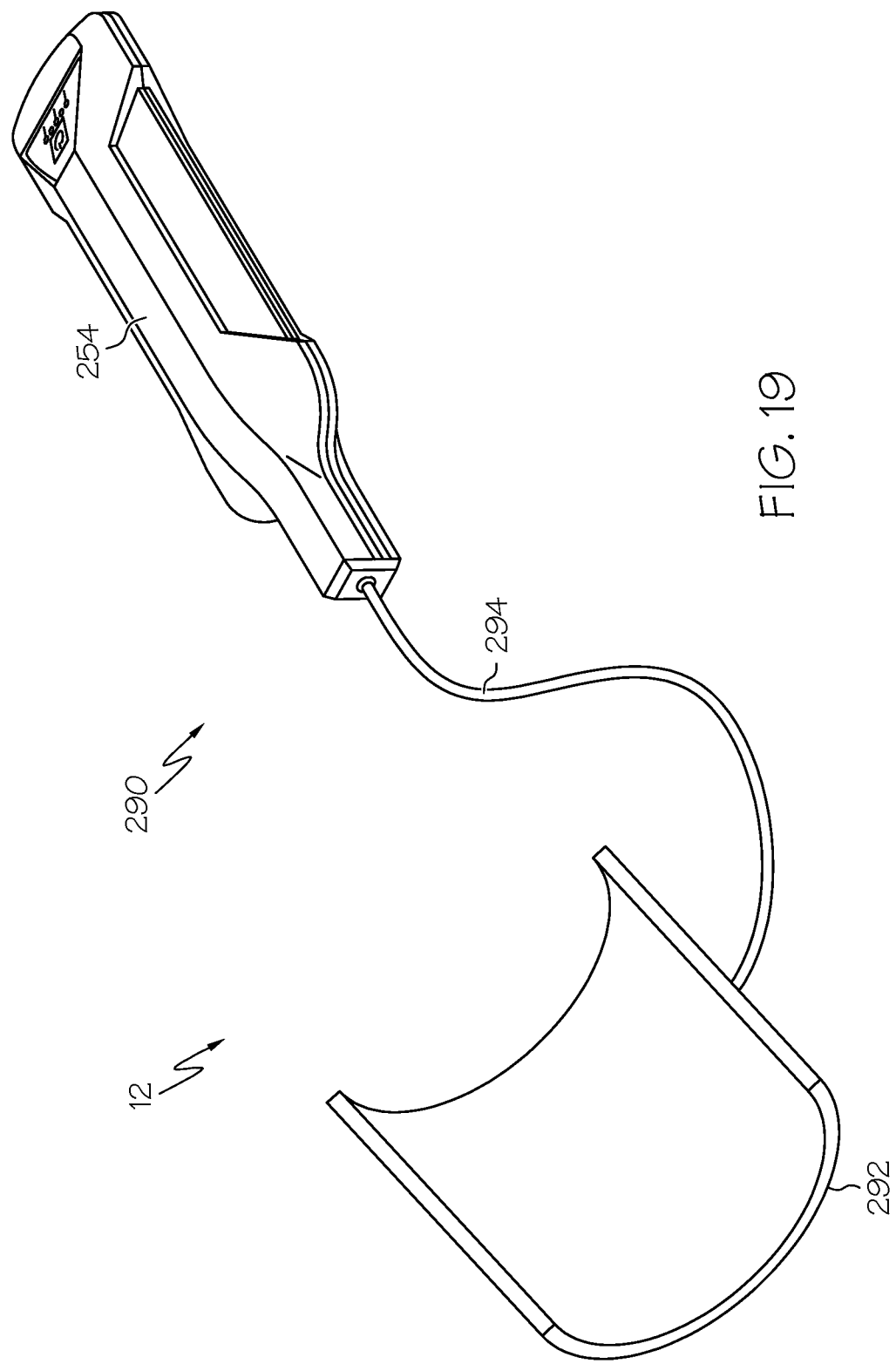
FIG. 19 is a perspective view of another embodiment of a sensor module of the system of FIG. 1.

Referring now to FIG. 19, in another embodiment, the sensor module 12 is embodied as a sensor module 290 configured to be used with an ankle joint of the patient. The sensor module 290 includes an ankle sensor housing 292 coupled to handle 254 via a wire 294. The wire 294 may be embodied as a plurality of wires, cables, and/or other interconnects to communicatively couple the ankle sensor housing 292 and the control circuit 92 located in the handle 254. The ankle sensor housing 292 is configured to be inserted in an ankle joint of the patient. In the illustrative embodiment, the ankle sensor housing 292 is shaped as a half-cylinder, but may have other shapes in other embodiments. A sensor array is included in the ankle sensor housing 292 to measure or sense the patient's ankle joint force. The ankle senor array may have any number of pressure sensors arranged in a configuration similar to the sensor array 90 discussed above or in another configuration.

Referring now to FIGS. 20-26, the hand-held display module 14 includes a housing 300 sized to be held in the hands of an orthopaedic surgeon and used during the performance of an orthopaedic surgical procedure. In this way, the display module 14 is configured to be mobile. The display module 14 also includes a display 302 coupled to an upper side 304 of the housing 300. A plurality of user input buttons 306, 308, 310 are also positioned on the upper side 304 of the housing 300 below the display 302. The display module 14 also includes a power button 312. In the illustrative embodiment of FIGS. 20-26, the power button 312 is positioned below the row of input buttons 306, 308, 310, but the buttons 306, 308, 310, 312 may be positioned in other configurations and/or orientations in other embodiments. Additionally, the display module 14 may include a power-on indicator 314 and a battery state indicator 316 located on the upper side 304 of the housing 300.

As discussed above, the hand-held display module 14 is configured to be used with the sensor module 12 to receive joint force data form the module 12 and display indicia on the display 302 indicative of the joint forces of the patient's joint. Similar to the sensor module 12, the display module 14 may be configured to determine the relative medial-lateral and/or anterior-posterior balance of the patient's joint forces and display indicia of such balances on the display 302. Additionally, the display module 14 may be configured to determine the anterior-posterior balance of the patient's joint forces and display indicia of such balances on the display 302. Further, as discussed in more detail below, the display module 14 may be configured to determine the specific joint force values (e.g., the medial and lateral joint forces) and display such force values on the display 302. That is, in addition to an indication of the joint forces relative to each other, the hand-held display module 14 may calculate or otherwise determine the magnitude of the joint force values as measured in a suitable unit of force such as Newtons. Additionally, the display module 14 may also be configured to perform other functions such as store screenshots and data of the patient's joint forces as displayed on the display 302 and download such data to other devices.

Figure 22:
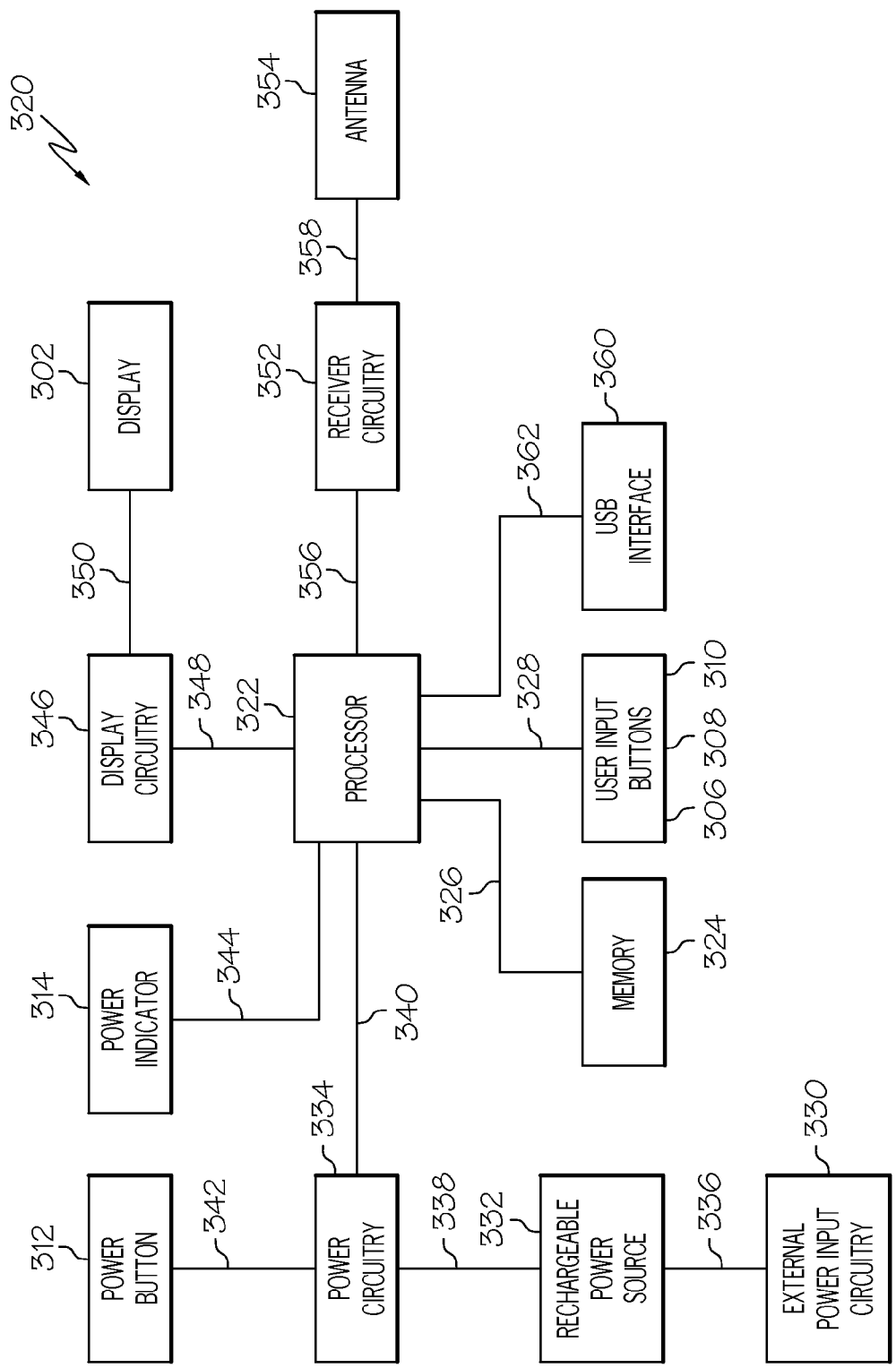
FIG. 22 is a simplified block diagram of one embodiment of an electrical circuit of the display module of FIG. 20.

As illustrated in FIG. 22, the hand-held display module 14 includes a control circuit 320 positioned in the housing 300. The control circuit 320 includes a processor 322 and a memory device 324. The processor 322 may be embodied as any type of processor configurable to perform the functions described herein. For example, the processor 322 may be embodied as a separate integrated circuit or as a collection of electronic devices. Additionally, the processor may be a single or multi-core processors. Although only a single processor 322 is illustrated in FIG. 22, it should be appreciated that in other embodiments, the control circuit 320 may include any number of additional processors. The memory device 324 may be embodied read-only memory devices and/or random access memory devices. For example, the memory device 324 may be embodied as or otherwise include electrically erasable programmable memory devices (EEPROM), dynamic random access memory devices (DRAM), synchronous dynamic random access memory devices (SDRAM), double-data rate dynamic random access memory devices (DDR SDRAM), and/or other volatile or non-volatile memory devices. Additionally, although only a single memory device is illustrated in FIG. 22, in other embodiments, the control circuit 320 may include additional memory devices.

The processor 322 is communicatively coupled to the memory device 324 via signal paths 326. The signal paths 326 may be embodied as any type of signal paths capable of facilitating communication between the processor 322 and the memory device 324. For example, the signal paths 326 may be embodied as any number of wires, printed circuit board traces, via, bus, intervening devices, and/or the like.

The processor 322 is also communicatively coupled to the user input buttons 306, 308, 310 via signal paths 328 and to the power indicator 314 via signal paths 344. Similar to signal paths 326, the signal paths 328, 344 may be embodied as any type of signal paths capable of facilitating communication between the processor 322 and the user input buttons 306, 308, 310 and the power indicator 314, respectively. For example, the signal paths 328, 344 may include any number of wires, printed circuit board traces, via, bus, intervening devices, and/or the like. The user input buttons 306, 308, 310 are software or "soft" buttons, the functionality of each of which may be determined based on the particular screen displayed on the display 302.

The control circuit 320 also includes an external power input circuitry 330, a rechargeable power source 332 such as a rechargeable battery or the like, and power circuitry 334. The external power input circuitry 330 is configured to receive a plug of a charger such as a "wall charger" and is communicatively coupled to the rechargeable power source 332 via signal paths 336. The rechargeable power source 332 is communicatively coupled to the power circuitry 334 via signal paths 338. The power circuitry 334 is communicatively coupled to the processor 332 via signal paths 340 and to the power button 312 via signal paths 342. The signal paths 336, 338, 340, 342 may be embodied as any type of signal paths including, for example any number of wires, printed circuit board traces, via, bus, intervening devices, and/or the like. The power circuitry 334 may include power control, distribution, and filtering circuitry and is configured to provide or distribute power the rechargeable power source 332 to the processor 322 and other devices or components of the control circuit 320.

The control circuit 320 also includes display circuitry 346 for driving and/or controlling the display 392. The display circuitry 346 is communicatively coupled to the processor 322 via signal paths 348 and to the display 302 via signal paths 350. The signal paths 348, 350 may be embodied as any type of signal paths capable of facilitating communication between the processor 322 and display circuitry 346 and the display circuit 346 and display 302, respectively. For example, the signal paths 348, 350 may be embodied as any number of wires, printed circuit board traces, via, bus, intervening devices, and/or the like.

As discussed above, the hand-held display module 14 is configured to receive joint force data from the sensor module 12. As such the control circuit 320 includes receiver circuitry 352 and an antenna 354. The receiver circuitry 352 is communicatively coupled to the processor 322 via signal paths 356 and to the antenna 354 via signal paths 358. The signal paths 356, 358 may be embodied as any type of signal paths capable of facilitating communication between the receiver circuitry 352 and the processor 322 and the antenna 354, respectively. For example, the signal paths 356, 358 may be embodied as any number of wires, printed circuit board traces, via, bus, intervening devices, and/or the like. The receiver circuitry 352 may be configured to use any type of wireless communication protocol, standard, or technologies to receive the joint force data from the sensor module 12. For example, as discussed above in regard to the sensor module 12, the display module 14 may be configured to a wireless networking protocol, a cellular communication protocol such as a code division multiple access (CDMA) protocol, a Bluetooth® protocol, or other wireless communication protocol, standard, or technology to communicate with the sensor module 12.

The control circuit 320 also includes a universal serial bus (USB) interface 360. The USB interface 360 is communicatively coupled to the processor 322 via signal paths 362, which may be embodied as any type of signal paths capable of facilitating communication between the USB interface 360 and the processor 322. For example, the signal paths 362 may be embodied as any number of wires, printed circuit board traces, via, bus, intervening devices, and/or the like. The USB interface 360 may be used to download data, such as joint force data or screenshot data, from the display module 14 to another device such as a computer. Additionally, the USB interface 360 may be used to update the software or firmware of the control circuit 320.

Referring now to FIGS. 23-26, in use, the control circuit 320 is configured to execute a method 400 for determining and displaying joint force data related to a patient's joint to an orthopaedic surgeon. The method 400 begins with block 402 in which the control circuit 320 is initialized. For example, in block 402, the control circuit 320 may perform any number of system checks, clear any registers of the processor 322, and/or perform other initialization and/or integrity checks. Additionally, in some embodiments, the control circuit 320 is configured to perform a handshaking routine in block 404 with the sensor module 12. During this handshaking routine, the control circuit 320 and the sensor module 12 may be configured to determine communication protocols and/or otherwise establish any type of communication procedures for transmitting the joint force data from the sensor module 12 to the device module 14.

In block 406, the control circuit 320 receives the joint force data from the sensor module 12. As discussed above, the joint force data is indicative of the joint force of the patient's knee as indicated by the sensor signals generated by the sensor array 90 of the sensor module 12. In block 408, the control circuit 320 determines a medial joint force value and a lateral joint force value based on the joint force data received in block 406. The medial joint force value is based on the sensor signals received from the pressure sensors 102, 104, 106, 108, 120, 124 and the lateral joint force value is based on the sensor signals received from the pressure sensors 112, 114, 116, 118, 122, 126. In block 410, the control circuit 320 determines an average medial/lateral force value based on the medial joint force value and the lateral joint force value determined in block 408. The medial joint force value, the lateral joint force value, and the average joint force value are subsequently displayed on the display 302 in block 412. For example, as illustrated in the screenshots 450, 452, 454 in FIGS. 24, 25, and 26, the medial joint force value 430 is displayed toward a medially designated side 460 of the display 302, the lateral joint force value 432 is displayed toward a laterally designated side 462 of the display 302, and the average force value 434 is displayed toward a posterior designated side 464.

In blocks 414, 416, the control circuit 320 determines which mode the orthopaedic surgeon has selected. In the illustrative embodiment, the orthopaedic surgeon may select a first mode in which indicia of only the medial-lateral balance of the patient's joint forces is displayed on the display 302 or a second mode in which may indicia of the medial-lateral and the anterior-posterior balance of the patient's joint forces is displayed in the display 302. The user may switch between the two modes by selecting the appropriate user input buttons 306, 308, 310.

If the orthopaedic surgeon has selected the medial-lateral only mode, the method 400 advances to block 418 in which indicia of the medial-lateral balance of the joint forces of the patient's knee are displayed on the display 302. To do so, as illustrated in FIG. 24, a screen display 450 is presented on the display 302 of the display module 14. The screen display 450 includes a background image 470, which illustrative is embodied as an image of a proximal end of a resected tibia. The control circuit 320 displays a balance bar 472 on the background image 470 and an icon 474 on the balance bar 472 in a position that indicates the relative medial-lateral balance of the joint forces of the patient's joint. For example, in the illustrative screen display 450, the icon 474, which is embodied as a rounded rectangle, is displayed on the balance bar 472 toward the lateral side 462 of the screen display 450 (i.e., the side of the display 302 corresponding to the lateral side of the resected tibia image 470, which illustrative corresponds to the right side of the display 302). Such positioning indicates that the lateral force component of the total joint force of the patient's knee joint is greater than the medial joint force component. The farther way the icon 474 is located from the center of the balance bar 472, the greater the respective medial or lateral force component. In some embodiments, the balance bar 472 may be calibrated to provide an indicative of the numerical balance between the medial-lateral forces. Additionally, in some embodiments, the background image 470 includes an "balanced" icon 476, illustratively embodied as a rounded rectangular outline, positioned on the background image 470 such that when the icon 474 is located within the boundaries of the icon 476, the medial joint force and the lateral joint force of the patient's knee are balanced or within a predetermined threshold of each other.

If, however, the orthopaedic surgeon has selected the medial-lateral and anterior-posterior mode, the method 400 advances to block 420 in which indicia of the medial-lateral and anterior-posterior balance of the joint forces of the patient's knee are displayed on the display 302. To do so, as illustrated in FIG. 25, a screen display 452 is presented on the display 302 of the display module 14. The screen display 450 includes the background image 470 on which the balance bar 472, which illustrative is embodied as an image of a proximal end of a resected tibia. The control circuit 320 displays a balance bar 472 and icon 474 are displayed. Again, the position of the icon 474 on the balance bar 472 indicates the relative medial-lateral balance of the joint forces of the patient's joint. In addition, however, a medial end 480 of the balance bar 472 and a lateral end 482 of the balance bar 472 are positioned based on the corresponding anterior-posterior balance. For example, the medial end 480 of the balance bar 472 is positioned toward the posterior side 464 of the display 302 or the anterior side 466 of the display 302 based on the anterior-posterior balance of the medial joint force. As discussed above, the anterior posterior balance of the medial joint force may be determined based on the sensor signals from the pressure sensors 102, 104, 120 for the anterior component and the pressures 106, 108, 124 for the posterior component. Similarly, the lateral end 482 of the balance bar 472 is positioned toward the posterior side 464 of the display 302 or the anterior side 466 of the display 302 based on the anterior-posterior balance of the lateral joint force. As discussed above, the anterior posterior balance of the lateral joint force may be determined based on the sensor signals from the pressure sensors 112, 114, 122 for the anterior component and the pressures 116, 118, 126 for the posterior component.

Figure 26:
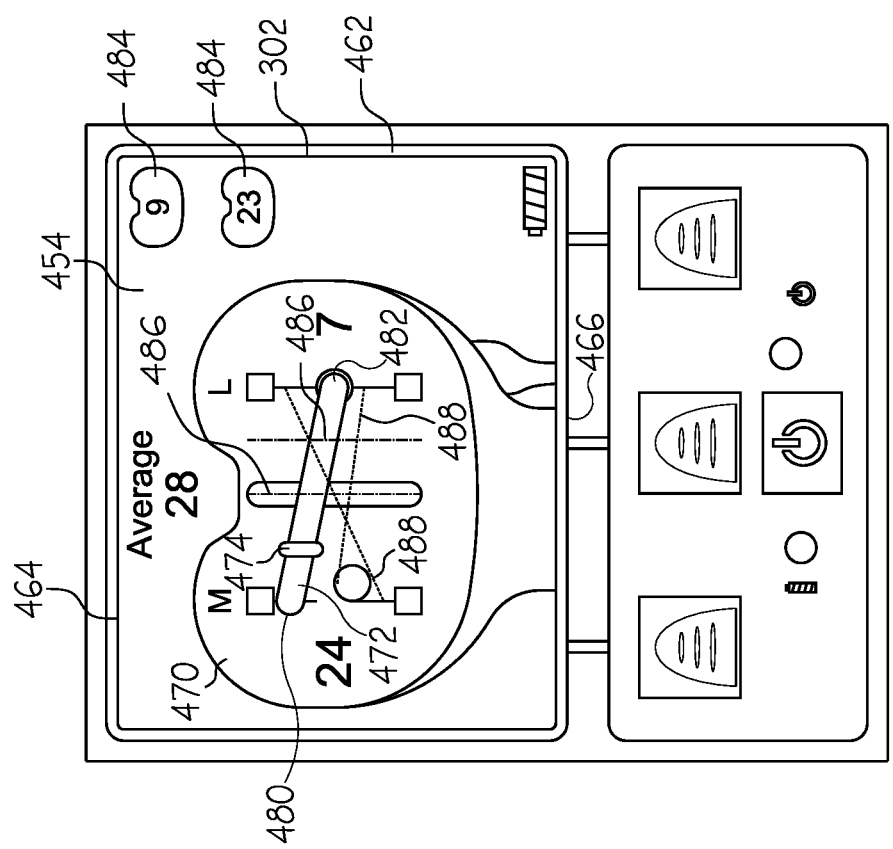

In the illustrative screen display 454 of FIG. 26, the medial end 480 of the balance bar 472 is positioned toward the anterior side 466 of the display 302 and the lateral end 482 of the balance bar 472 is positioned toward the posterior side 464 of the display 302. Such positioning indicates that the anterior force component of the medial force component is greater than the posterior force component of the medial force component and that the posterior force component of the lateral force component is greater than the anterior force component of the lateral force component. The farther way the ends 480, 482 are from the anterior-posterior center, the greater the respective anterior or posterior force component.

Figure 23:
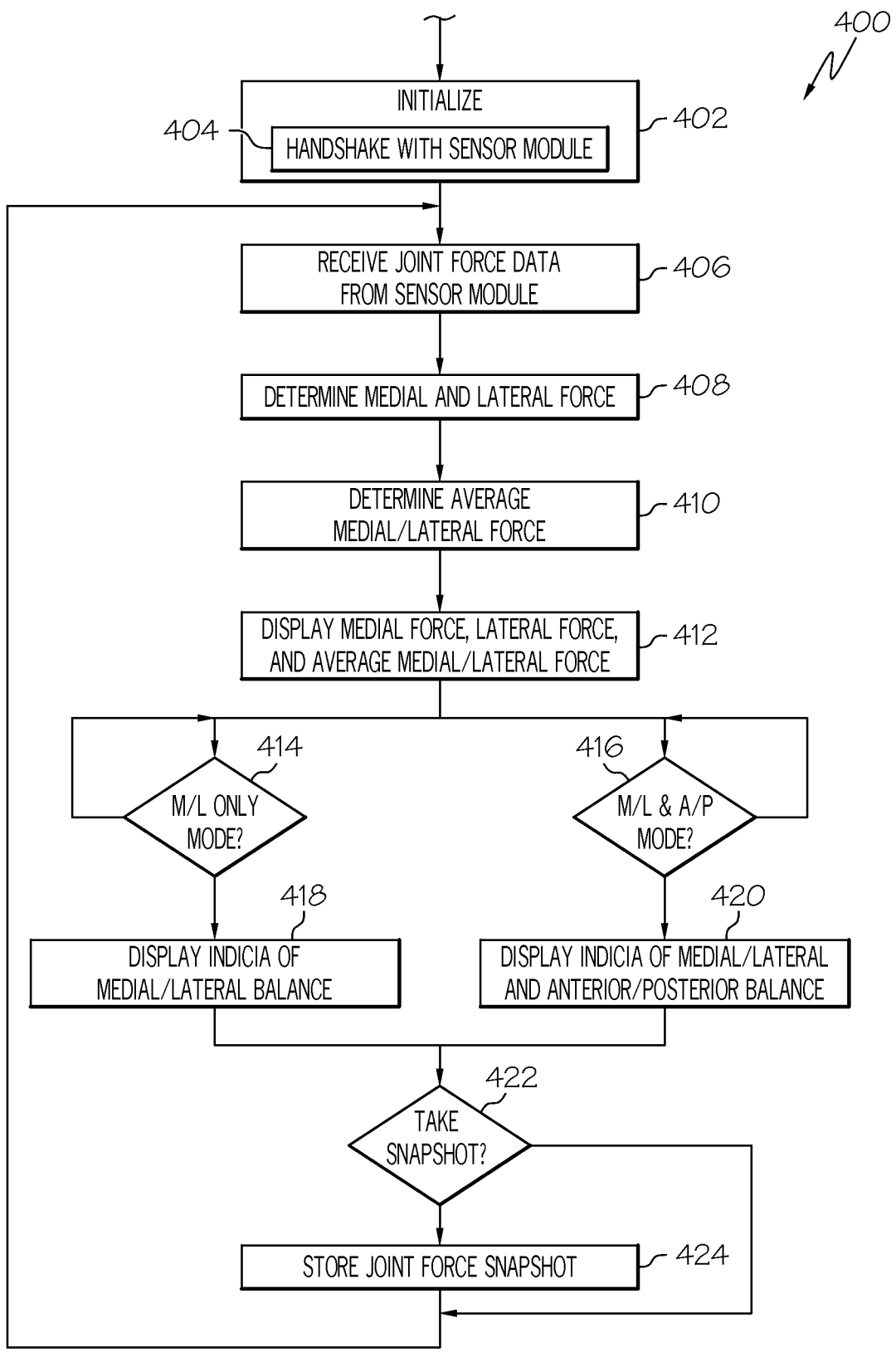
FIG. 23 is a simplified flow diagram of one embodiment of a method for displaying joint force data.

Referring now back to FIG. 23, once the appropriate indicia of the joint force balances have been displayed on the display 302, the control circuit 320 determines whether the orthopaedic surgeon would like to take a snapshot of the current display in block 422. The orthopaedic surgeon may take a screenshot of the display 302 by selecting the appropriate user input button 306, 308, 310. Additionally, the screenshot is stored in the memory device 324 in block 424 and may be subsequently downloaded from the display module 14.

When a screenshot is stored, an icon 484 appears in the upper right corner of the display 302. The icon 484 displays the average force value that was measured on the respective stored screenshot. Any number of icons 484 may be displayed on the display 302 to indicate corresponding stored screenshots. Additionally, although only a select number of icons 484 may be displayed on the display 302, the control circuit 320 may be configured to store any number of screenshots. In addition to the icon 484, when a screenshot is stored, a corresponding vertical balance line 486 is displayed on the display 302. The balance line 486 provides a visual indication of the medial-lateral balance of the joint forces displayed in the associated stored screenshot. Further, if the orthopaedic surgeon has selected the medial-lateral and anterior-posterior mode, an anterior-posterior balance line 488 is displayed on the display 302. The balance line 488 provides a visual indication of the anterior-posterior balance of the medial and lateral forces of the patient's knee joint displayed in the associated stored screenshot.

Figure 28:
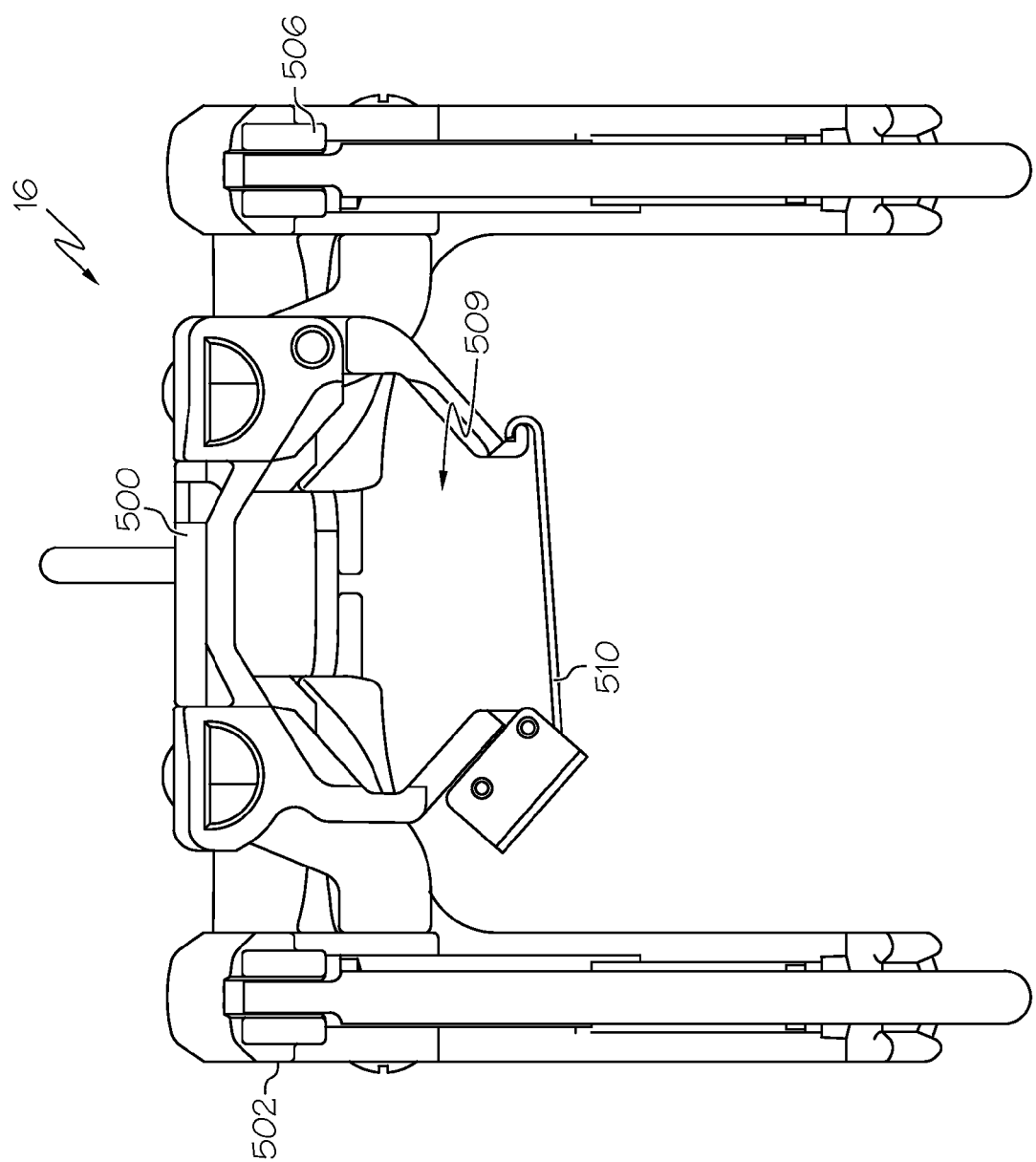
FIG. 28 is an elevation view of an end of the joint distactor of FIG. 27.

Referring now to FIGS. 27-30, as discussed above, the sensor module 12 may be coupled to the joint distractor 16 during the performance of an orthopaedic surgical procedure. The joint distractor 16 includes a cradle 500 sized and configured to receive the sensor module 12, a first distractor component 502 movably coupled to a side 504 of the cradle 500, and a second distractor component 506 movably coupled to a side 508 of the cradle 500 opposite the side 504. As shown in FIG. 28, the cradle 500 includes an opening 509 having a shape corresponding to the cross-sectional shape of the handle 32 of the sensor module 12. The sensor module 12 may be coupled to the joint distractor 16 by sliding the sensor module 12 handle-first into the cradle 500. The cradle 500 includes a locking mechanism 510 that is operable to lock the sensor module 12 in the cradle 500.

Figure 29:
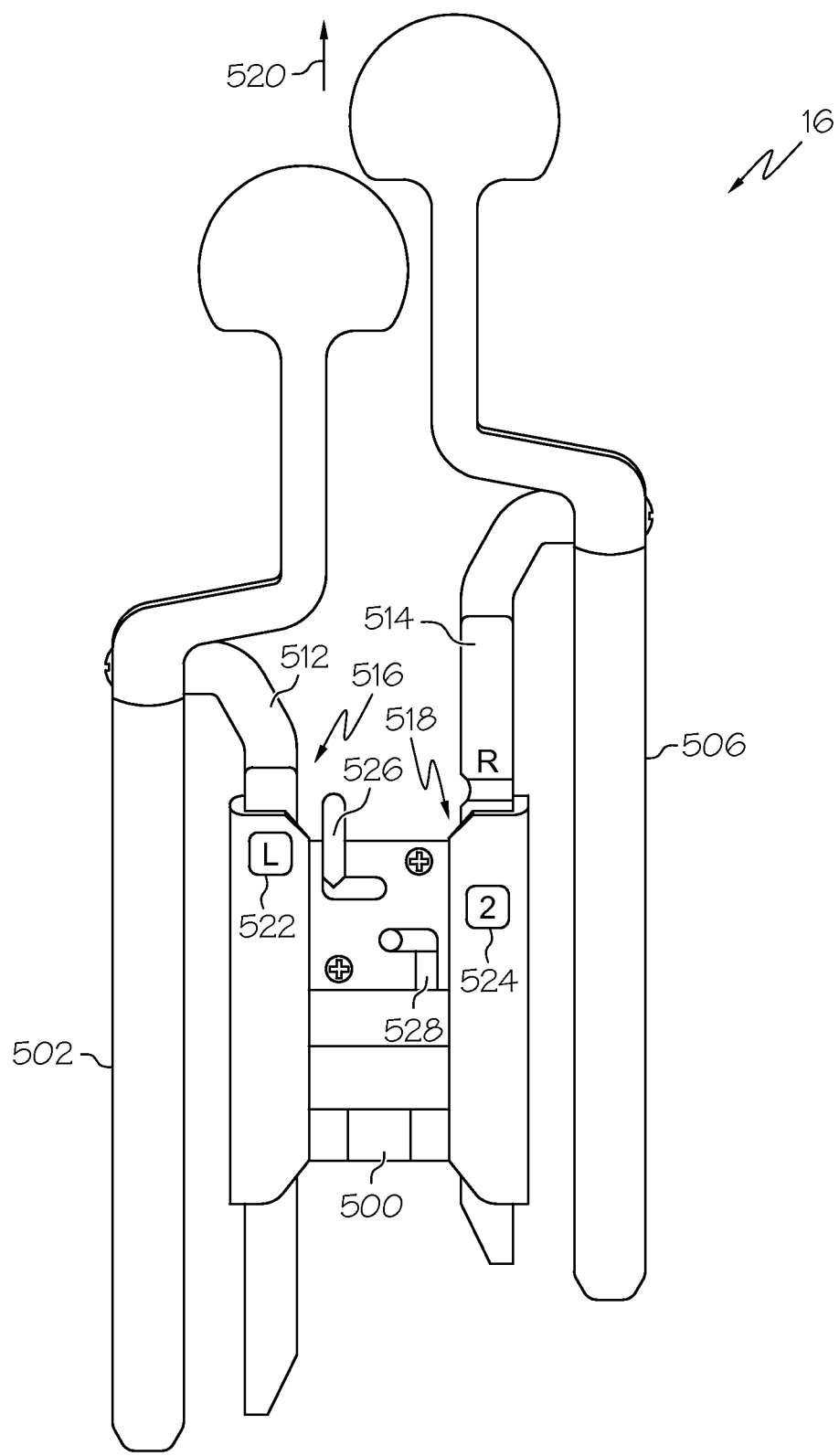
FIG. 29 is a top plan view of the joint distactor of FIG. 27.

As illustrated in FIG. 29, each of the distractor components 502, 506 includes a mounting bar 512, 514, respectively, which is received in a corresponding slot 516, 518 of the cradle 500. The distractor component 502, 506 may be independently moved in an outwardly direction 520 with respect to the cradle 500 by sliding the respective mounting bars 512, 514 in or out off the corresponding slots 516, 518 of the cradle 500. As such, either distractor component 502, 506 may be positioned to extend farther than the other component 502, 504 such that the joint distractor is selectively configured for use with either knee of the patient from either a medial or lateral approach. Additionally, the distractor components 502, 506 may be adjusted and positioned based on the shape and/or size of the sensor housing 30 of the sensor module 12, the shape and size of the patient's knee, and/or other criteria. In some embodiments, as illustrated in FIG. 29, the mounting bars 512, 514 may include indicia to provide a visual indication of the amount of extension for each respective distractor component 502, 506. Such visual indication may be viewable by the orthopaedic surgeon via windows 522, 524 defined in the cradle 500. When the distractor components 502, 506 have been positioned in the desired configuration, the corresponding mounting bars 512, 514 may be locked into position via use of associated locking mechanisms 526, 528. When so locked, the distractor components 502, 506 are restricted from movement relative to the cradle 500.

Figure 30:
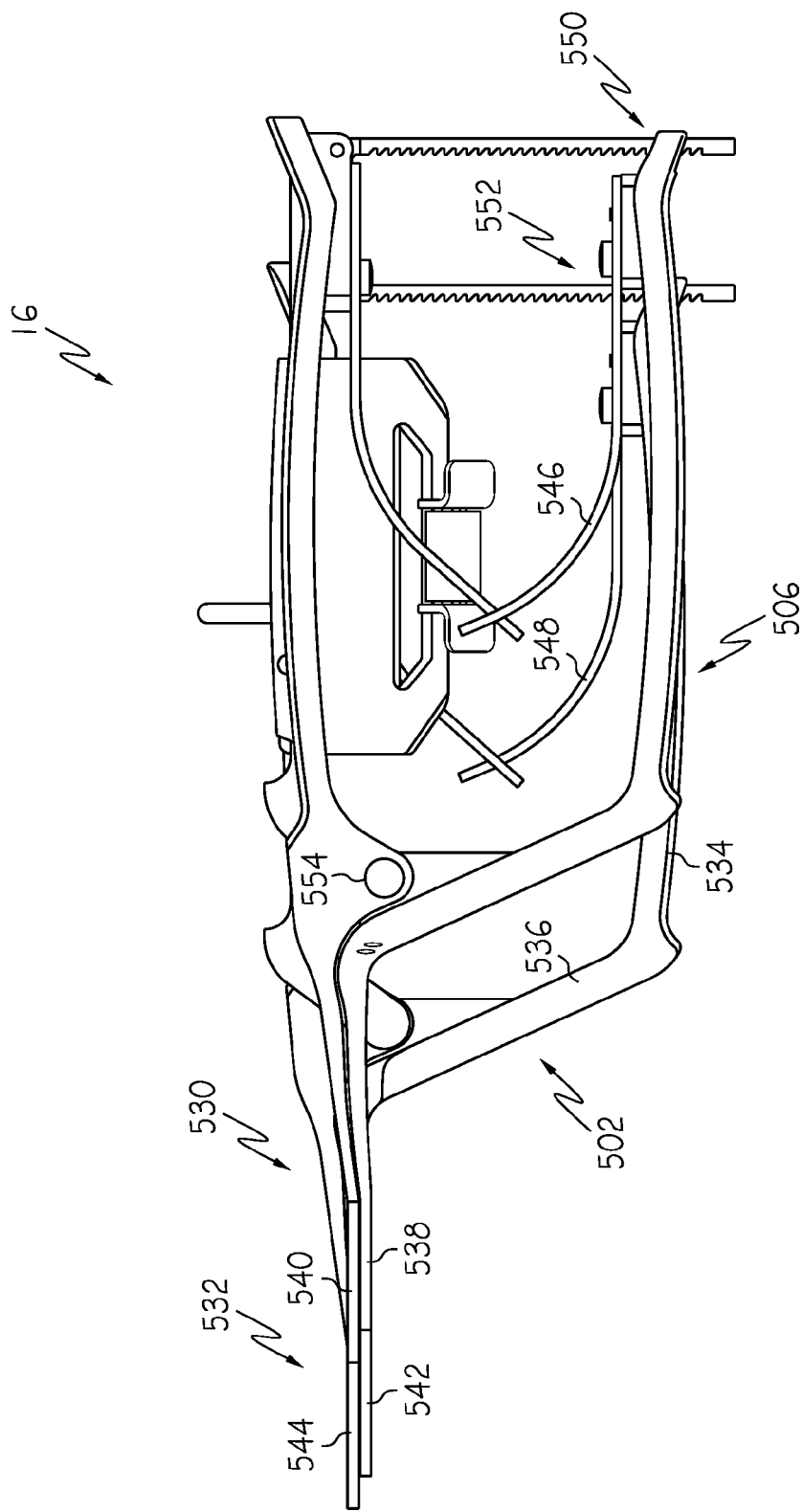
FIG. 30 is a side elevation view of the joint distactor of FIG. 27.

As illustrated in FIG. 30, each distractor component 502, 506 includes a paddle set 530, 532 and a pair of handles 534, 536. The paddle set 530 of the distractor component 502 includes a tibial paddle 538 and a femoral paddle 540. Similarly, the paddle set 532 of the distractor component 506 includes a tibial paddle 542 and a femoral paddle 544. The handles 534 may be operated to move the femoral paddle 540 with respect to the tibial paddle 538 (e.g., upwardly from the tibial paddle 538). Similarly, the handles 536 may be operated to move the femoral paddle 544 with respect to the tibial paddle 542 (e.g., upwardly from the tibial paddle 538). The tibial paddles 538, 542 and the femoral paddles 540, 544 are biased to a closed or contacting position via springs 546, 548, which are illustratively positioned within the handles 534, 536. Additionally, each pair of handles 534, 536 includes an associated locking mechanism 550, 552, respectively, which is operable to lock the handles 534, 536, and thereby the associated tibial paddles 538, 542 and femoral paddles 540, 544, in a selected position.

Figure 20:
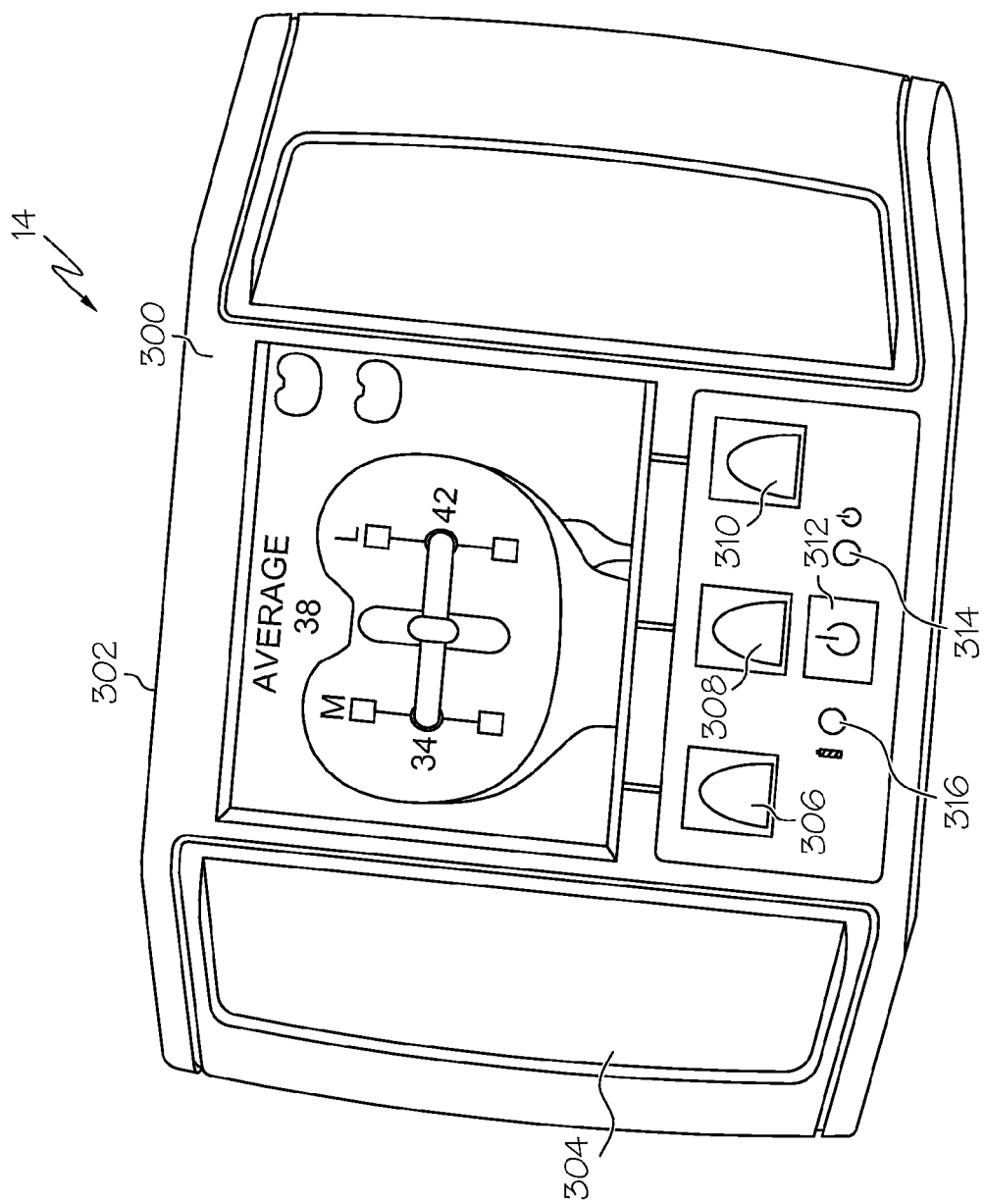
FIG. 20 is a perspective view of one embodiment of a display module of the system of FIG. 1.
Figure 21:
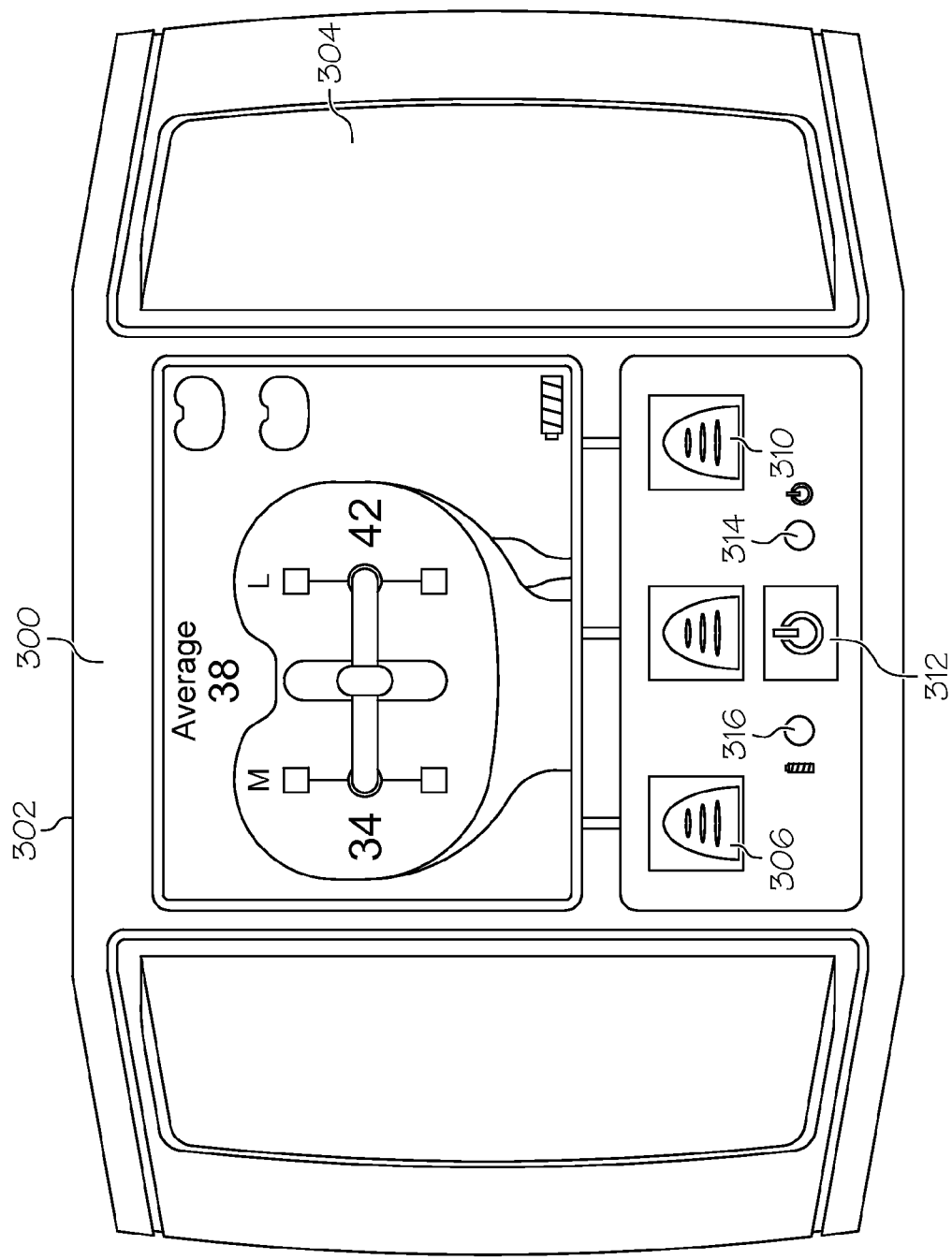
FIG. 21 is a plan view of the display module of FIG. 20.

In use, the sensor module 12 is positioned in the cradle 500 and secured in place via the locking mechanism 510. Depending on which knee of the patient will be operated on, the distractor components 502, 506 may be positioned such that the tibial paddles 538, 542 contact the tibial paddle 34 of the sensor module 12 as illustrated in FIG. 20. It should be appreciated that the tibial paddles 538, 542 have a substantially circular shape generally corresponding to the circular orientation of the pressure sensor 102, 104, 106, 108 and the circular orientation of the pressure sensors 112, 114, 116, 118. The joint distractor 16 and sensor module 12 may then be inserted into the patient's joint (e.g., between the proximal end of the patient's tibia and the distal end of the patient's femur). The joint distractor 16 may be subsequently used to distract the patient's joint and, in response to the joint force applied to the tibial paddle 34, the sensor module 12 displays the medial-lateral balance of the joint forces of the joint at the selected degree of distraction. In this way, an orthopaedic surgeon may use the distractor 16 and sensor module 12 to adjust and monitor the relative joint forces of the patient's joint during the performance of the orthopaedic surgical procedure.

Figure 31:
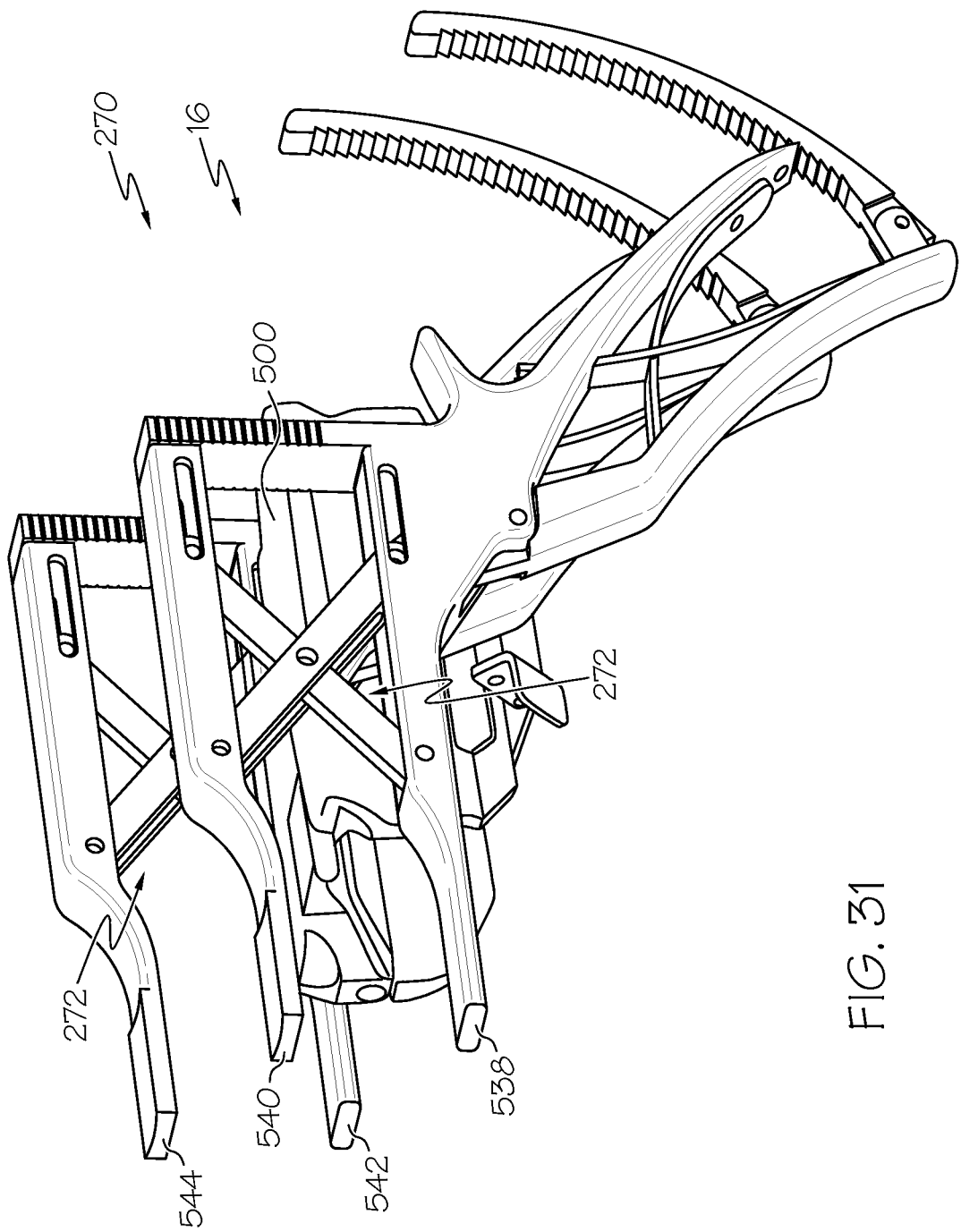
FIG. 31 is a perspective view of another embodiment of a joint distactor of the system of FIG. 1.

In the illustrative embodiment of FIGS. 27-30, the femoral paddles 540, 544 pivot with respect to the tibial paddles 538, 542 about a pivot joint 554 (see FIG. 30). As such, the femoral paddles 540, 544 are moved to an oblique orientation relative to the tibial paddles 538, 542 during use. However, in another embodiment as illustrated in FIG. 31, the distractor 16 may include a four-bar linkage 272 or other mechanism configured such that the femoral paddles 540, 544 are moved to a substantially parallel orientation relative to the tibial paddles 538, 542 during use. That is, in such embodiments, the femoral paddles 540, 544 and the tibial paddles 538, 542 remain substantially parallel to each other as the femoral paddles 540, 544 are moved away from the tibial paddles 538, 542. As such, it should be appreciated that the distractor components 502, 506 are but one illustrative embodiment of distractor components to which the cradle 500 may be coupled and, in other embodiments, the cradle 500 may be coupled to other types of distractor components configured to operate in manners similar to or different from the distractor components 502, 506.

Figure 32:
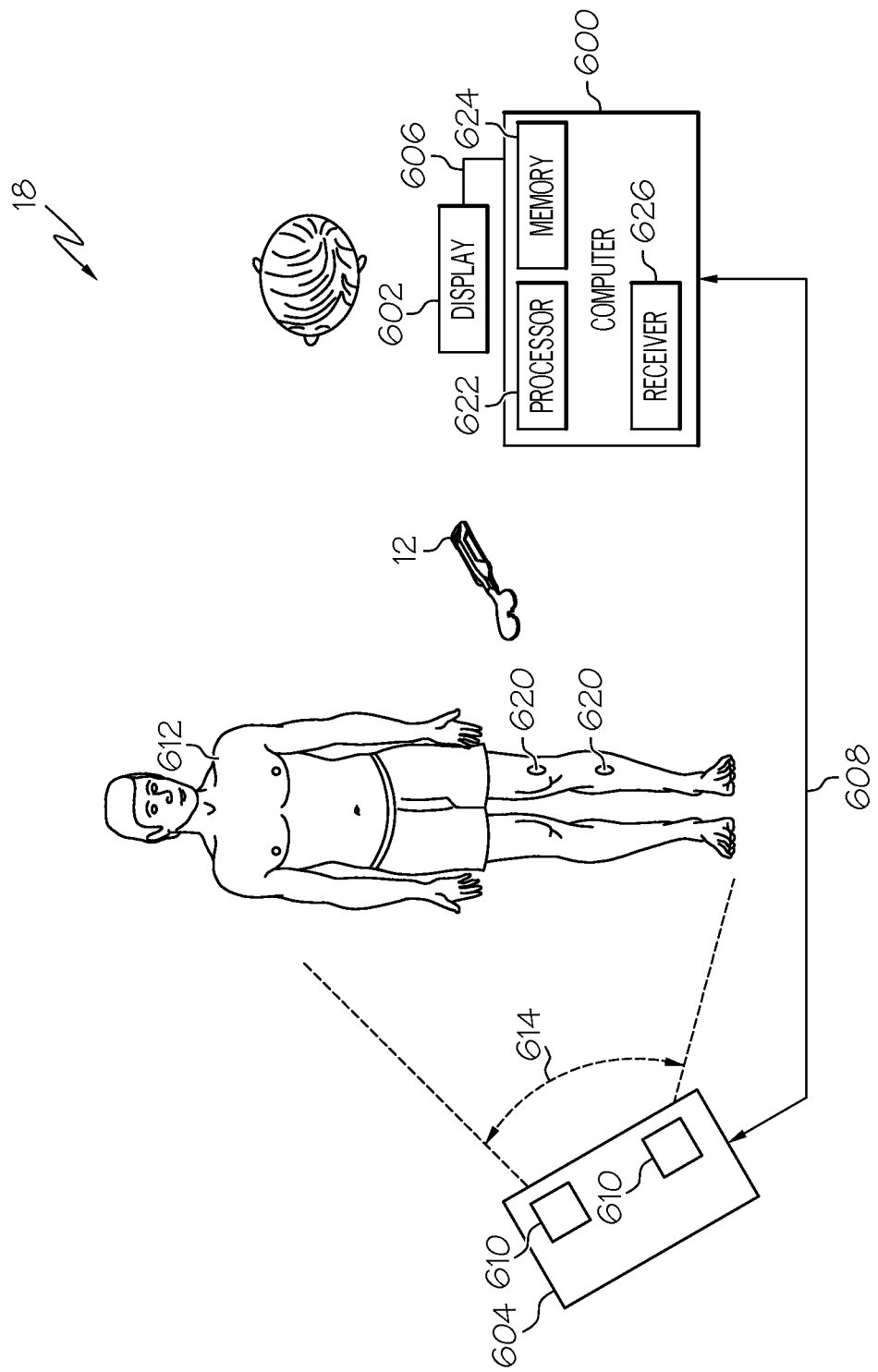
FIG. 32 is a simplified block diagram of one embodiment of a computer assisted surgery system of the system of FIG. 1.

Referring now to FIGS. 32-35, in some embodiments, the sensor module 12 may be configured for use with the computer assisted orthopaedic surgery (CAOS) system 18. In such embodiments, the sensor module 12 is configured to transmit the joint force data to the system 18. As illustrated in FIG. 32, the computer assisted orthopaedic surgery (CAOS) system 18 includes a computer 600, a display 602, and a camera unit 604. The computer 600 is communicatively coupled to the display 602 via signal paths 606 and to the camera unit 604 via signal paths 608. The signal paths 606, 608 may be embodied as any type of signal paths capable of facilitating electrical communication between the computer 600 and the display 602 and the computer 600 and the camera unit 604, respectively. For example, the signal paths may be embodied as any number of wires, printed circuit board traces, via, bus, intervening devices, and/or the like.

The display 602 may be embodied as any type of device such as a liquid crystal display monitor, a cathode ray tube (CRT) display monitor, or the like. Additionally, in some embodiments, the display 602 may be embodied as a "heads-up" display. In such embodiments, the signal path 606 may be embodied as a wired or wireless signal path. The camera unit 604 includes two or more cameras 610, which are positioned such that reflective arrays 620 coupled to the relevant bones of a patient 612 are in the field of view 614 of the cameras 610.

The computer 600 includes a processor 622, a memory device 624, and a receiver or receiver circuitry 626. The processor 622 may be embodied as any type of processor configurable to perform the functions described herein. For example, the processor 622 may be embodied as a separate integrated circuit or as a collection of electronic devices. Additionally, the processor may be a single or multi-core processors. Although only a single processor 622 is illustrated in FIG. 32, it should be appreciated that in other embodiments, the computer 600 may include any number of additional processors. The memory device 624 may be embodied read-only memory devices and/or random access memory devices. For example, the memory device 624 may be embodied as or otherwise include electrically erasable programmable memory devices (EEPROM), dynamic random access memory devices (DRAM), synchronous dynamic random access memory devices (SDRAM), double-data rate dynamic random access memory devices (DDR SDRAM), and/or other volatile or non-volatile memory devices. Additionally, although only a single memory device is illustrated in FIG. 32, in other embodiments, the computer 600 may include additional memory devices.

The receiver circuitry 626 may be configured to use any type of wireless communication protocol, standard, or technologies to receive the joint force data from the sensor module 12. For example, as discussed above in regard to the sensor module 12, the computer 600 may be configured to communicate using a wireless networking protocol, a cellular communication protocol such as a code division multiple access (CDMA) protocol, a Bluetooth® protocol, or other wireless communication protocol, standard, or technology to communicate with the sensor module 12.

In use, the computer assisted orthopaedic surgery (CAOS) system 18 is configured to provide surgical navigation by tracking and displaying the position of the patient's relevant bony anatomy (e.g., the patient's tibia and femur) to which the reflective arrays 620 are coupled and provide an amount of surgical procedure walk-through. Additionally, the computer assisted orthopaedic surgery (CAOS) system 18 is configured to receive the joint force data from the sensor module 12 and display the joint force data or other indicia of the joint forces of the patient's joint on the display 602.

Figure 33:
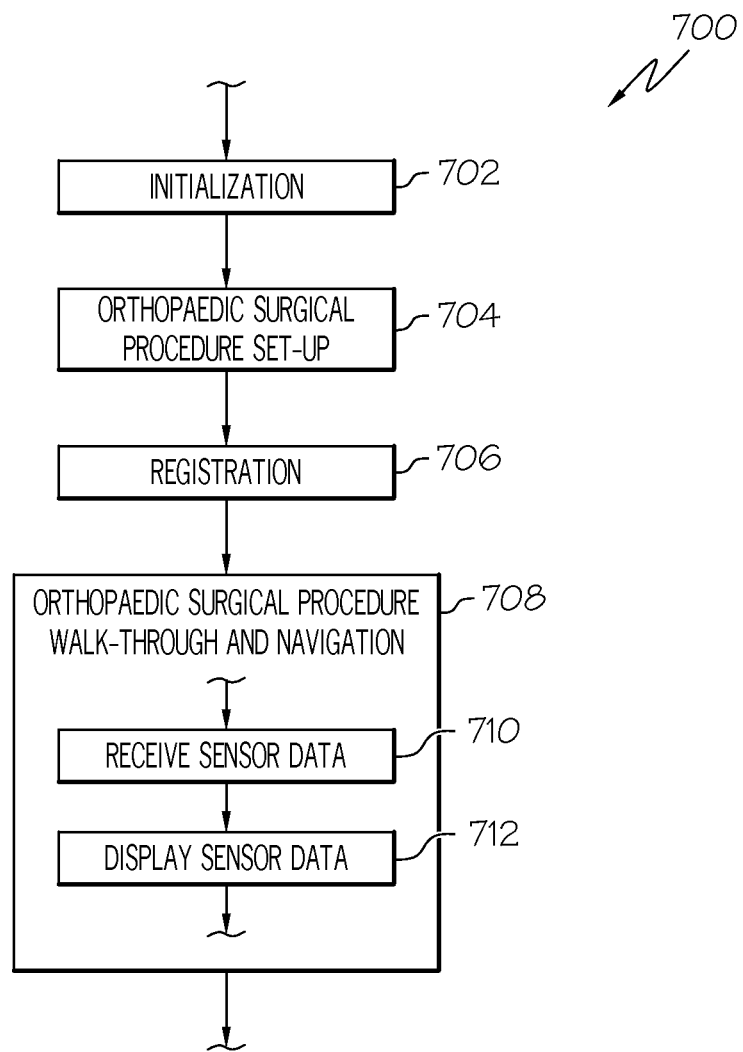
FIG. 33 is a simplified flow diagram of one embodiment of a method for performing an orthopaedic surgical procedure using the computer assisted surgery system of FIG. 32.

To do so, the computer 600 may execute a method 700 for performing an orthopaedic surgical procedure as illustrated in FIG. 33. The method 700 begins with block 702 in which the system 18 is initialized. For example, in block 702, the computer 600 may perform any number of system checks, clear any registers of the processor 622, and/or perform other initialization and/or integrity checks. Additionally, any number of settings, preferences, and calibrations of the CAOS system 18 may be established and performed in block 702. For example, the video settings of the display 602 may be selected, the language displayed by the computer 600 may be chosen, and the touch screen of the display device 602, if applicable, may be calibrated in block 702.

In block 704, the selections and preferences of the orthopaedic surgical procedure are chosen by the surgeon. Such selections may include the type of orthopaedic surgical procedure that is to be performed (e.g., a total knee arthroplasty), the type of orthopaedic implant that will be used (e.g., make, model, size, fixation type, etc.), the sequence of operation (e.g., the tibia or the femur first), and the like. Once the orthopaedic surgical procedure has been set up in block 704, the bones of the patient are registered in block 706. To do so, the reflective arrays 620 are coupled with the relevant bones of the patient (e.g., the tibia and femur of the patient). Additionally, the contours of such bones are registered using an appropriate registration tool. To do so, a pointer end of such tool is touched to various areas of the bones to be registered. In response to the registration, the computer 600 displays rendered images of the bones wherein the location and orientation of the bones are determined based on the reflective arrays coupled therewith and the contours of the bones are determined based on the registered points. Additionally, one or more surgical tools may be registered with the computer assisted orthopaedic surgery (CAOS) system in block 706.

Once the pertinent bones have been registered in block 706, the computer 600, in cooperation with the camera unit 604, displays the images of the surgical steps of the orthopaedic surgical procedure and associated navigation data (e.g., location of surgical tools) in block 708. To do so, the process step 708 may include any number of sub-steps in which each surgical procedure step is displayed to the orthopaedic surgeon in sequential order along with the associated navigational data. Additionally, in block 710 the computer 600 receives joint force data from the sensor module 12. As discussed above, the joint force data is indicative of the joint force of the patient's knee as indicated by the sensor signals generated by the sensor array 90 of the sensor module 12.

In block 712, the computer 600 displays the joint force data or other data derived therefrom that is indicative of the joint forces of the patient's joint on the display 602. The computer 600 may be configured to determine any one or more joint force values based on the joint force data in block 712. For example, similar to the hand-held display module 14, the computer 600 may be configured to determine a medial joint force value and a lateral joint force value based on the joint force data received in block 710. Again, such medial joint force value is based on the sensor signals received from the pressure sensors 102, 104, 106, 108, 120, 124 and the lateral joint force value is based on the sensor signals received from the pressure sensors 112, 114, 116, 118, 122, 126. The computer 600 may also determine an average medial/lateral force value based on the medial joint force value and the lateral joint force value. In such embodiments, the medial joint force value, the lateral joint force value, and the average joint force value are subsequently displayed on the display 602 in block 712. In addition, the computer 600 may be configured to determine the medial-lateral and/or anterior-posterior balance of the joint forces based on the joint force data and display indicia of joint force balance on the display 602 in a manner similar to the hand-held display module 14. For example, the computer 600 may present displays similar to the displays 450, 452, 454 illustrated in and described above in regard to FIGS. 24, 25, and 26, respectively. in block 412.

Figure 34:
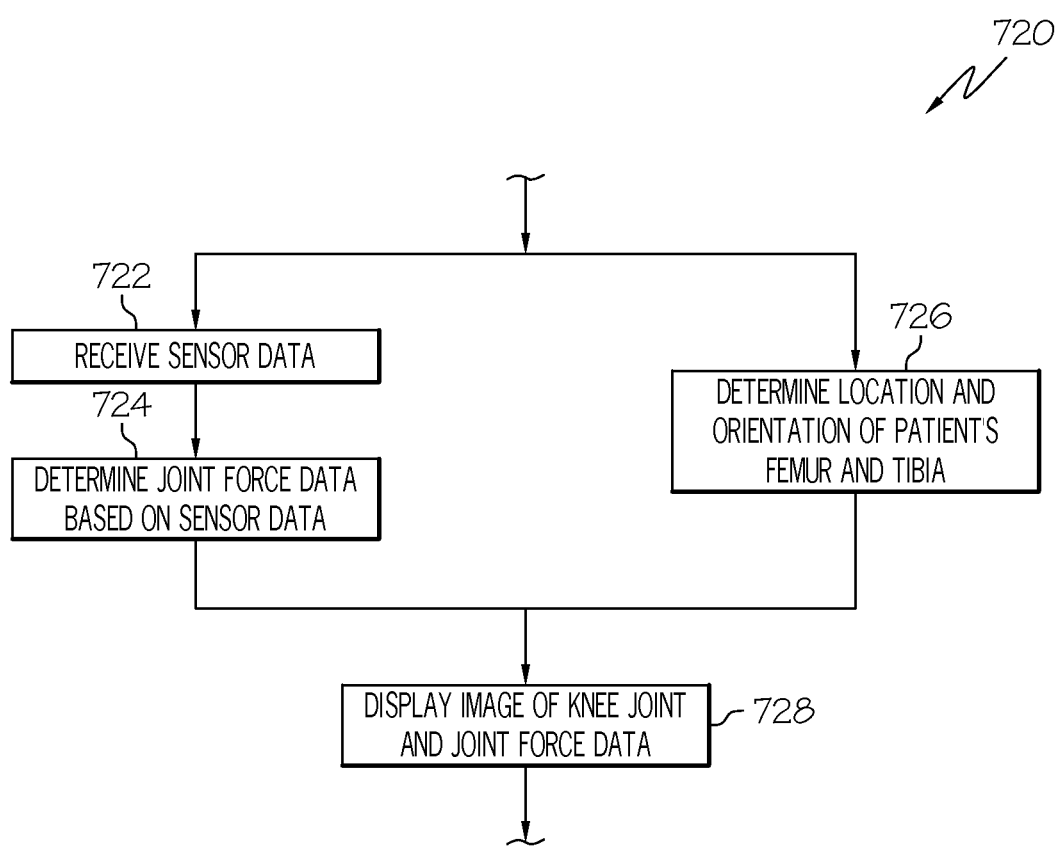
FIG. 34 is a simplified flow diagram of one embodiment of a method for determining and displaying navigation and joint force data that may be executed by the computer assisted surgery system of FIG. 32.

In some embodiments, the computer assisted orthopaedic surgery (CAOS) system 18 may be configured to determine and display joint force data on the display 602 in association with the navigation data. For example, the computer 600 may execute a method 720 for displaying joint force data in association with navigation data as illustrated in FIG. 34. The method 720 includes a block 722 in which the computer 600 receives joint force data from the sensor module 12. Again, the joint force data is indicative of the joint force of the patient's knee as indicated by the sensor signals generated by the sensor array 90 of the sensor module 12. In block 724, the computer 600 determines the medial, lateral, and/or average joint force values based on the joint force data received in block 722.

Contemporaneously with the determination of the joint force values in block 722, the computer 600 determines the location and orientation of the patient's relevant bones, such as the patient's femur and tibia in those embodiments wherein the patient's knee is undergoing an orthopaedic surgical procedure, in block 724. Subsequently, in block 728, the computer 600 displays the joint force values determined in block 722 and the image of the knee joint in block 728. As such, the computer 600 may be used to display, for example, the flexion and extension gaps of the medial and lateral condyles of the patient's knee and contemporaneously display the associated medial, lateral, and/or average joint force values of the patient's knee. By monitoring the flexion and extension gaps and the associated joint force values, the orthopaedic surgeon may determine the appropriate amount of gap or joint force for a particular orthopaedic procedure.

Additionally, in some embodiments, the computer 600 may also be configured to determine other anatomical data based on the orientation and position of the patients bones determined in block 726 and display such anatomical data along with the associated joint force values. For example, in one embodiment, the computer 600 is configured to determine the varus/valgus angle of the patient's knee and display the associated medial and lateral force values. Additionally, the computer 600 may be configured to determine the loaded condyle based on the medial and lateral force values and identify the loaded condyle to the orthopaedic surgeon on the display 602. Further, in some embodiments, the computer 600 may be configured to store the anatomical data, the joint force values, and/or other surgical data such as the implant type size, patient identification data, and;/or the like in association with each other in the memory device 624 or other storage device.

Figure 35:
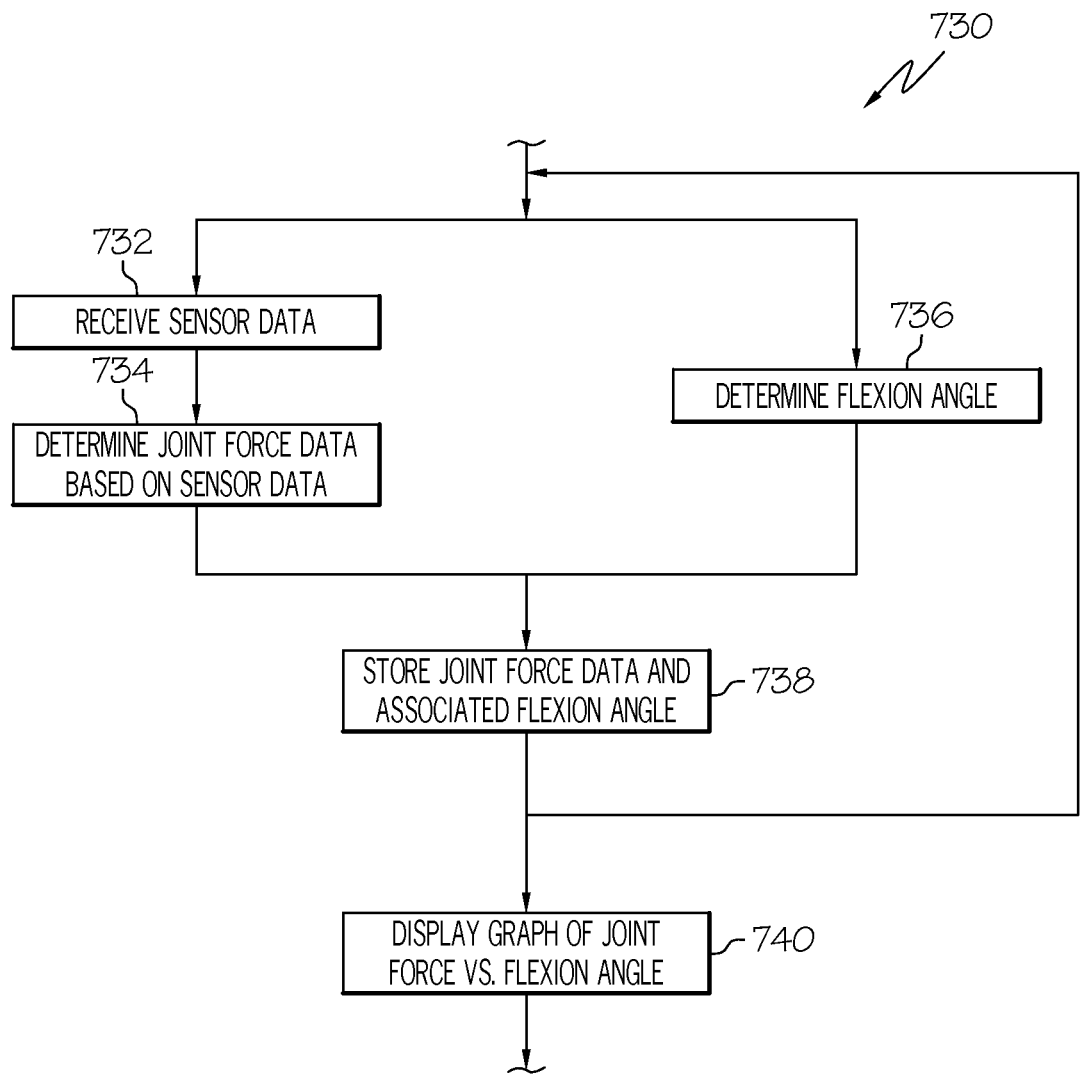
FIG. 35 is a simplified flow diagram of one embodiment of a method for determining and displaying flexion angle and force data of a patient's joint that may be executed by the computer assisted surgery system of FIG. 32.

The computer 600 may also be configured to determine and display a graph of flexion angle and associated joint force values in some embodiments. To do so, the computer 600 executes a method 730 as illustrated in FIG. 35. The method 730 includes a block 732 in which the computer 600 receives joint force data from the sensor module 12. Again, the joint force data is indicative of the joint force of the patient's knee as indicated by the sensor signals generated by the sensor array 90 of the sensor module 12. In block 734, the computer 600 determines the medial, lateral, and/or average joint force values based on the joint force data received in block 732.

Contemporaneously with the determination of the joint force values in block 732, the computer 600 determines the flexion angle of the patient's knee in block 736. To do so, the computer 600 determines the relative location of the patient's tibia and femur and determines the flexion angle defined therebetween based on these locations. In block 738, the computer 600 stores the joint force data determined in block 734 and the flexion angle data determined in block 738. The method repeats through blocks 732, 734, 736 to collect data and each, or every predetermined, flexion angle within a desired range of flexion. After such data has been collected, the method 730 advances to block 740 in which the computer

600 displays a graph of joint force values versus flexion angle. Such graph may include medial and lateral joint force values or may include an average joint force values depending on the preference of the orthopaedic surgeon.

Figure 36:
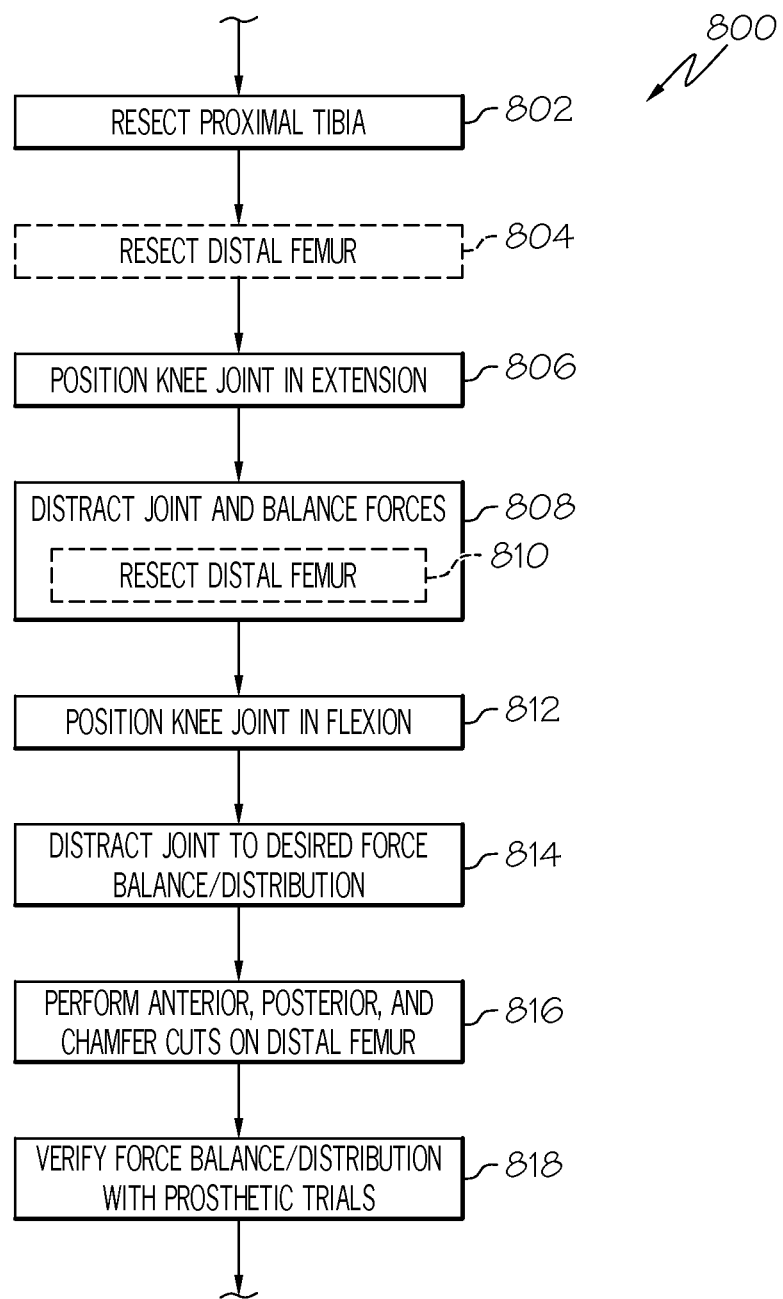
FIG. 36 is a simplified flow diagram of one embodiment of a method for performing an orthopaedic surgical procedure using the system of FIG. 1.

Referring now to FIGS. 36-41, as discussed above, the sensor module 12 may be used during the performance of an orthopaedic surgical procedure to monitor the relative medial-lateral balance of the patient's joint forces. For example, a surgical method 800 for performing a total knee arthroplasty procedure using the sensor module 12 is illustrated in FIG. 36. The method 800 begins with block 802 in which the proximal tibia 900 of the patient is resected. By resecting the patient's tibia 900, a resected planar surface or plateau is established on the proximal end of the tibia. In some embodiments, such as those embodiments wherein the computer assisted orthopaedic surgery (CAOS) system 18 is not used, the distal end of the patient's femur 902 may be resected in block 804.

Figure 37:
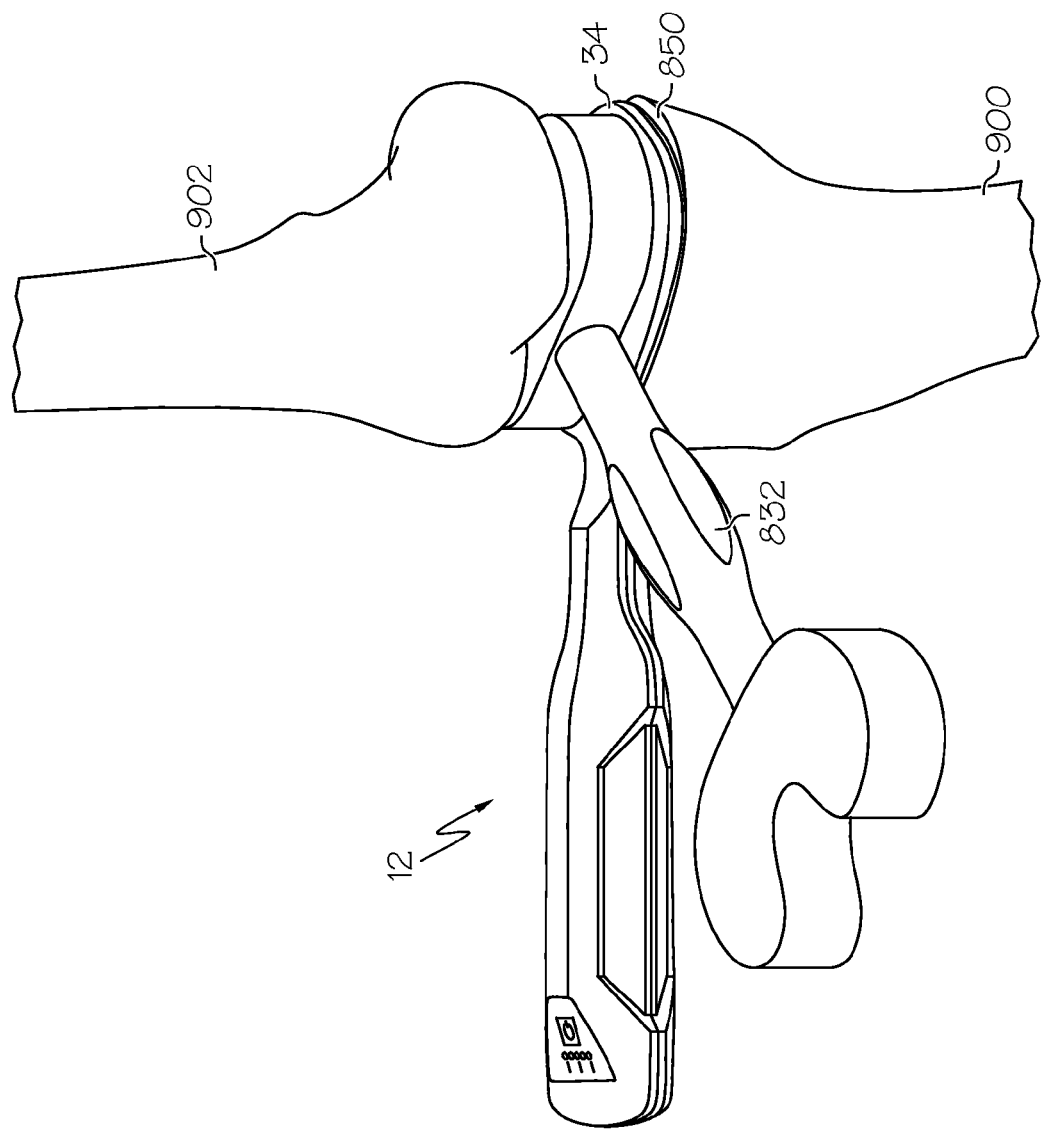
FIG. 37 is a perspective view of a patient's joint in extension during an orthopaedic surgical procedure using the sensor module of FIG. 2.

In block 806, the patient's knee is placed in extension. Subsequently, in block 808, the patient's knee is distracted while in extension and the joint forces are balanced. To do so, the orthopaedic surgeon may place the tibial paddle 34 of the sensor module 12 in the patient's knee joint. In particular, the tibial paddle 34 is placed on the resected plateau 850 of the patient's proximal tibia as illustrated in FIG. 37. The tibial paddle 34 may be placed in contact with the patient's tibia or may be placed on a membrane or other intervening member. As shown in FIG. 37, a spacer block 832 may be used to distract the patient's knee in extension a desired amount. Alternatively, the sensor module 12 may be coupled to the joint distractor 16, which may be inserted into the patient's knee joint and operated to distract the joint to the desired amount. Typically, the patient's knee joint is distracted in extension an amount necessary to establish a generally rectangular joint gap (i.e., the resected plateau 850 of the patient's tibia is approximately parallel with the resected distal end of the patient's femur).

Once a generally rectangular joint gap is established, the orthopaedic surgeon may balance the medial and lateral joint forces. To do so, the orthopaedic surgeon may perform a ligament release or balancing procedure to reduce the medial or lateral force of the patient's knee. While so doing, the orthopaedic surgeon may monitor the display 50, 52 of the sensor module 12 and/or the hand-held display module 14 to determine which side to release and when the medial and lateral forces are approximately equal (e.g., when the middle light emitting diode 84 is illuminated). Of course, the orthopaedic surgeon may decide that an alternative joint force balance, such as a 45%/55% medial-lateral joint force balance, is desirable for the particular patient based on such criteria as, for example, the age of the patient, the gender of the patient, the extent of soft tissue damage of the patient's joint, the extent of pre-operative deformity of the patient's joint, etc. Additionally, in some embodiments, such as those embodiments wherein the computer assisted orthopaedic surgery (CAOS) system 18 is used, the distal end of the patient's femur 902 may be resected in block 810.

After the orthopaedic surgeon has properly balanced the medial-lateral joint forces of the patient's joint in extension, the patient's joint is placed in flexion in block 812. Subsequently, in block 814, the patient's knee is distracted while in flexion to the desired balance of joint forces. To do so, the orthopaedic surgeon may again place the tibial paddle 34 of the sensor module 12 on the resected plateau 850 of the patient's proximal tibia 900. The tibial paddle 34 may be placed in contact with the patient's tibia or may be placed on a membrane or other intervening member. The orthopaedic surgeon may distract the patient's knee using, for example, the distractor 16, 560, or other distractor to distract each condyle of the patient's femur differing amounts until the medial and lateral joint forces are approximately equal. By, equalizing the medial and lateral joint forces, the rotation of the femur is established.

Figure 38:
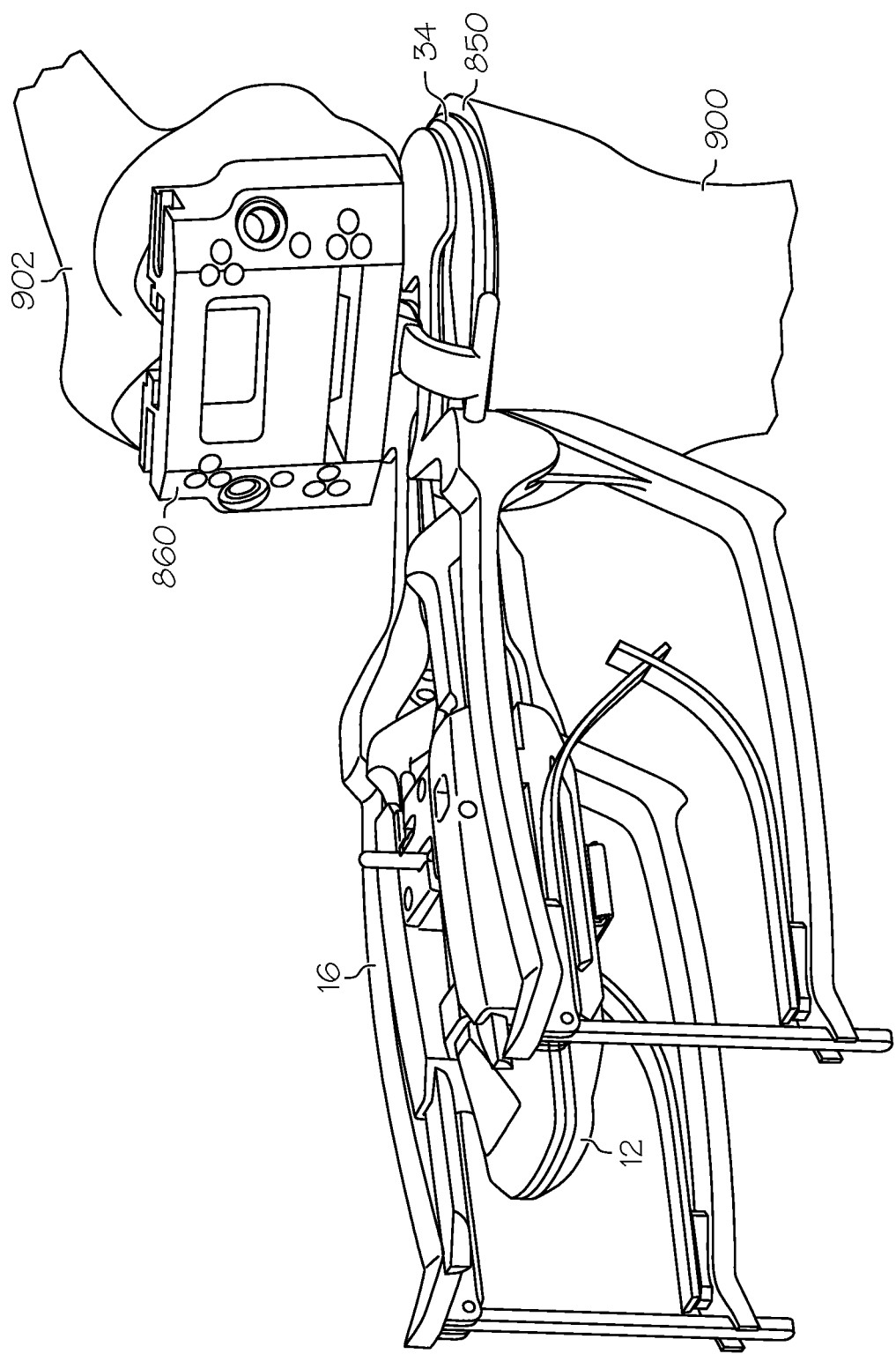
FIG. 38 is a perspective view of a patient's joint during an orthopaedic surgical procedure using the distractor and sensor module of FIG. 20.

After the patient's joint has been distracted to achieve the desired medial-lateral joint balance in block 814, a number of additional resectioning cuts are performed on the patient's distal femur 902 in block 816. To do so, as illustrated in FIG. 38, a cutting block 860 may be coupled to the joint distractor 16 and used to perform an anterior femoral cut, a posterior femoral cut, and/or chamfer cuts on the patient's distal femur 902 while the patient's joint is distracted in flexion. In one particular embodiment, the cutting block 860 is positioned such that the anterior and posterior femoral cuts are substantially parallel to the tibial cut while the patient's knee is distracted in flexion as discussed above. In other embodiments, the cutting block 860 may be positioned such that the angle of the anterior and posterior femoral cuts correspond to particular angles of the intended implant. As such, the anterior and posterior femoral cuts are performed with the femur rotated to the desired position. The position of the cutting block 860 may also be adjusted anteriorly or posteriorly to set the flexion gap for the orthopaedic implant.

Figure 39:
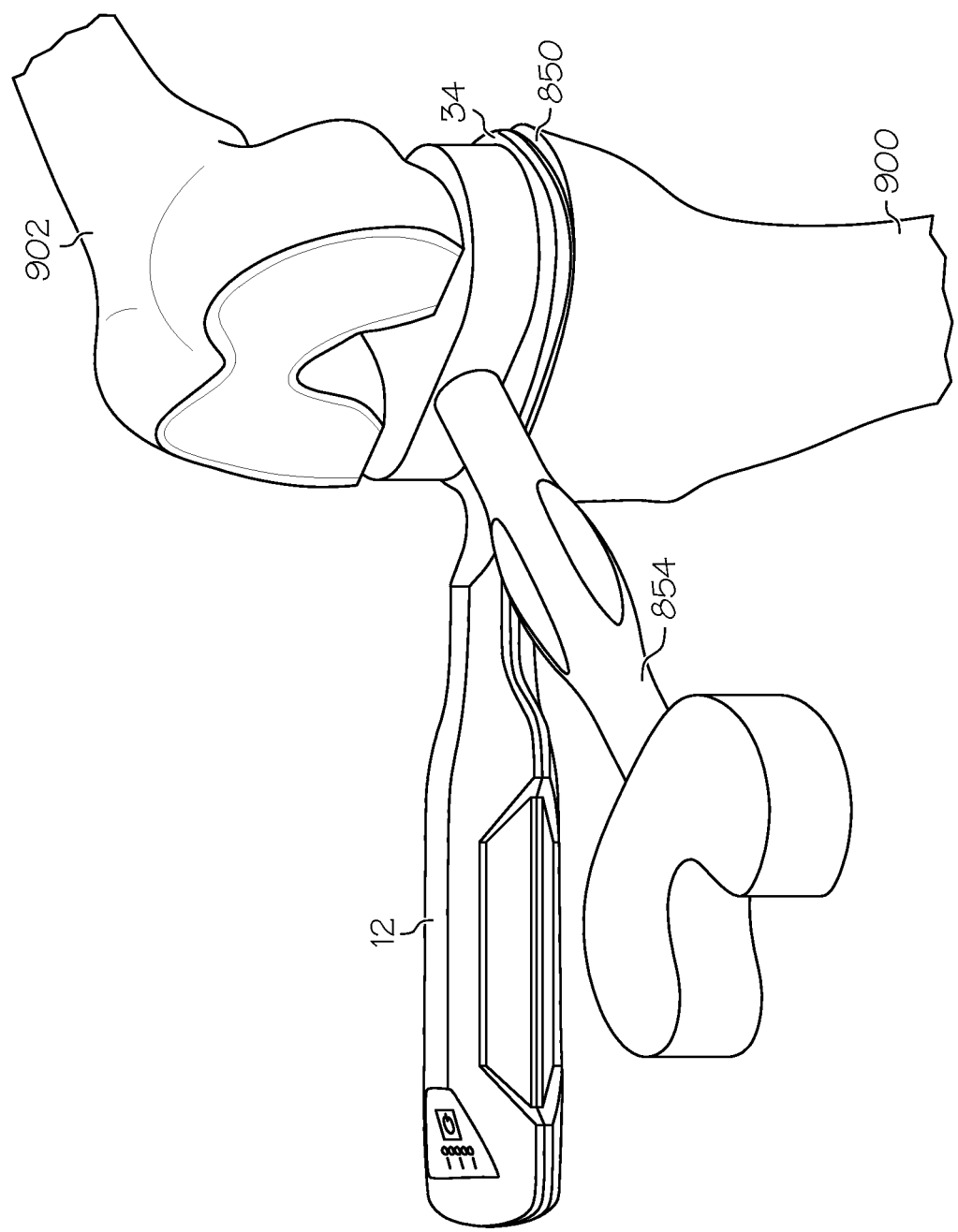
FIG. 39 is another perspective view of a patient's joint in flexion during an orthopaedic surgical procedure using the sensor module of FIG. 2.

Alternatively, in some embodiments, the rotation of the femur in flexion is predetermined based on anatomical references such as the posterior condyles, Whiteside's line, and/or the transepicondylar axis. The anterior femoral cut, a posterior femoral cut, and/or chamfer cuts are performed on the patient's distal femur 902 based on the predetermined rotation of the femur. As illustrated in FIG. 39, a spacer block 854 may be used to check or verify such femoral cuts. Additionally, ligamentous release may be used by the surgeon to balance or define the desired medial-lateral joint forces. In such embodiments, the orthopaedic surgeon may also verify that ligament releases performed in flexion do not adversely affect the joint force balance in extension.

Figure 40:
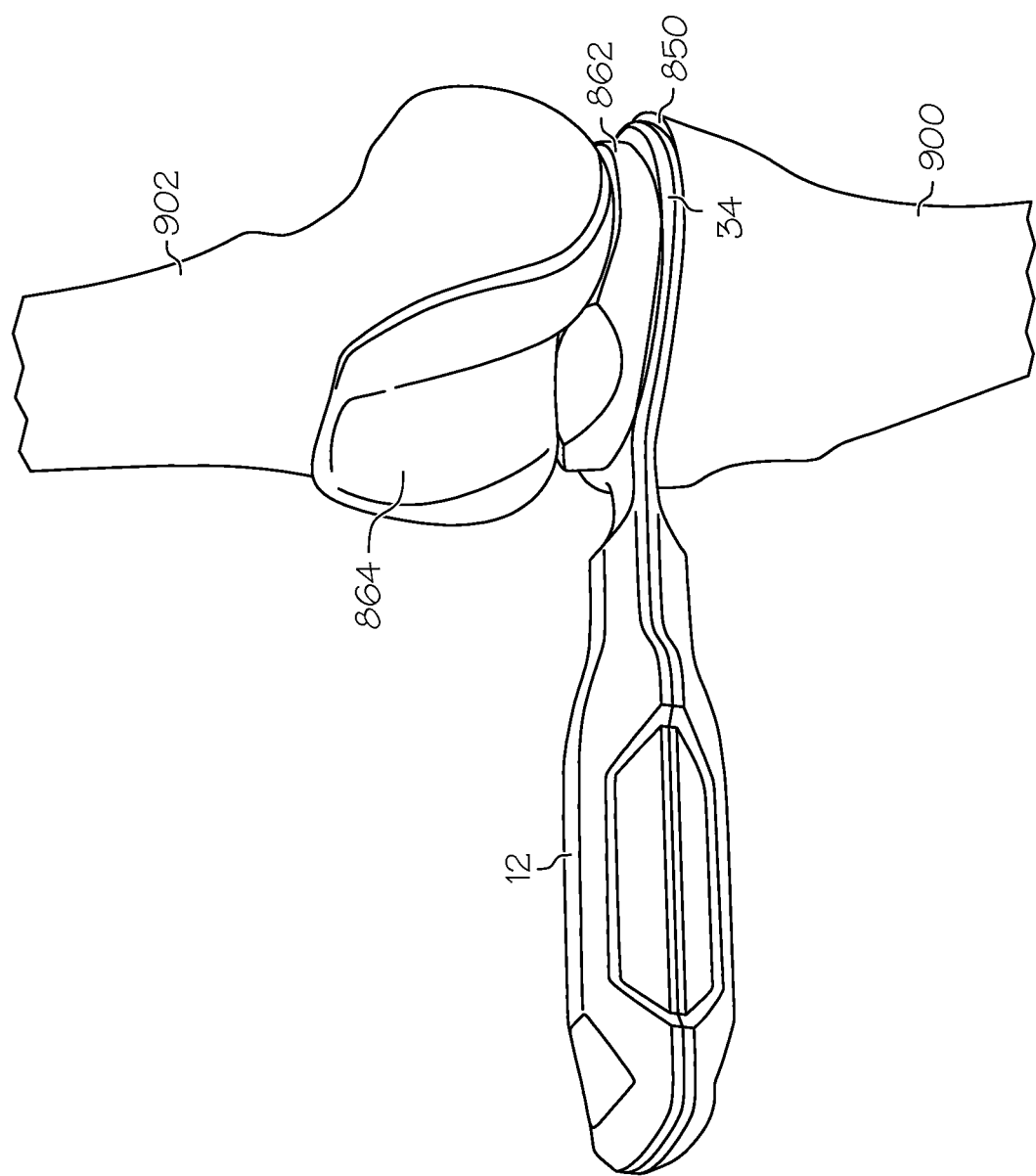
FIG. 40 is another perspective view of a patient's joint in extension during an orthopaedic surgical procedure using the sensor module of FIG. 2.

After the final resectioning of the patient's distal femur is complete, the joint force balance of the patient's knee joint is verified in block 818. To do so, the orthopaedic surgeon may place the tibial paddle 34 of the sensor module 12 on the resected plateau 850 of the patient's proximal tibia 900 as illustrated in FIGS. 40 and 41. A trial tibial insert or bearing 862 may be placed on the tibial paddle 34 and a trial femoral component may be temporarily coupled to the distal end of the patient's femur 902. The patient's knee joint may then be moved through various degrees of flexion as illustrated in FIG. 41 while the orthopaedic surgeon monitors the associated joint force balance as indicated by the displays 50, 52 of the sensor module 12 to verify that the desired joint for balance is maintained throughout flexion of the patient's joint.

The system 10 has been described above in regard to the measuring, determining, and displaying of joint forces. Such joint forces generally correspond to the joint pressure of the patient's joint over a defined area. As such, it should be appreciated that in other embodiments the sensor module 12, the hand-held display module 14, and the computer assisted surgery system 18 may be configured to measure, determine, and display the pressure of the patient's relative joint in addition to or alternatively to the patient's joint force. For example, in one embodiment, the pressure of the patient's joint may be determined based on the known area of each sensor of the pressure sensors or sensor elements 100 of the sensor array 90.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the devices, systems, and methods described herein. It will be noted that alternative embodiments of the devices, systems, and methods of the present disclosure may not include all of the features described yet still benefit from at least some of the advantages of such features. Those of ordinary skill in the art may readily devise their own implementations of the devices, systems, and methods that incorporate one or more of the features of the present invention and fall within the spirit and scope of the present disclosure as defined by the appended claims.

The invention claimed is:

1. A method for performing an orthopaedic surgical procedure on a knee joint of a patient, the method comprising:
    resecting a proximal end of a patient's tibia to create a resected surface of the patient's tibia;
    positioning a tibial paddle of a sensor module on the resected surface of the patient's tibia, the tibial paddle including a sensor array and having an upper tibial paddle housing with a substantially flat surface,
    distracting the patient's knee joint while the knee joint is in extension, wherein distracting the patient's knee joint comprises positioning a joint distractor in the patient's knee joint such that a medial tibial paddle of the joint distractor and a lateral tibial paddle of the joint distractor each contacts the upper tibial paddle housing of the sensor module;
    monitoring a display of the sensor module, the display providing a visual indication of the medial-lateral joint force balance of the patient's knee joint; and
    performing a balancing procedure to adjust the medial-lateral balance as indicated by the display of the sensor module.

2. The method of claim 1, wherein distracting the patient's knee joint comprises coupling the sensor module to the joint distractor.

3. The method of claim 1, wherein distracting the patient's knee joint comprises:
    moving a medial femoral paddle of the joint distractor away from a corresponding medial tibial paddle of the joint distractor medial femoral paddle, and
    moving a lateral femoral paddle of the joint distractor away from a corresponding lateral medial paddle of the joint distractor.

4. The method of claim 3, wherein distracting the patient's knee joint comprises establishing a generally rectangular joint gap between the patient's proximal tibia and a resected distal end of the patient's femur such that the resected surface of the patient's tibia is approximately parallel with the resected distal end of the patient's femur.

5. The method of claim 1, wherein distracting the patient's knee joint comprises positioning a spacer block on the tibial paddle of the sensor module.

6. The method of claim 1, wherein performing a balancing procedure comprises performing a ligament release on the patient's soft tissue.

7. The method of claim 1, further comprising:
    positioning the knee joint in flexion, and
    distracting the knee joint in flexion to a predetermined medial-lateral balance value by monitoring the display of the sensor module.

8. The method of claim 7, further comprising performing a number of resectioning cuts on the distal end of the patient's femur while the knee joint is distracted in flexion.

9. The method of claim 7, wherein distracting the knee joint in flexion comprises positioning a joint distractor in the patient's knee joint such that a medial tibial paddle of the joint distractor and a lateral tibial paddle of the joint distractor each contact the tibial paddle of the sensor module.

10. The method of claim 9, wherein distracting the patient's knee joint comprises coupling the sensor module to the joint distractor.

11. A method for performing an orthopaedic surgical procedure on a knee joint of a patient, the method comprising:
    resecting a proximal end of a patient's tibia to create a resected surface of the patient's tibia;
    positioning a tibial paddle of a sensor module on the resected surface of the patient's tibia, the tibial paddle including a sensor array positioned therein and having an upper tibial paddle housing with a substantially flat surface,
    distracting the patient's knee joint to establish a generally rectangular joint gap between the patient's proximal tibia and a resected distal end of the patient's femur such that the resected surface of the patient's tibia is approximately parallel with the resected distal end of the patient's femur, wherein distracting the patient's knee joint comprises positioning a joint distractor in the patient's knee joint such that a medial tibial paddle of the joint distractor and a lateral tibial paddle of the joint distractor each contacts the upper tibial paddle housing of the sensor module;
    monitoring a visual indication of the relative balance of a medial joint force and a lateral joint force of the patient's knee joint displayed on the display of the sensor module; and
    performing a balancing procedure on the patient's knee joint until the medial joint force and the lateral joint force are within a first predetermined percentage of each other as indicated on the visual indication displayed on the display module.

12. The method of claim 11, wherein distracting the patient's knee joint comprises coupling the sensor module to the joint distractor.

13. The method of claim 11, wherein distracting the patient's knee joint comprises:
    moving a medial femoral paddle of the joint distractor away from a corresponding medial tibial paddle of the joint distractor medial femoral paddle, and
    moving a lateral femoral paddle of the joint distractor away from a corresponding lateral medial paddle of the joint distractor.

14. The method of claim 11, wherein distracting the patient's knee joint comprises positioning a spacer block on the tibial paddle of the sensor module.

15. The method of claim 11, wherein performing a balancing procedure comprises performing a ligament release on the patient's soft tissue.

16. The method of claim 11, further comprising:
    positioning the knee joint in flexion, and
    distracting the knee joint in flexion until the medial joint force and the lateral joint force are within a second predetermined percentage of each other as indicated on the visual indication displayed on the display module.

17. The method of claim 16, further comprising performing a number of resectioning cuts on the distal end of the patient's femur while the knee joint is distracted in flexion.

18. A method for performing an orthopaedic surgical procedure on a knee joint of a patient, the method comprising:
- positioning a tibial paddle of a sensor module on a resected proximal end of a patient's tibia, the tibial paddle including a sensor array positioned therein and having an upper tibial paddle housing with a substantially flat surface,
- distracting the patient's knee joint to establish a generally rectangular joint gap between the patient's proximal tibia and a resected distal end of the patient's femur such that the resected proximal end of the patient's tibia is approximately parallel with the resected distal end of the patient's femur, wherein distracting the patient's knee joint comprises positioning a joint distractor in the patient's knee joint such that a medial tibial paddle of the joint distractor and a lateral tibial paddle of the joint distractor each contacts the upper tibial paddle housing of the sensor module;
- monitoring a plurality of light emitting diodes located on the sensor module, the plurality of light emitting diodes being illuminated in a pattern to provide a visual indication of the relative balance of a medial joint force and a lateral joint force of the patient's knee joint displayed on the display of the sensor module; and
- performing a ligament release procedure on the patient's knee joint until the medial joint force and the lateral joint force are within a first predetermined percentage of each other as indicated by the plurality of light emitting diodes.

\* \* \* \* \*